US011952637B2

(12) United States Patent
Green et al.

(10) Patent No.: US 11,952,637 B2
(45) Date of Patent: Apr. 9, 2024

(54) RAPID LOW-COST DETECTION OF SARS-COV-2 USING ISOTHERMAL AMPLIFICATION AND SENSING METHODS

(71) Applicants: ARIZONA BOARD OF REGENTS ON BEHALF OF ARIZONA STATE UNIVERSITY, Scottsdale, AZ (US); THE GOVERNING COUNCIL OF THE UNIVERSITY OF TORONTO, Toronto (CA)

(72) Inventors: Alexander Green, Boston, MA (US); Keith Pardee, Toronto (CA); Margot Karlikow, Toronto (CA); Kaiyue Wu, Tempe, AZ (US); Masoud Norouzi, Toronto (CA)

(73) Assignees: ARIZONA BOARD OF REGENTS ON BEHALF OF ARIZONA STATE UNIVERSITY, Scottsdale, AZ (US); THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 18/001,395

(22) PCT Filed: Jun. 11, 2021

(86) PCT No.: PCT/US2021/037092
§ 371 (c)(1),
(2) Date: Dec. 9, 2022

(87) PCT Pub. No.: WO2021/252956
PCT Pub. Date: Dec. 16, 2021

(65) Prior Publication Data
US 2023/0212698 A1    Jul. 6, 2023

Related U.S. Application Data

(60) Provisional application No. 63/038,609, filed on Jun. 12, 2020.

(51) Int. Cl.
*C12Q 1/70* (2006.01)
*C12Q 1/6897* (2018.01)

(52) U.S. Cl.
CPC ........... *C12Q 1/6897* (2013.01); *C12Q 1/701* (2013.01)

(58) Field of Classification Search
None
See application file for complete search history.

(56) References Cited

U.S. PATENT DOCUMENTS 4,458,066 A    7/1984    Caruthers et al.
4,683,195 A    7/1987    Mullis et al.
4,683,202 A    7/1987    Mullis 5,494,810 A        2/1996    Barney et al.
2015/0275203 A1    10/2015   Green et al.
2020/0080137 A1    3/2020    Green et al.

FOREIGN PATENT DOCUMENTS

CN    111139242 A    5/2020
WO    2021252956     12/2021

OTHER PUBLICATIONS

Pardee et al., 2016, Rapid, Low-Cost Detection of Zika Virus Using Programmable Biomolecular Components. Cell 165, 1255-1266.*
"PUREExpress In Vitro Protein Synthesis Kit" (downloaded from internet May 8, 2023, https://www.neb-online.de/en/proteinexpression/purexpress-in-vitro-protein-synthesis-kit/).*
Harbers. Wheat germ systems for cell-free protein expression. FEBS Letters 588 (2014) 2762-2773.*
Reusken et al. Laboratory readiness and response for novel coronavirus (2019-nCoV) in expert laboratories in 30 EU/EEA countries, Jan. 2020. Euro Surveill. Feb. 2020;25(6):2000082.*
GenBank Accession No. MT127113.1. Severe acute respiratory syndrome coronavirus 2 isolate SARS-CoV-2/ humanNIE/NIHE/2020 ORF1ab polyprotein, 3'-to-5' exonuclease region, gene, partial cds. Apr. 6, 2020 [online], [Retrieved on Nov. 9, 2021] URL: https://www.ncbi.nlm.nih.gov/nuccore/MT127113.
International Search Report and Written Opinion issued in corresponding PCT Application No. PCT/US2021/037092, dated Dec. 10, 2021.
Beaucage et al., "Deoxynuleoside Phosphoramidites-A new Class of Key Intermediates for Deoxypolynucleotide Synthesis", 1981, Tetrahedron Letters 22:1859-1862.
Brown et al., "Chemical Synthesis and Cloning of a Tyrosine tRNA Gene," 1979, Meth. Enzymol. 68:109-151.
Chakravarthy et al., "Engineered RNA biosensors enable ultrasensitive SARS-CoV-2 detection in a simple color and luminescence assay", medRxiv preprint doi: https://doi.org/10.1101/2021.01.08.21249426; this version posted Apr. 16, 2021.
Corman et al., "Detection of 2019 novel coronavirus (2019-nCov) by real-time RT-PCR", Euro Surveill. 2020. https://eurosurveillance.org/content/10.2807/1560-7917.ES.2020.25.3.2000045.
Goodchild, "Conjugates of Oligonucleotides and Modified Oligonucleotides: A Review of Their Synthesis and Properties" 1990, Bioconjugate Chemistry 1(3): 165-187.
Green et al.,"Toehold Switches: De-Novo-Designed Regulators of Gene Expression", 2014, Cell 159, 925-939.
Hong et al., Precise and Programmable Detection of Mutations Using Ultraspecific Riboregulators Cell, 180(5): 1018-1032 (2020).
Ma et al., "Low-cost detection of norovirus using paper-based cell-free systems and synbody-based viral enrichment", Synth Biol 3(1) 2018.

(Continued)

*Primary Examiner* — Nianxiang Zou
(74) *Attorney, Agent, or Firm* — Quarles & Brady, LLP

(57) ABSTRACT

Provided herein are methods and compositions for rapid, highly sensitive detection of SARS-CoV-2 in biological samples. In particular, provided herein is a rapid, low-cost method for detecting SARS-CoV-2 that provides reliable, visible test results and does not require PCR reagents, elaborate biosafety precautions, or sophisticated laboratory equipment.

19 Claims, 55 Drawing Sheets

Specification includes a Sequence Listing.

(56) References Cited

OTHER PUBLICATIONS

Narang et al., "Improved Phosphotriester Method for the Synthesis of Gene Fragments," 1979, Meth. Enzymol. 68:90-98.
Owczarzy et al., "Predicting Stability of DNA Duplexes in Solutions Containing Magnesium and Monovalent Cations", 2008, Biochemistry, 47: 5336-5353.
Wetmur, "DNA Probes: Applications of the Principles of Nucleic Acid Hybridization", 1991, Critical Review in Biochem. and Mol. Biol. 26(3/4):227-259.
https://github.com/Albert09111/SNIPR; last visited Oct. 24, 2023, pp. 1-4.

* cited by examiner

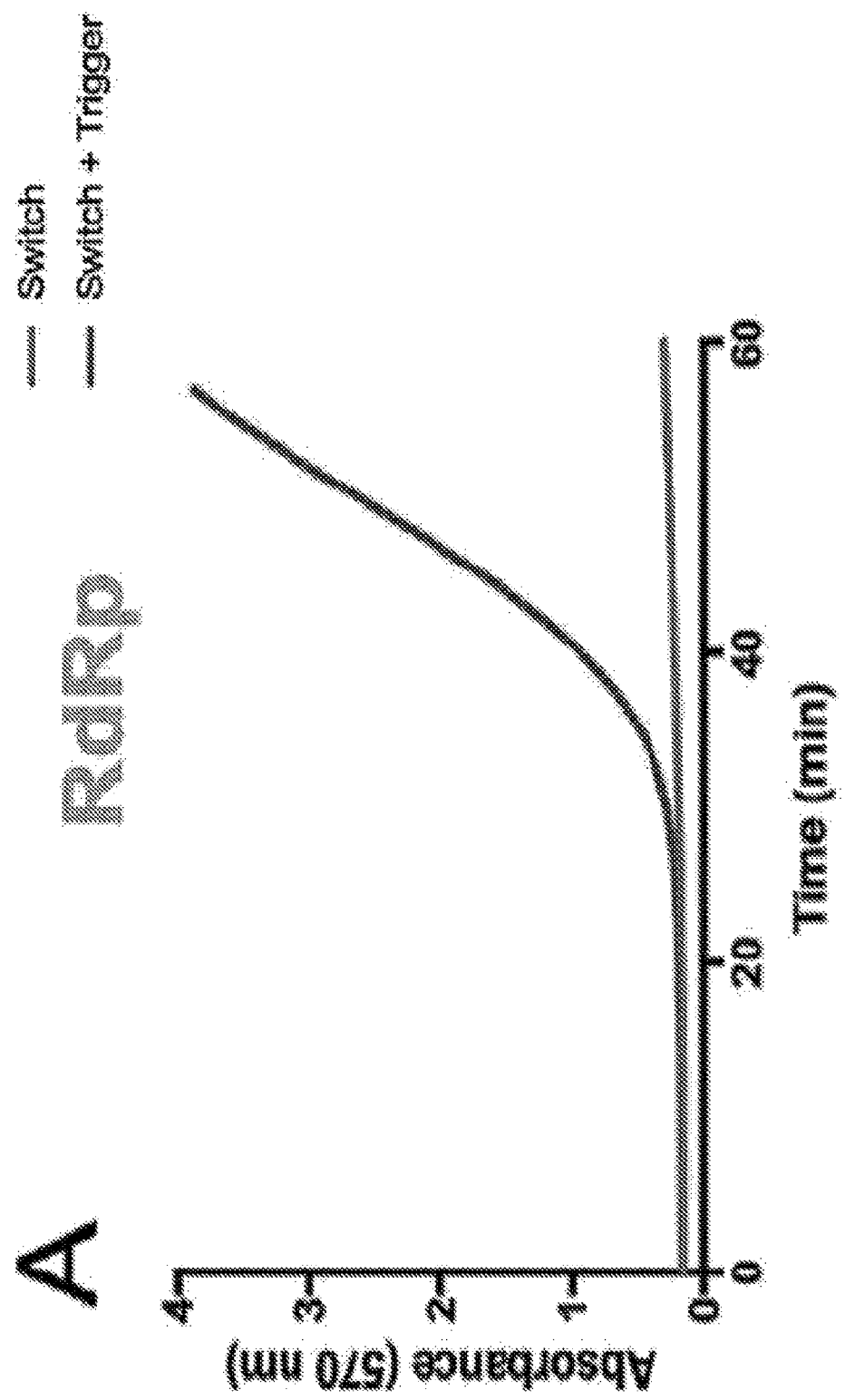
Figure 2A-F

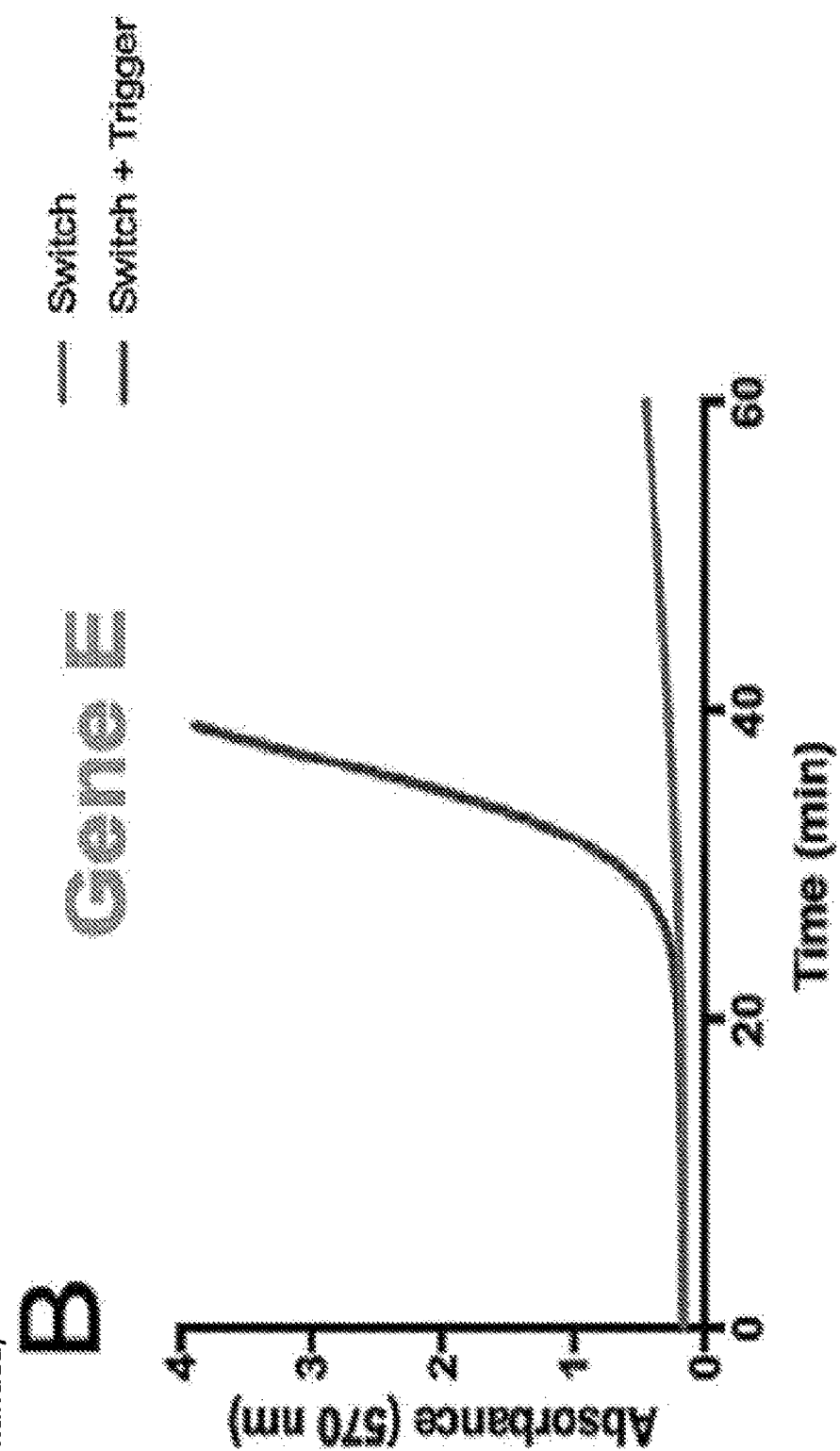
Figure 2A-F (Continued)

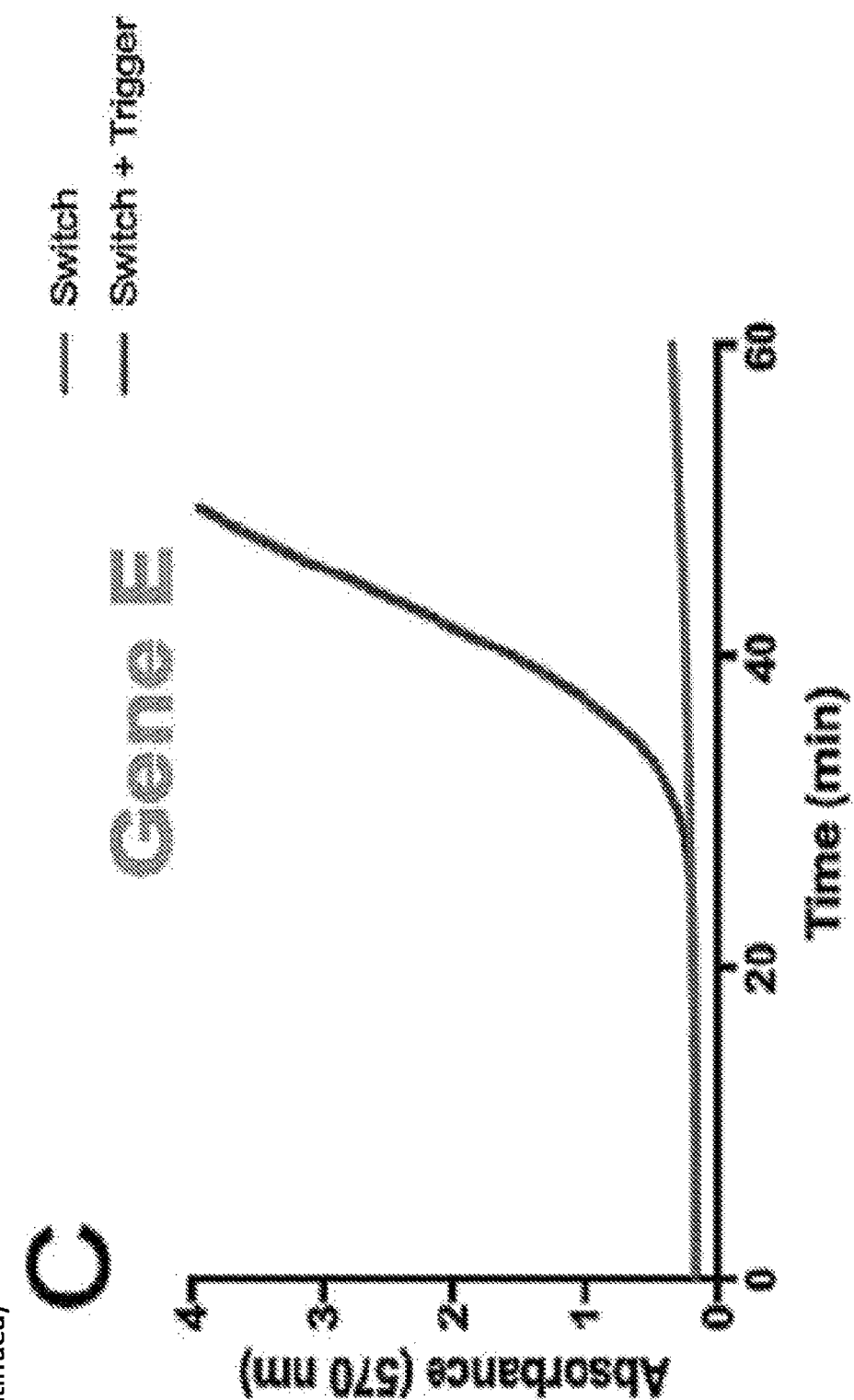
Figure 2A-F (Continued)

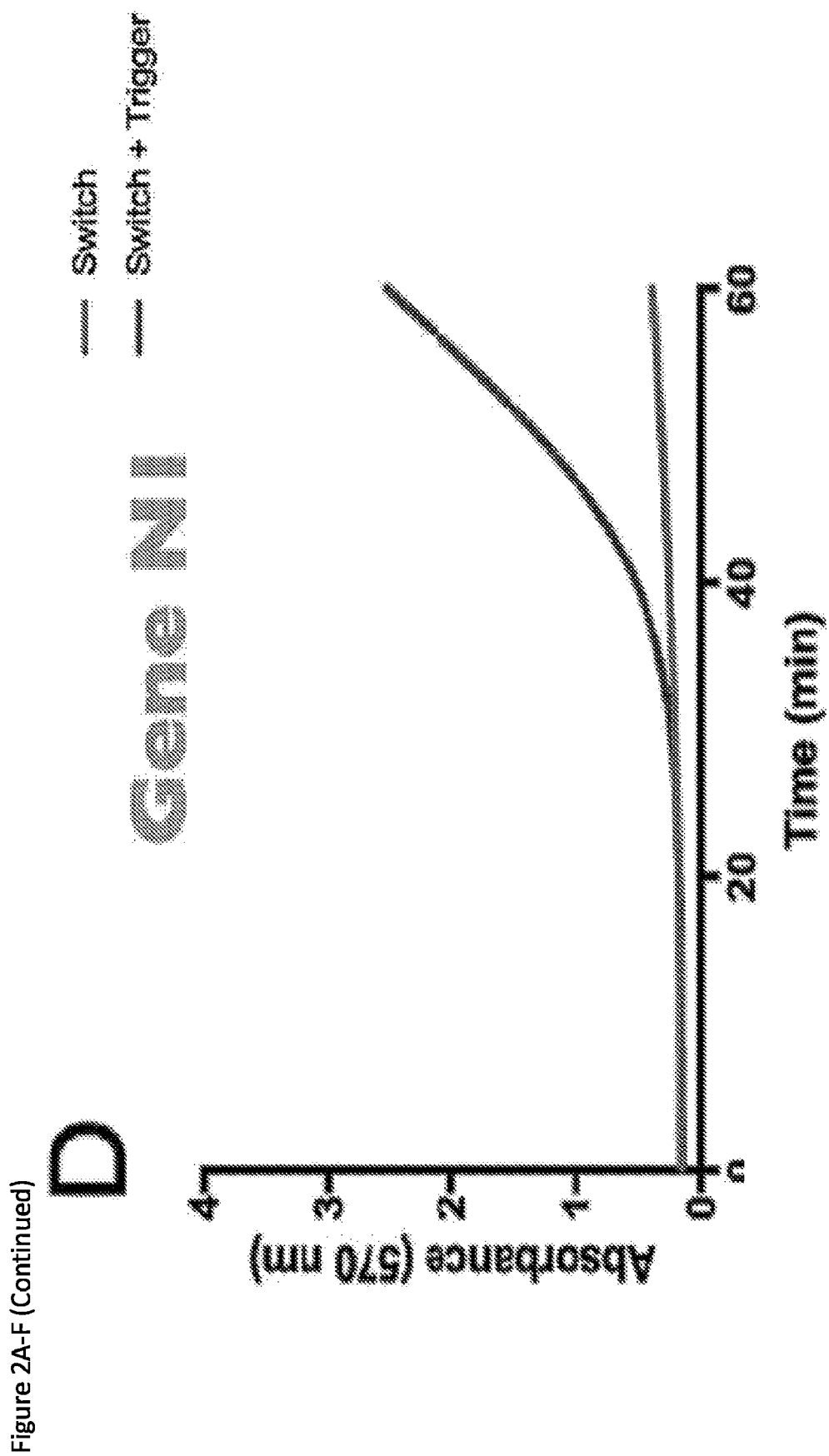
Figure 2A-F (Continued)

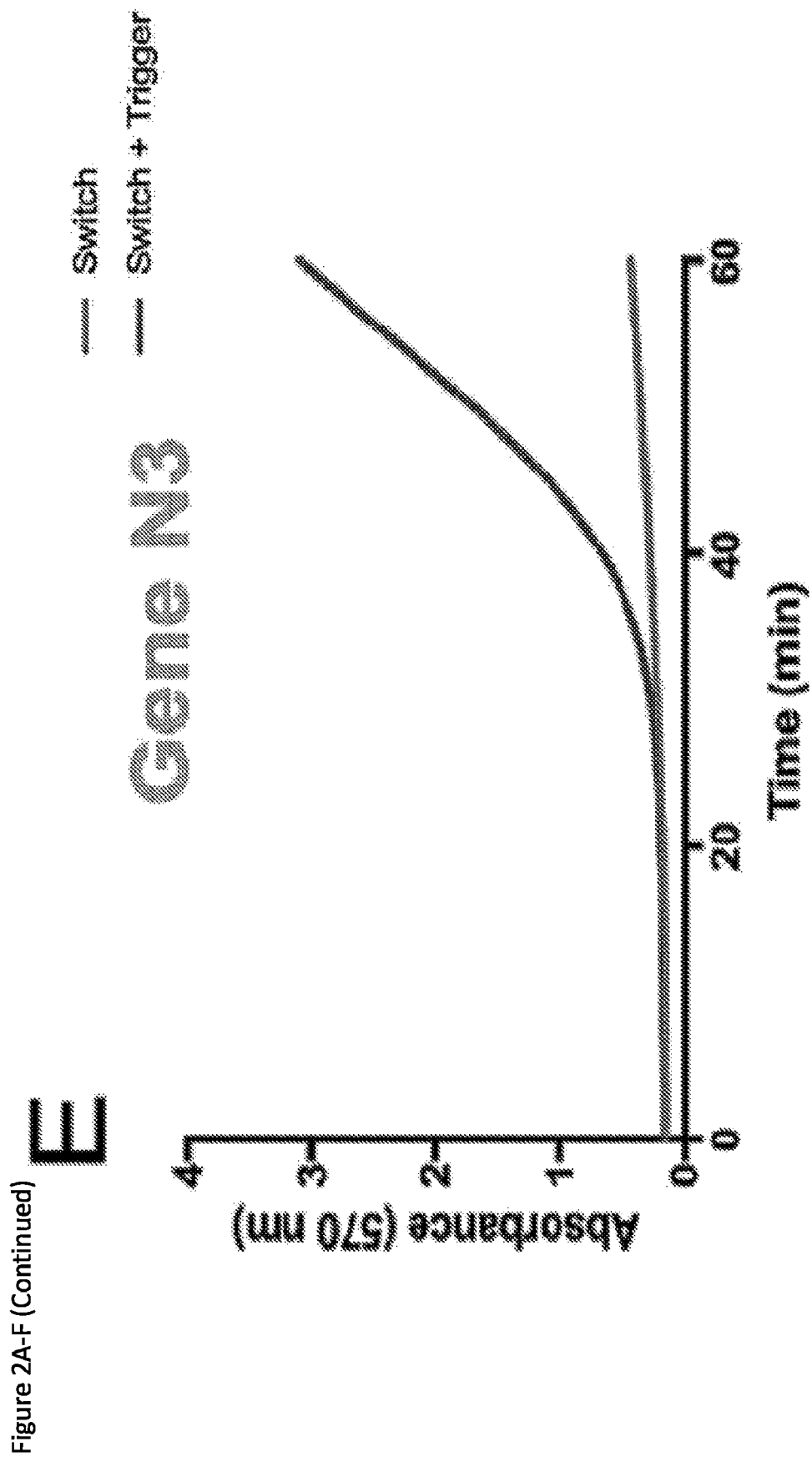
Figure 2A-F (Continued)

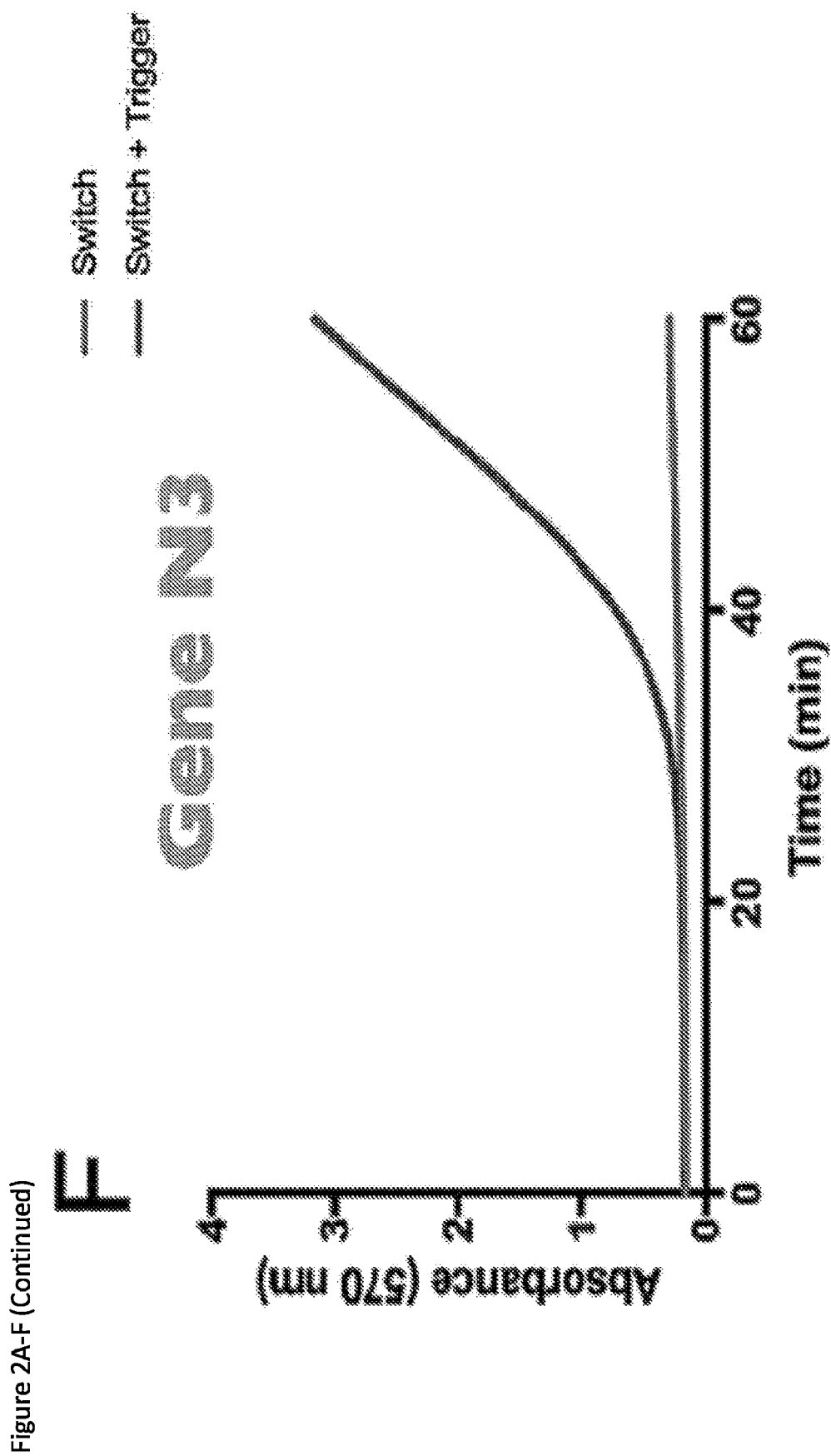
Figure 2A-F (Continued)

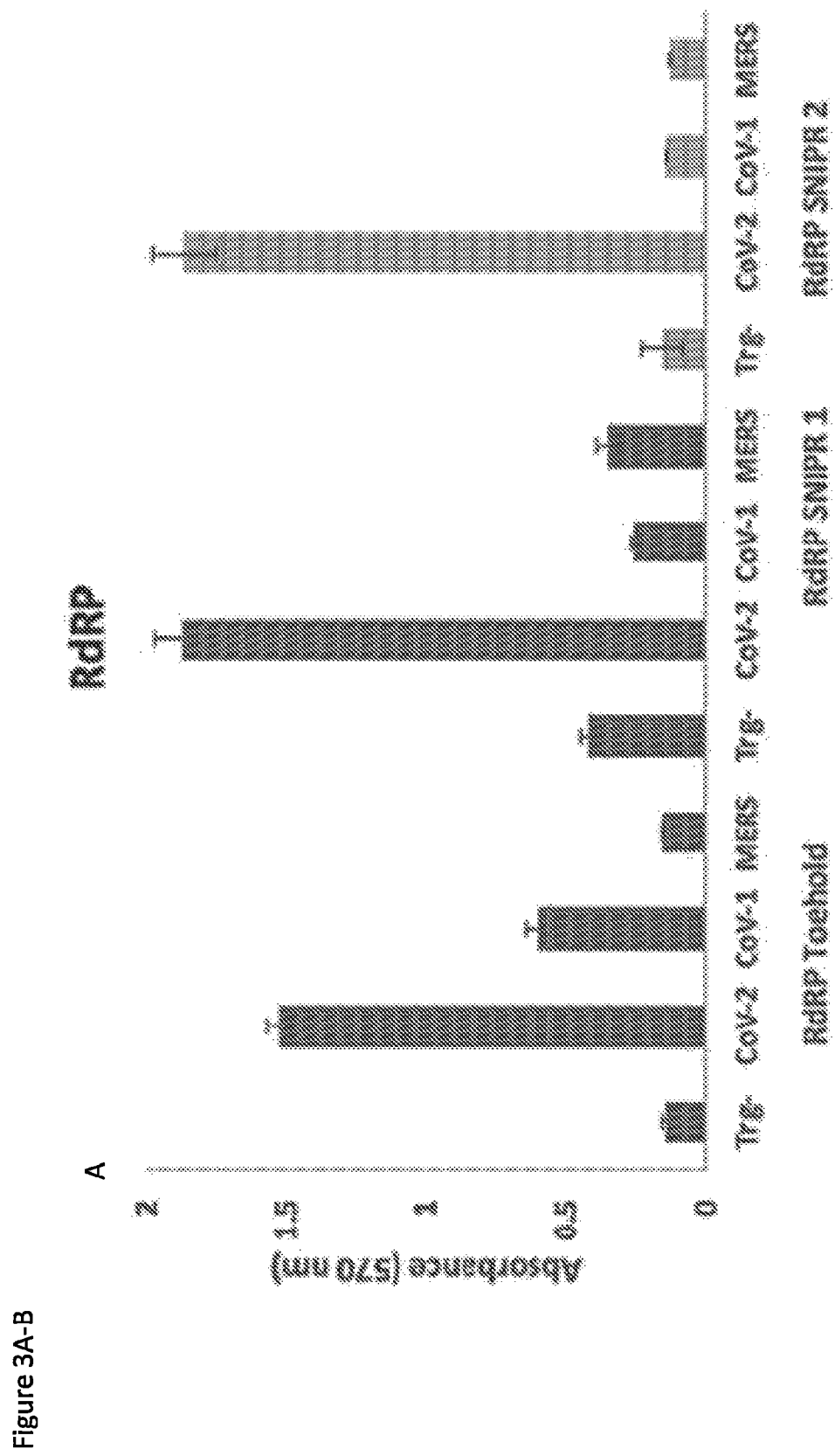
Figure 3A-B

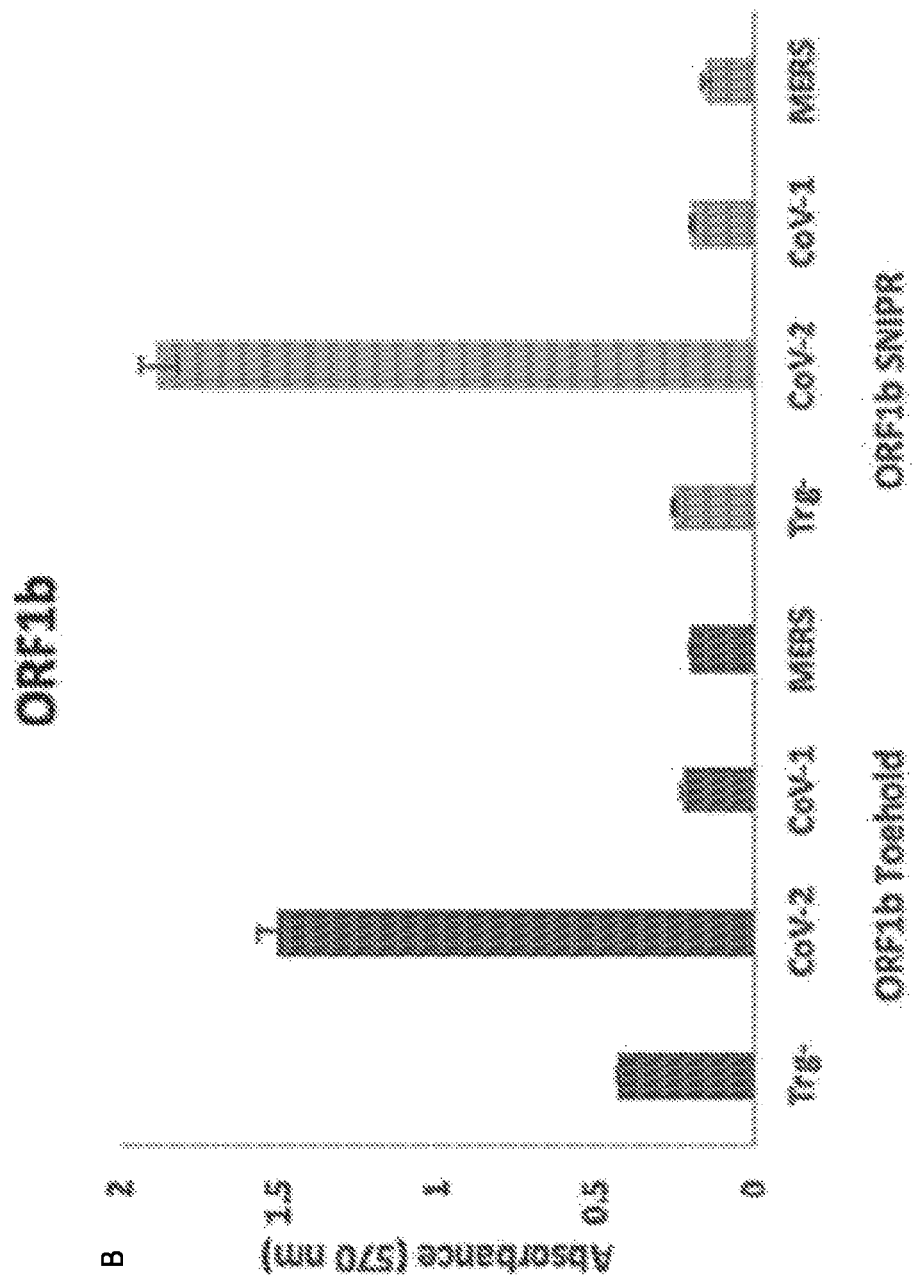
Figure 3A-B (Continued)

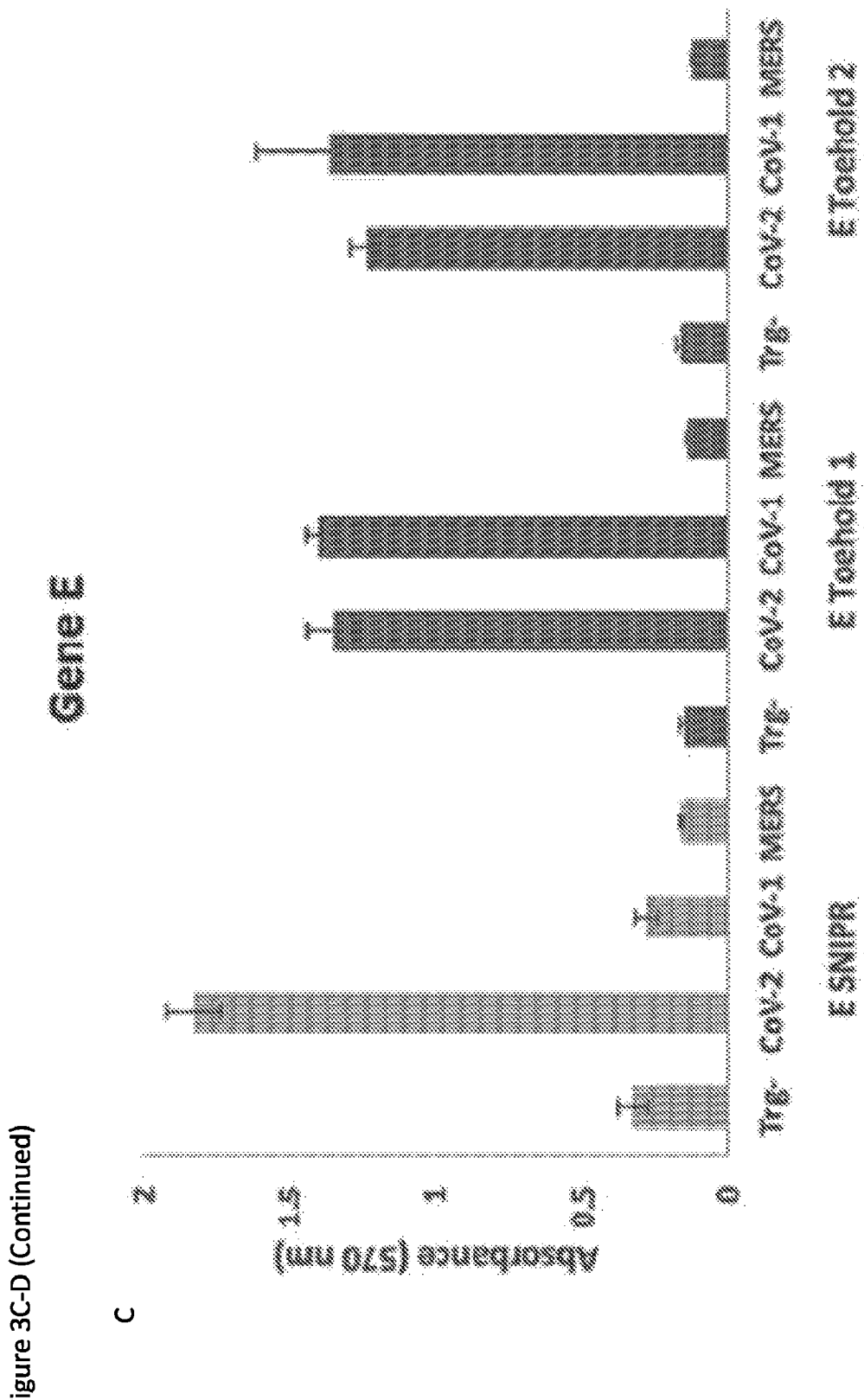
Figure 3C-D (Continued)

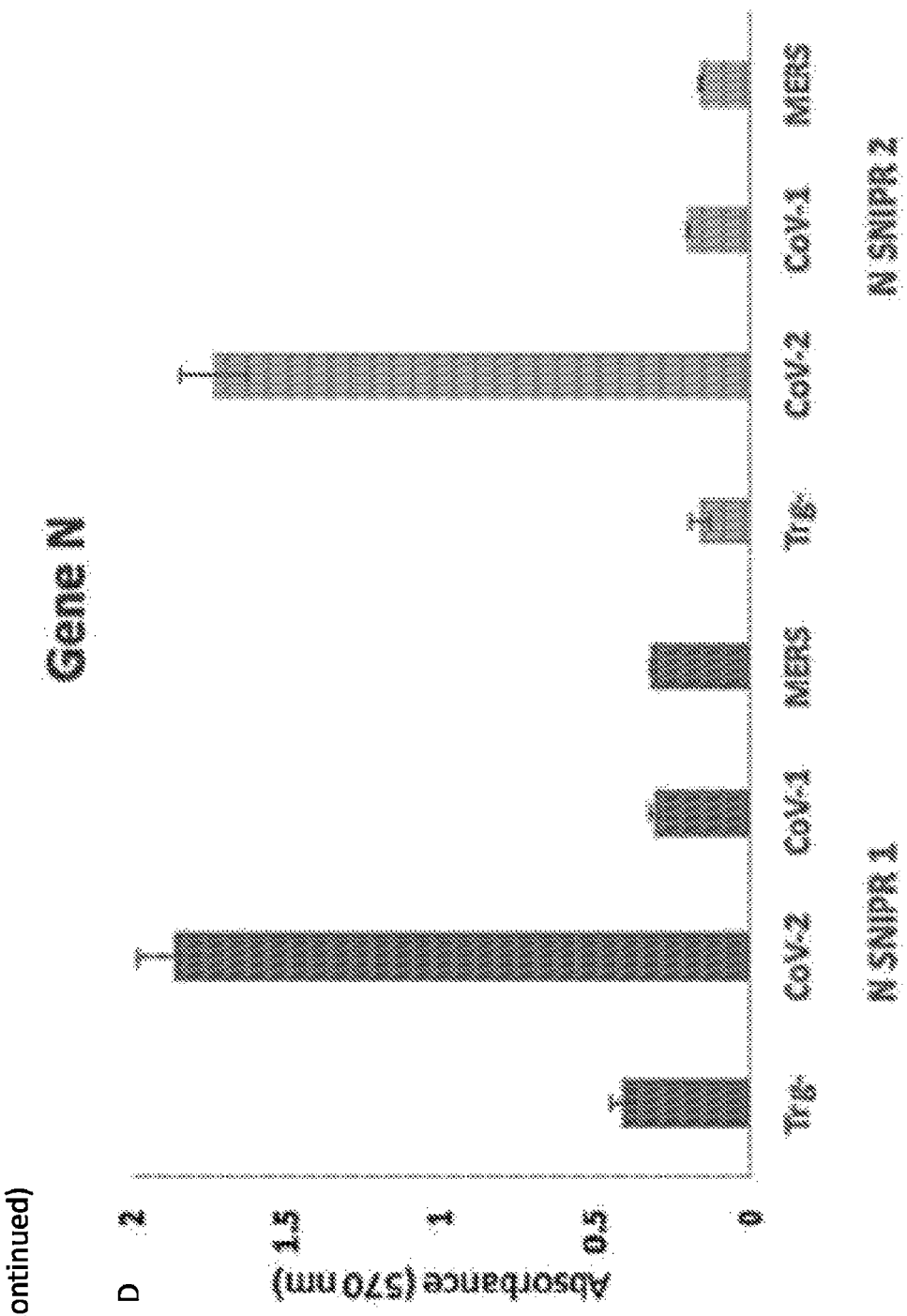
Figure 3C-D (Continued)

Figure 4A-C
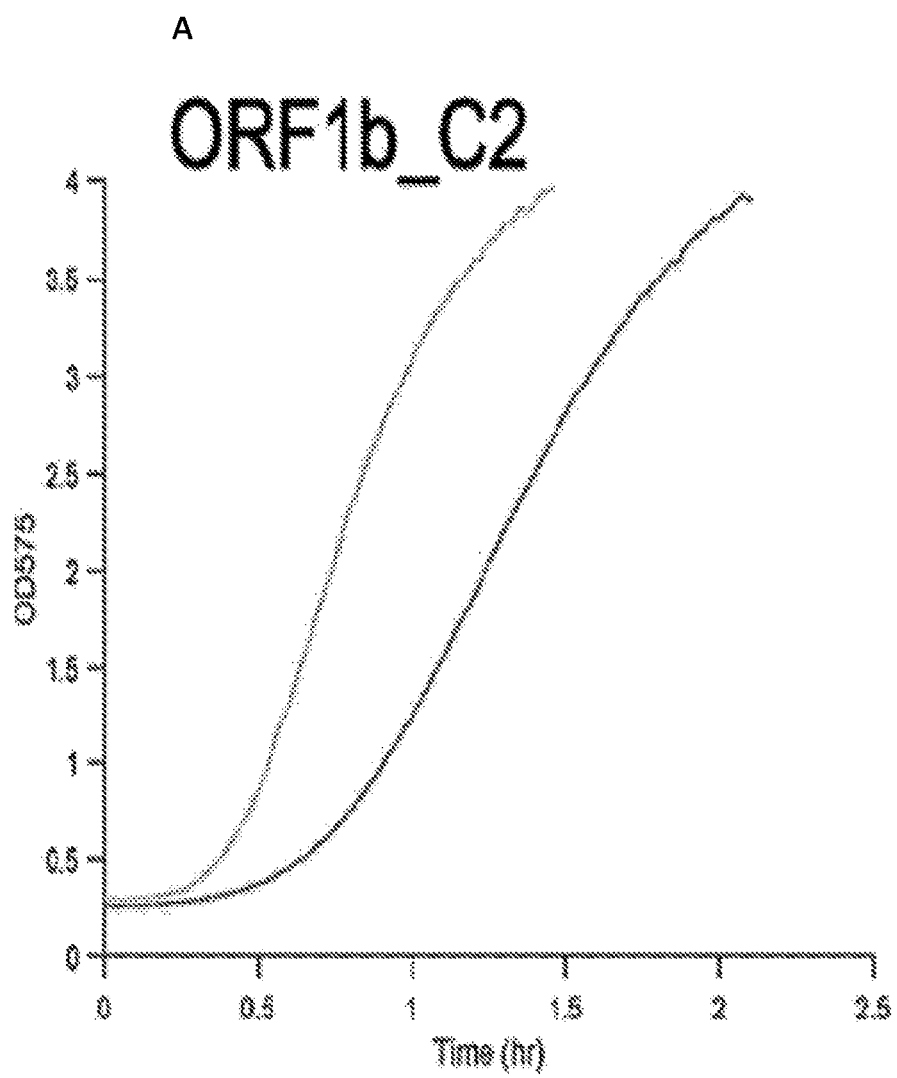

Figure 4A-C (Continued)
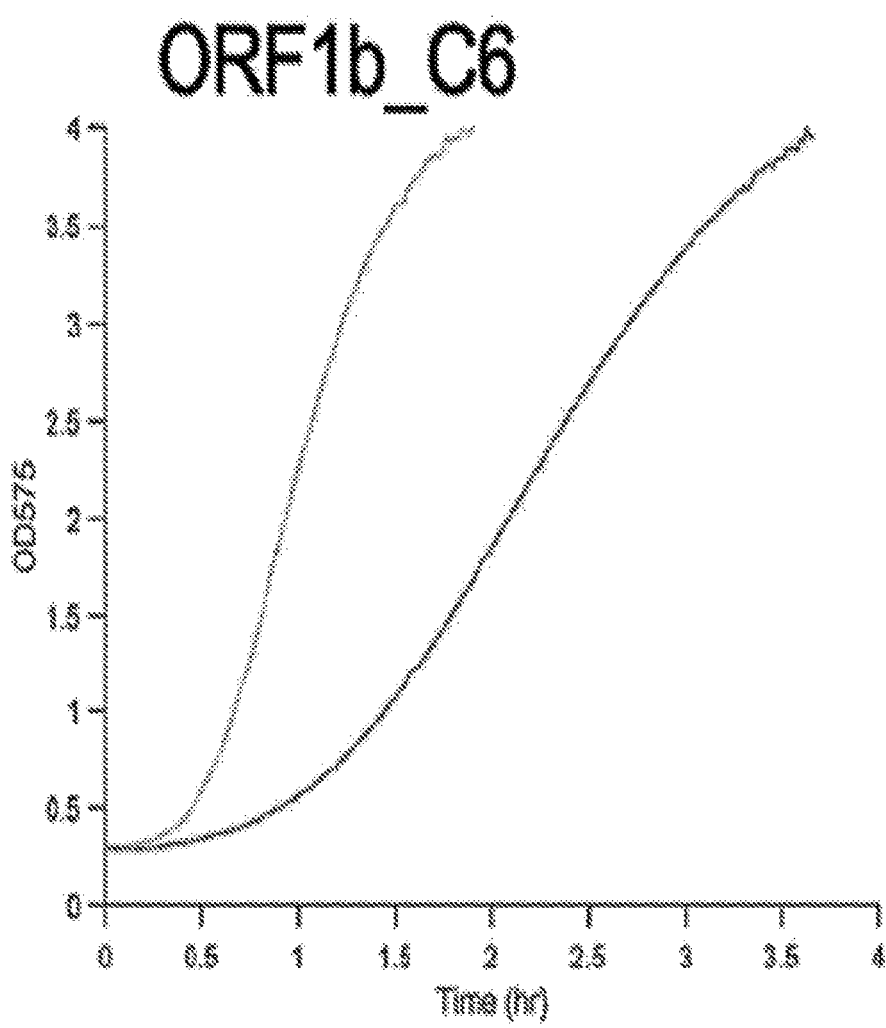

Figure 4A-C (Continued)
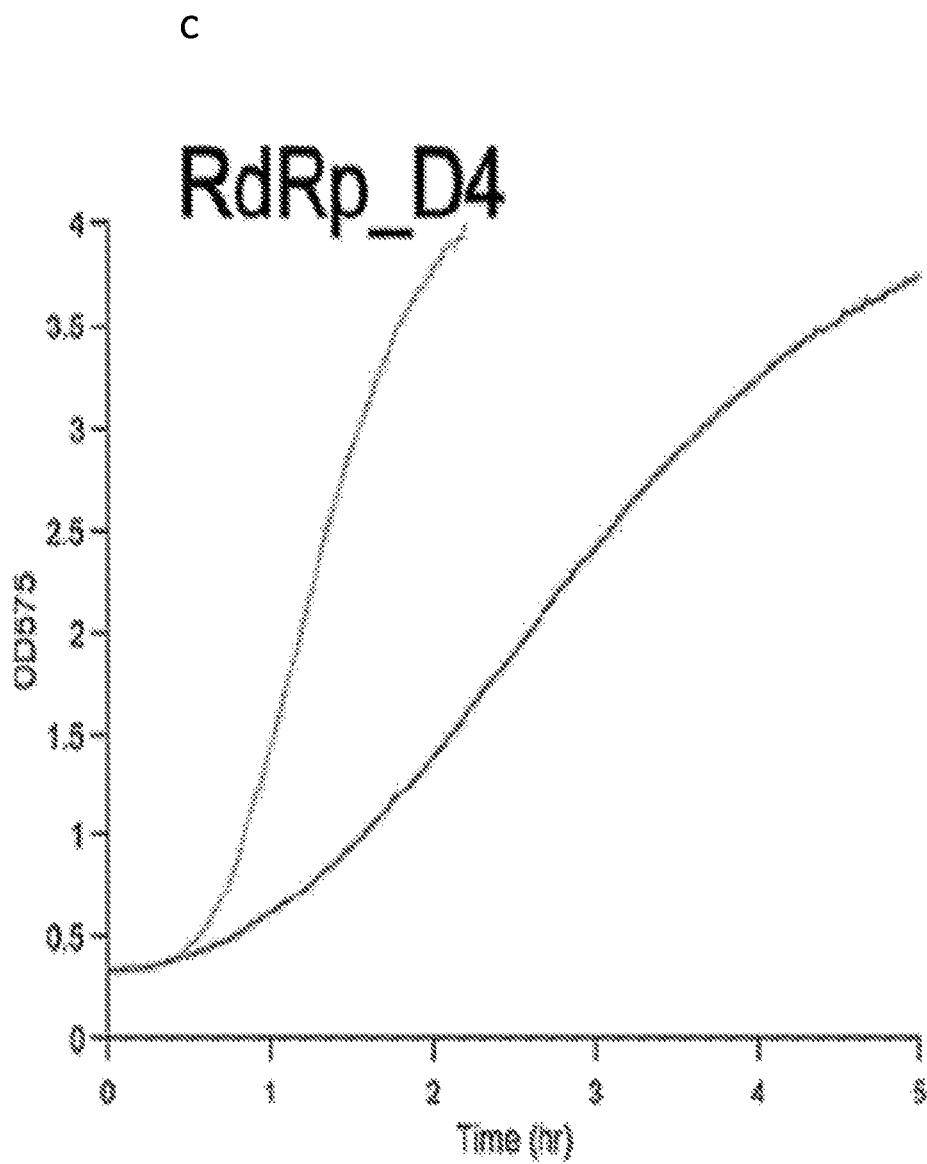

Figure 4D-F
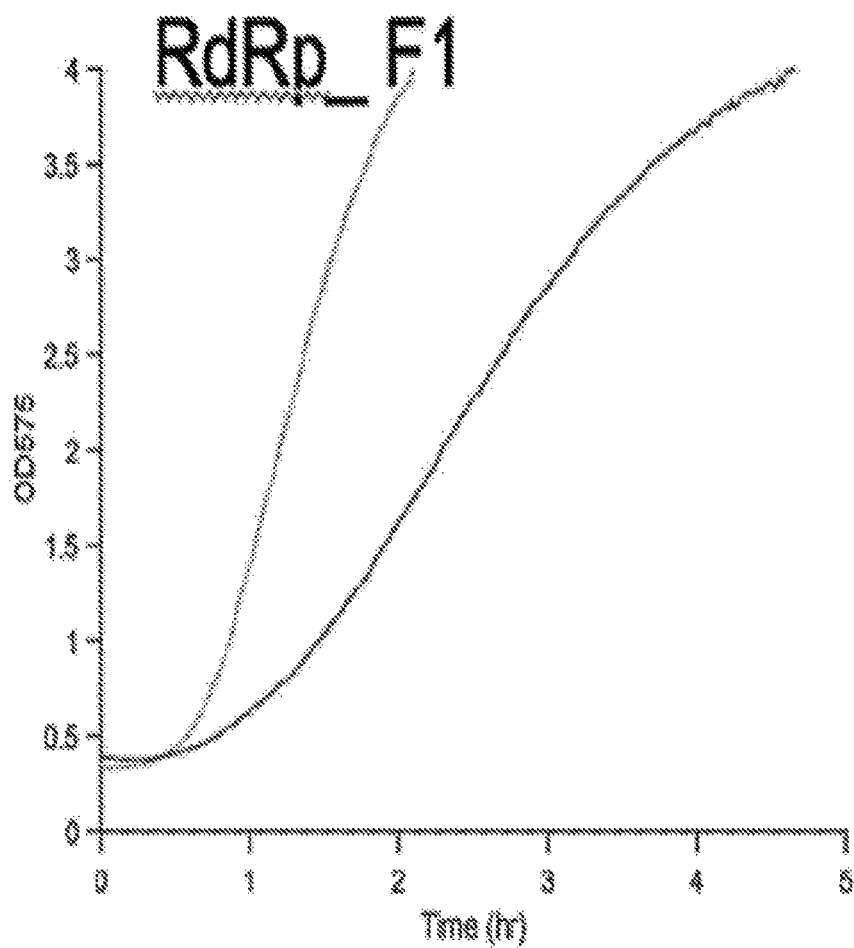

Figure 4D-F (Continued)
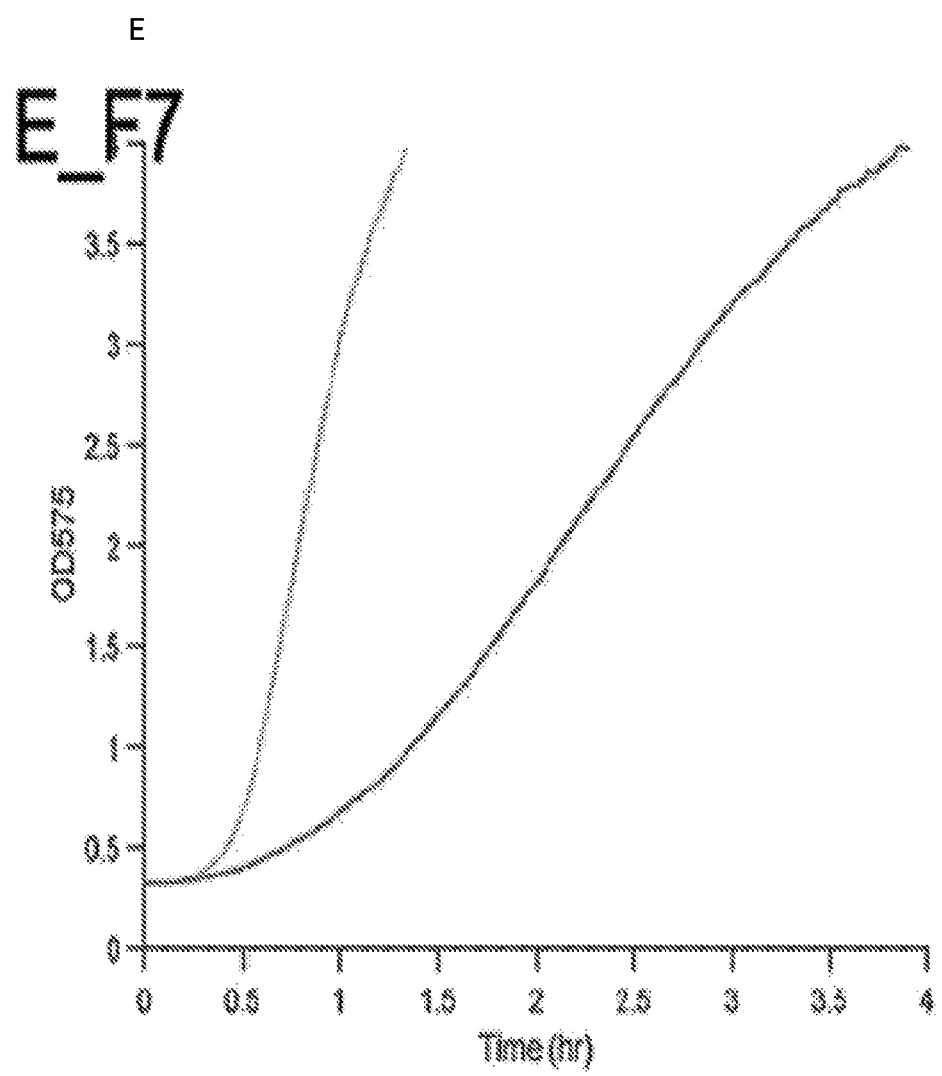

Figure 4D-F (Continued)
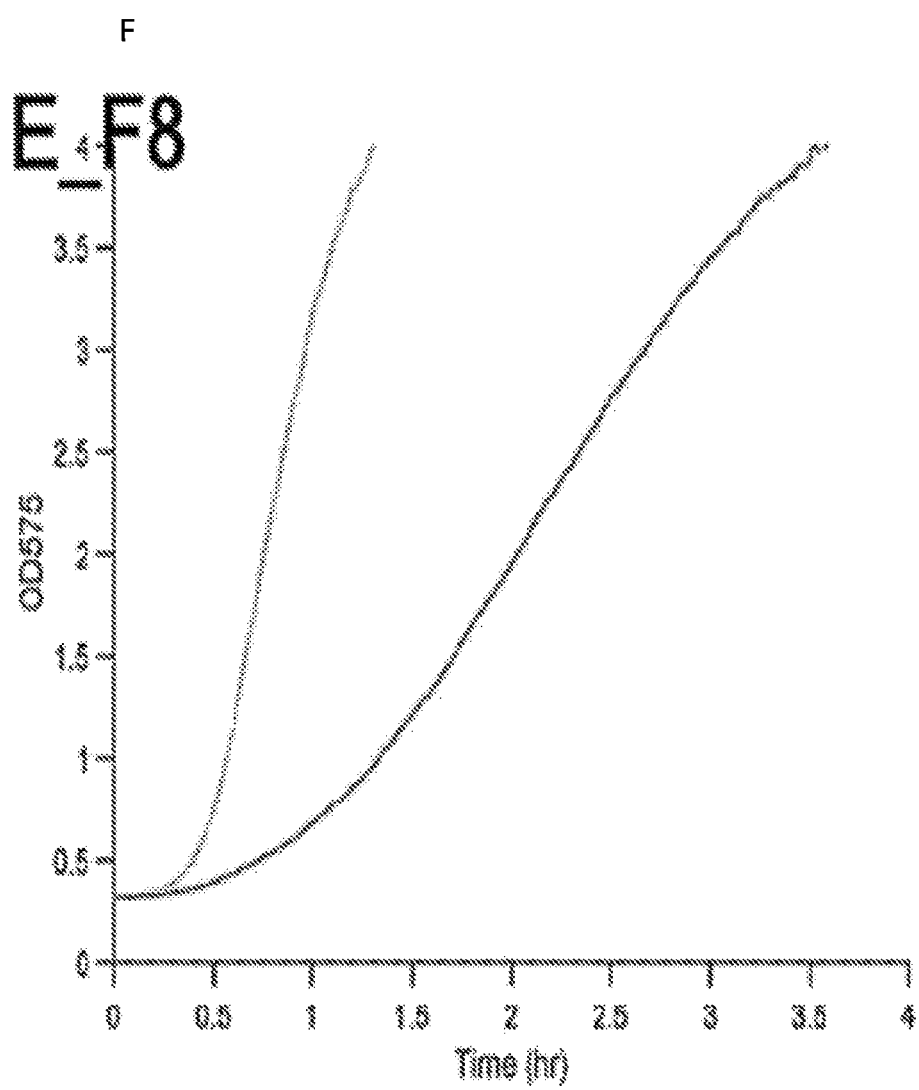

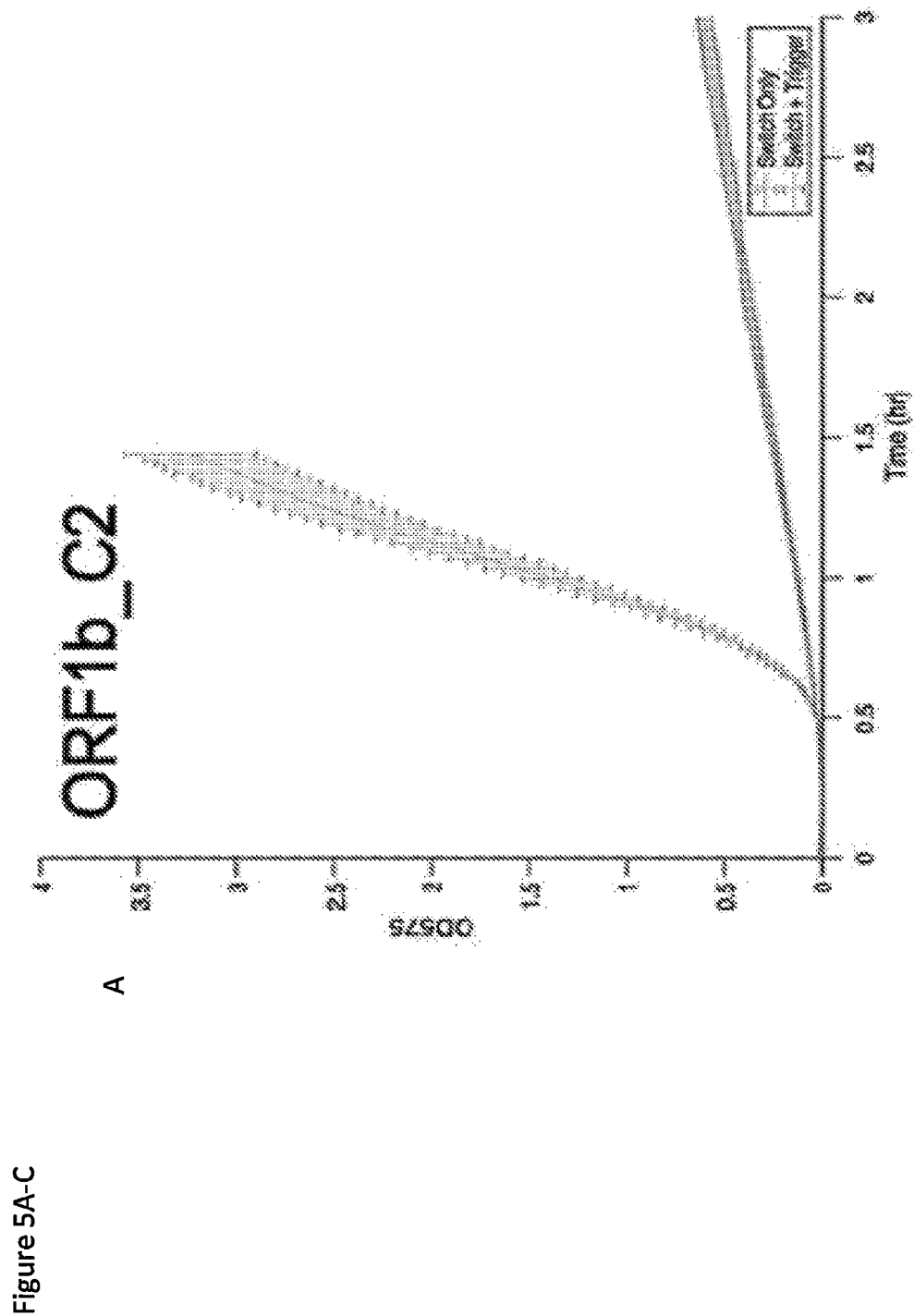
Figure 5A-C

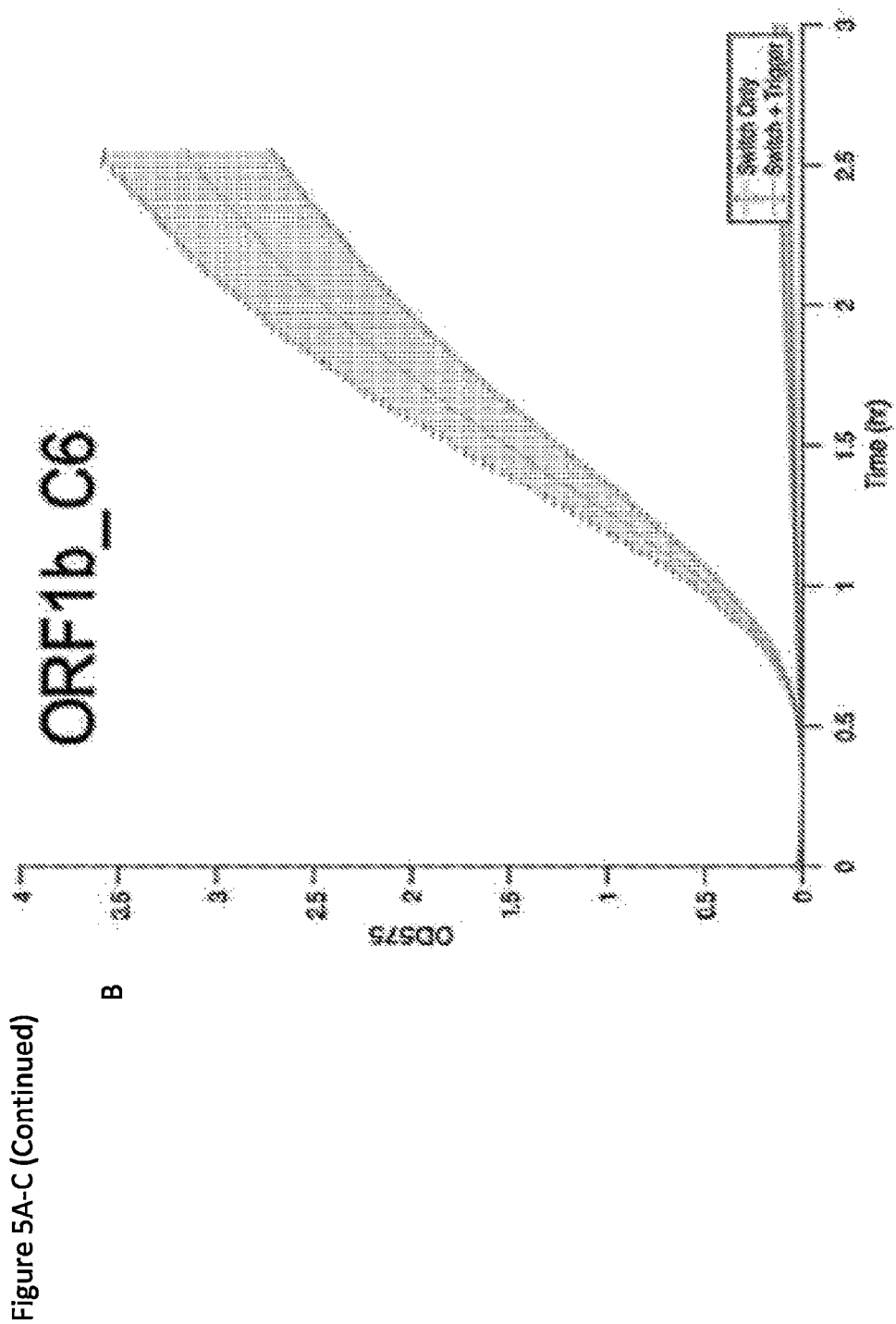
Figure 5A-C (Continued)

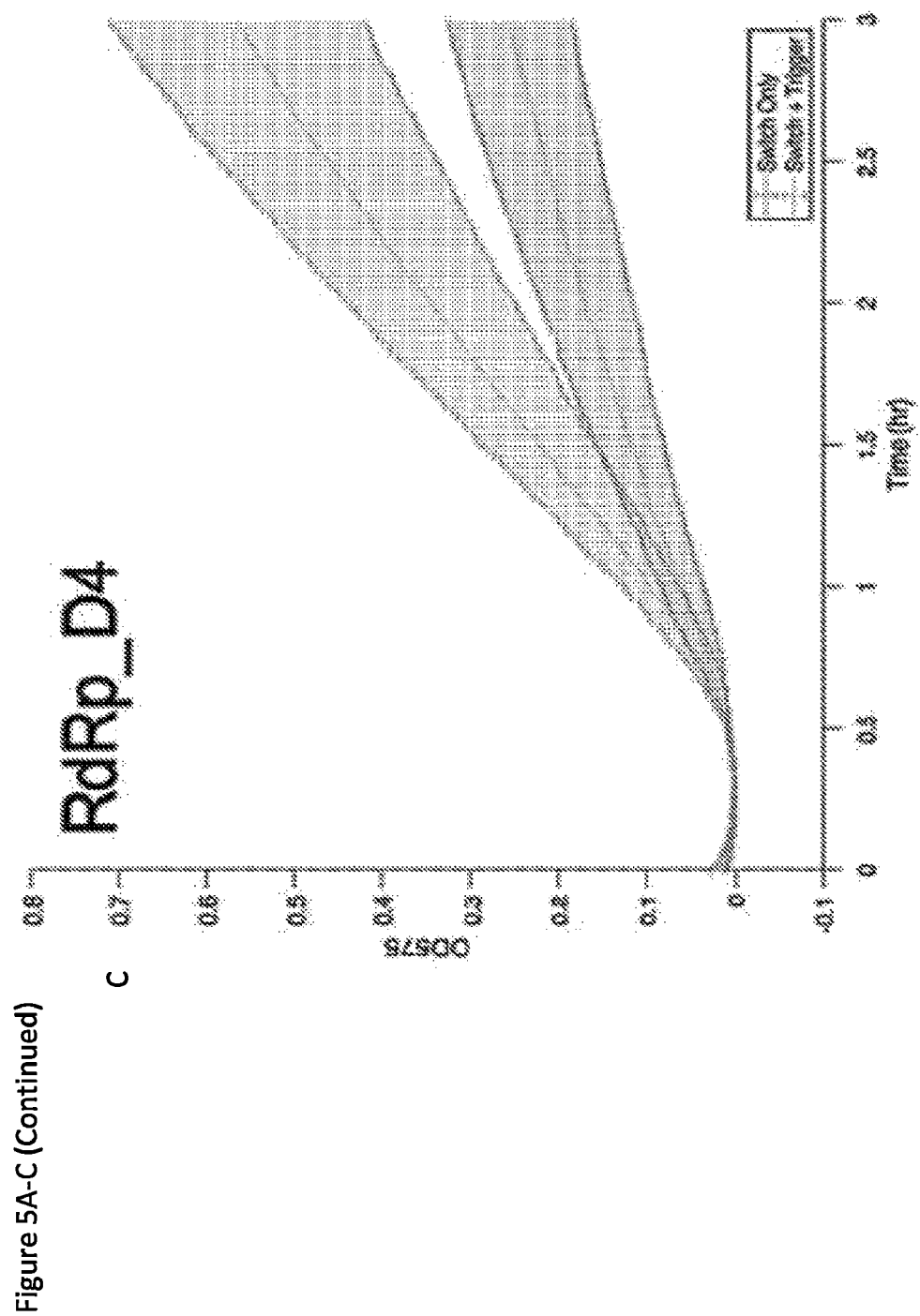
Figure 5A-C (Continued)

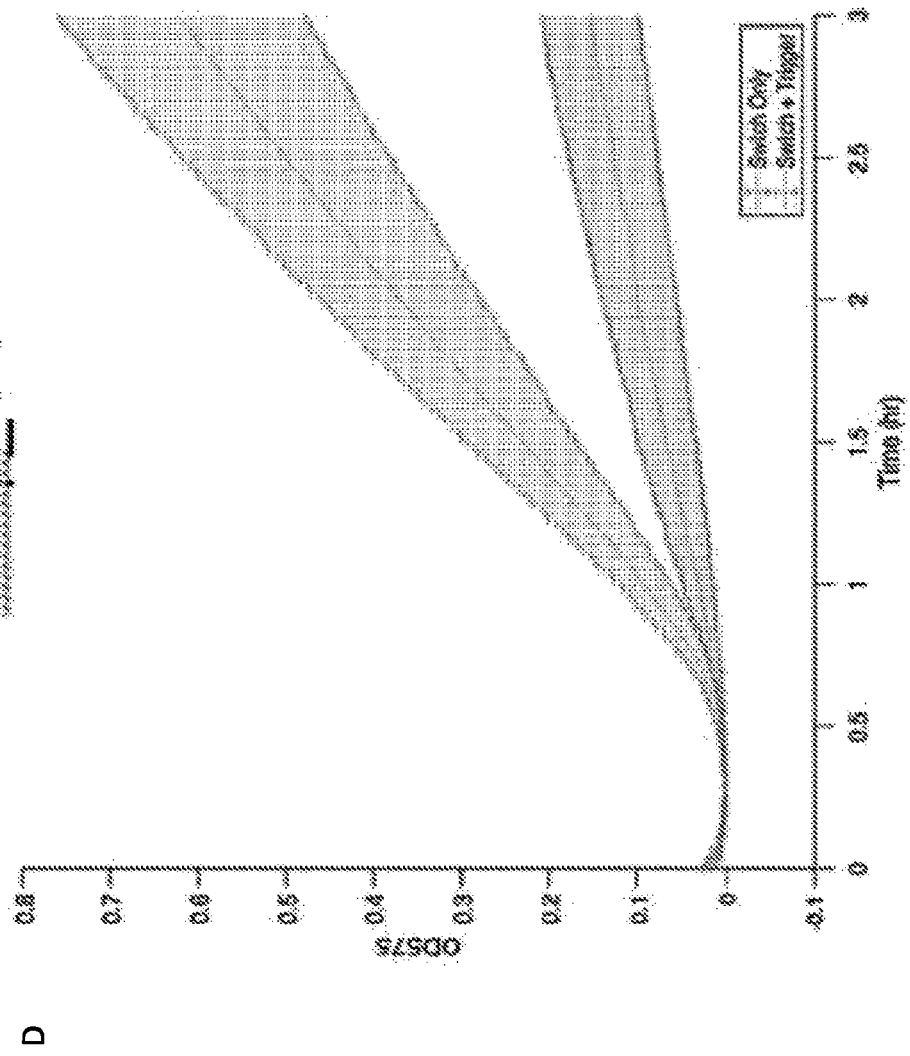
Figure 5D-F

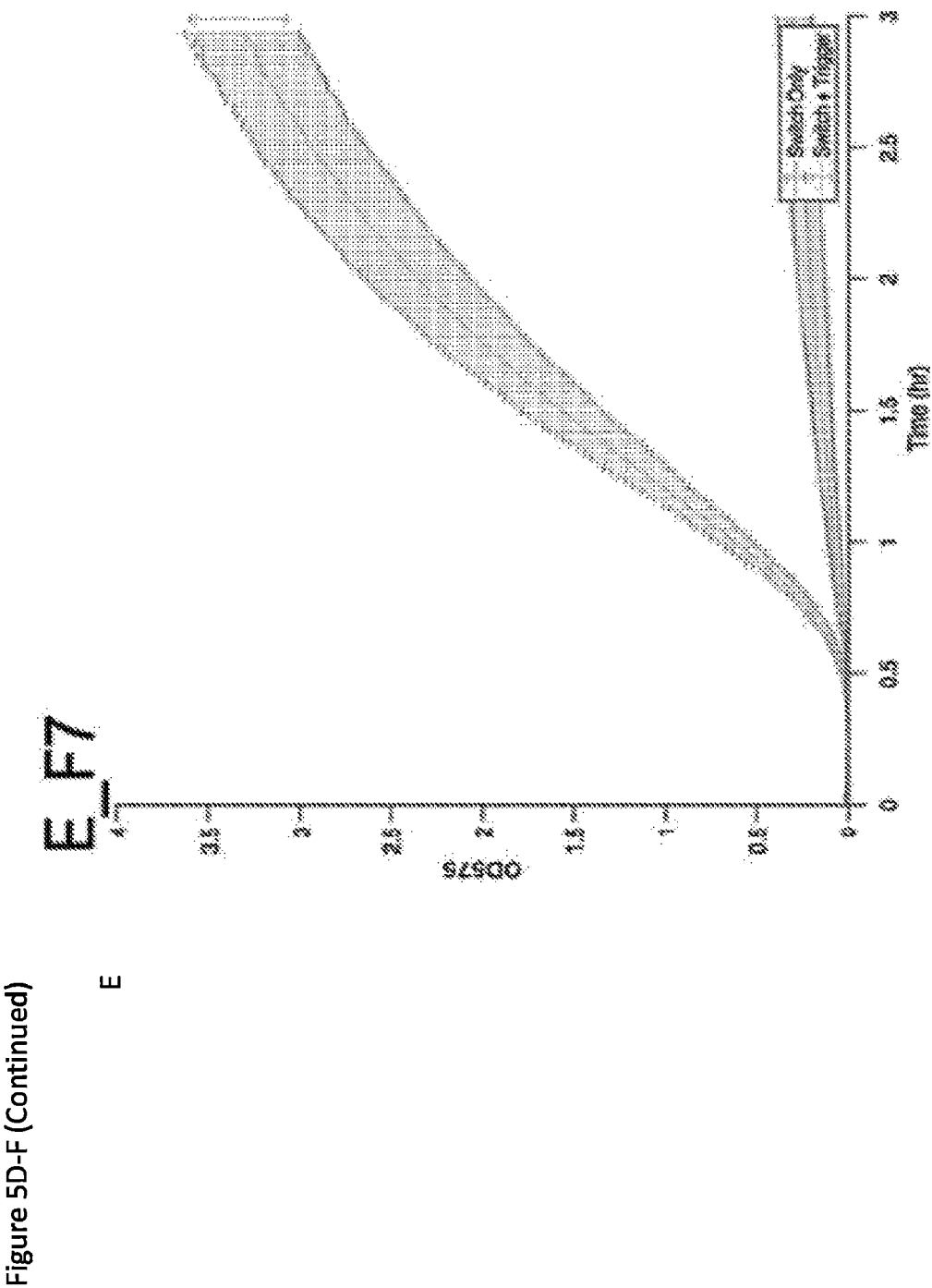
Figure 5D-F (Continued)

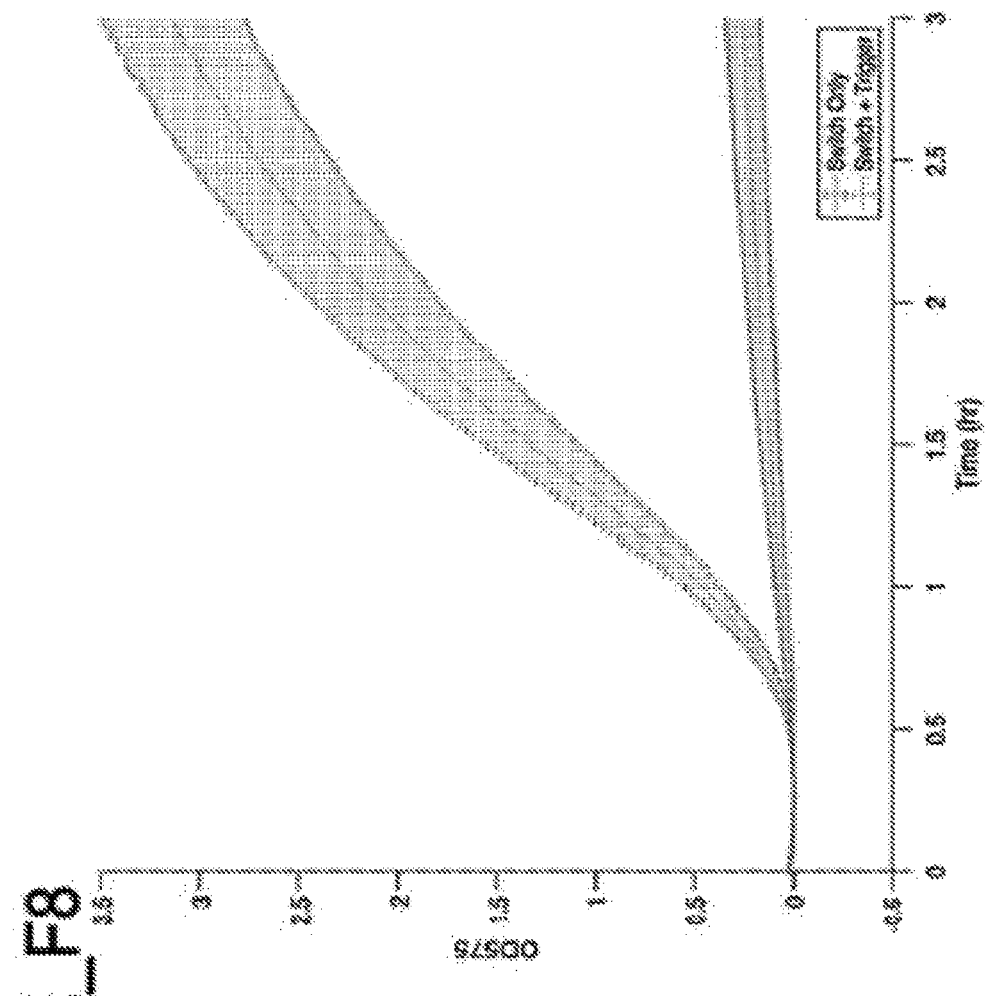
Figure 5D-F (Continued)

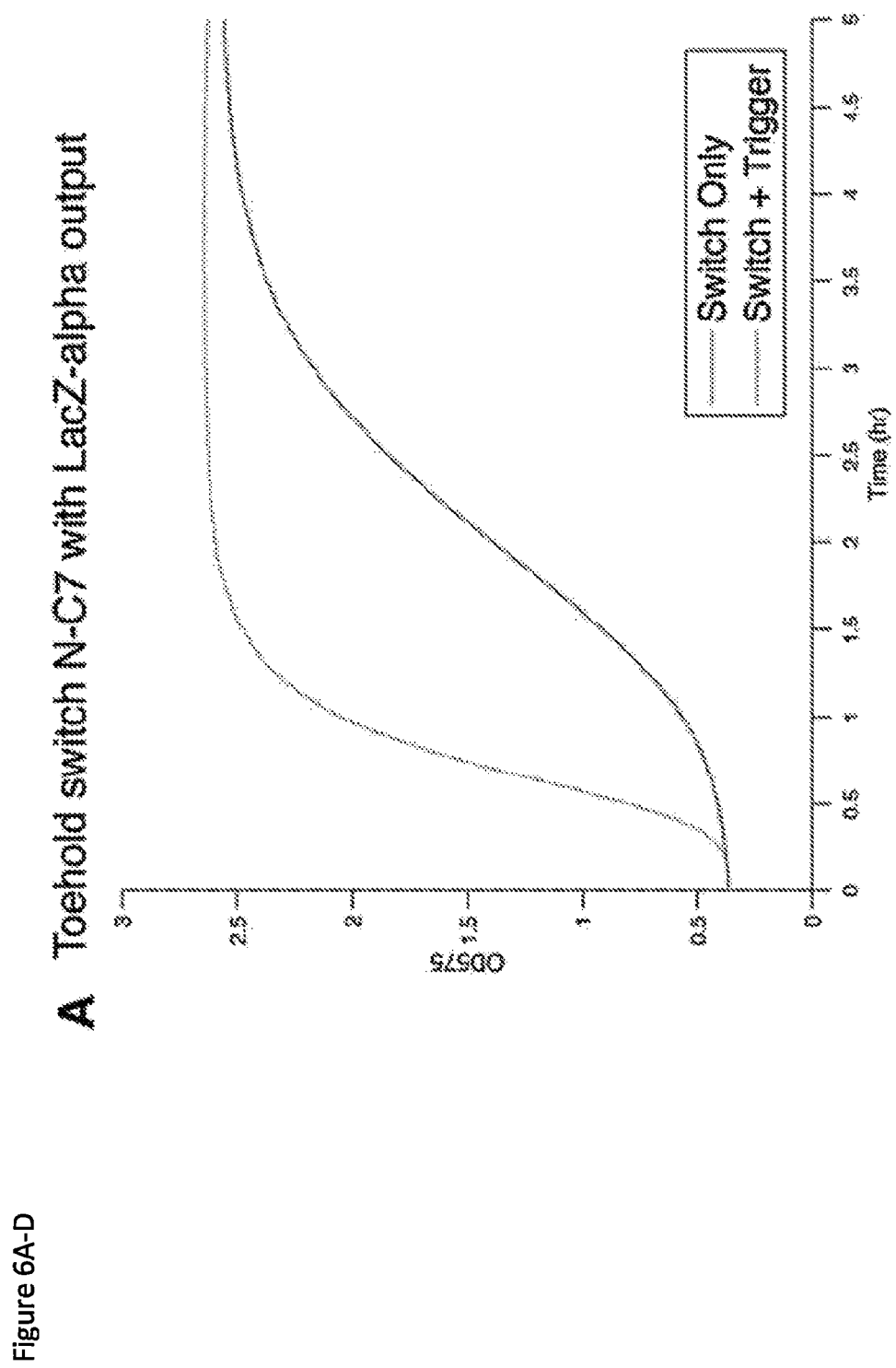
Figure 6A-D

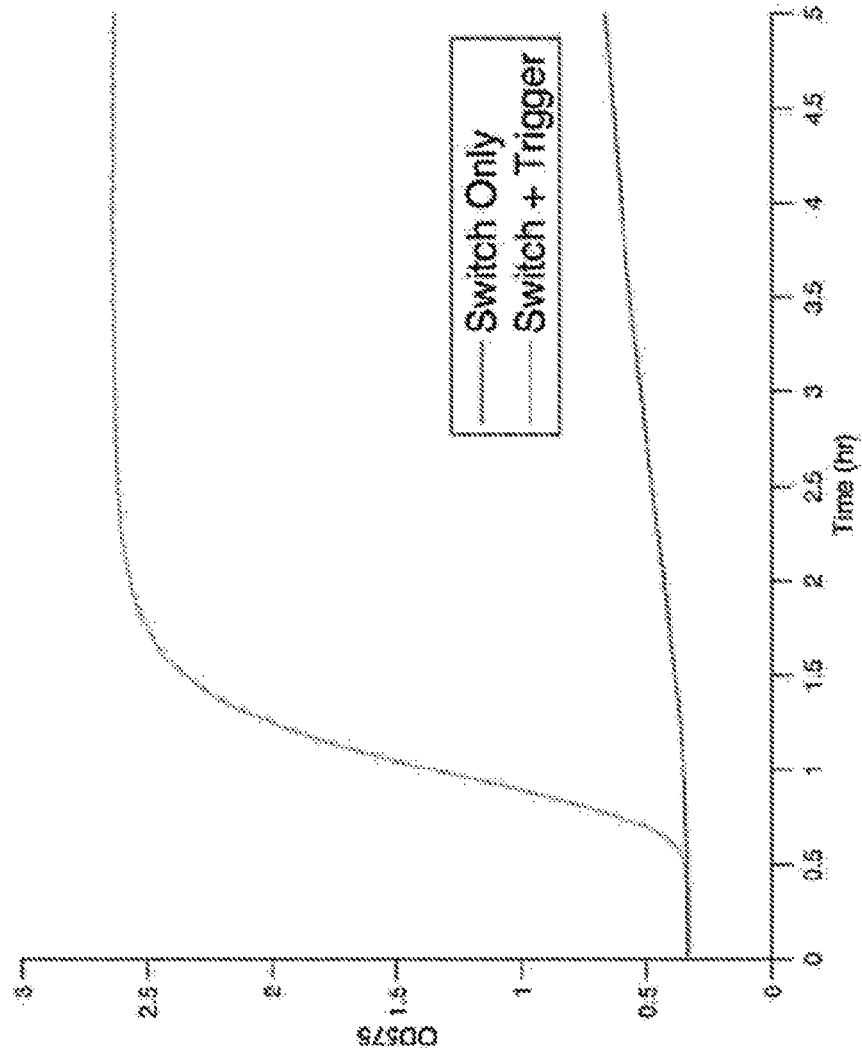
Figure 6A-D (Continued)

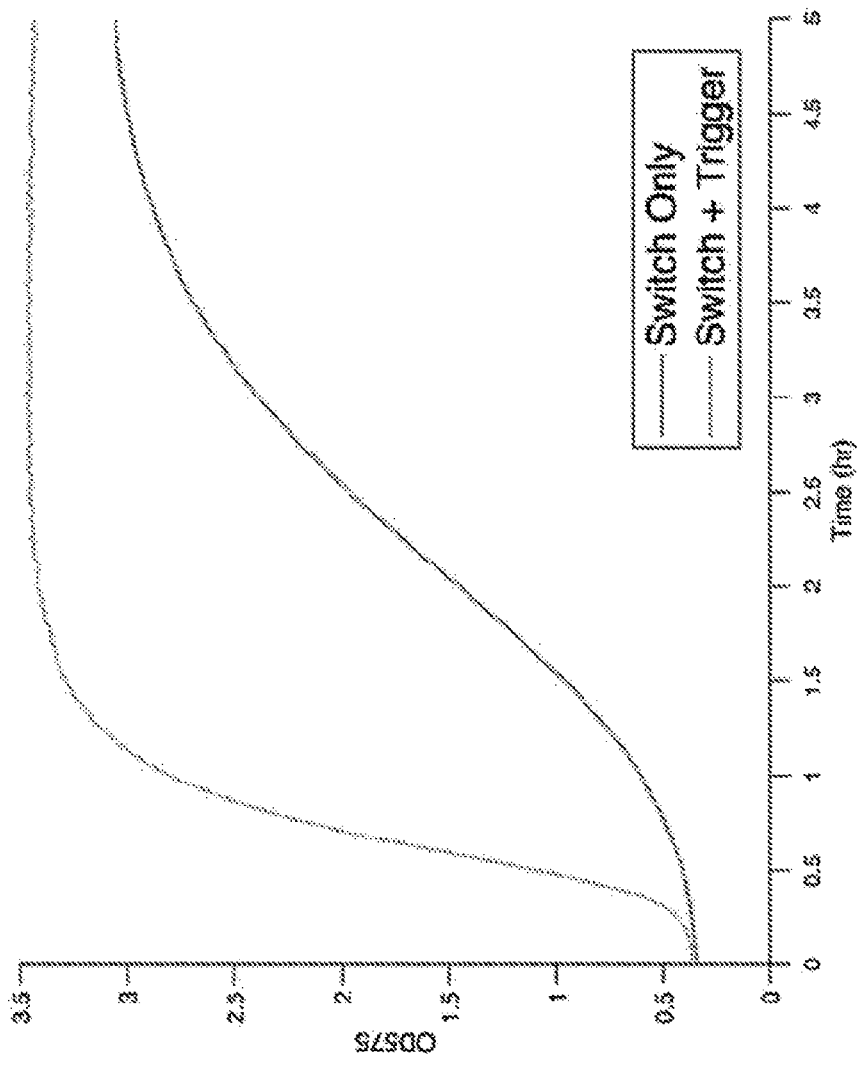
Figure 6A-D (Continued)

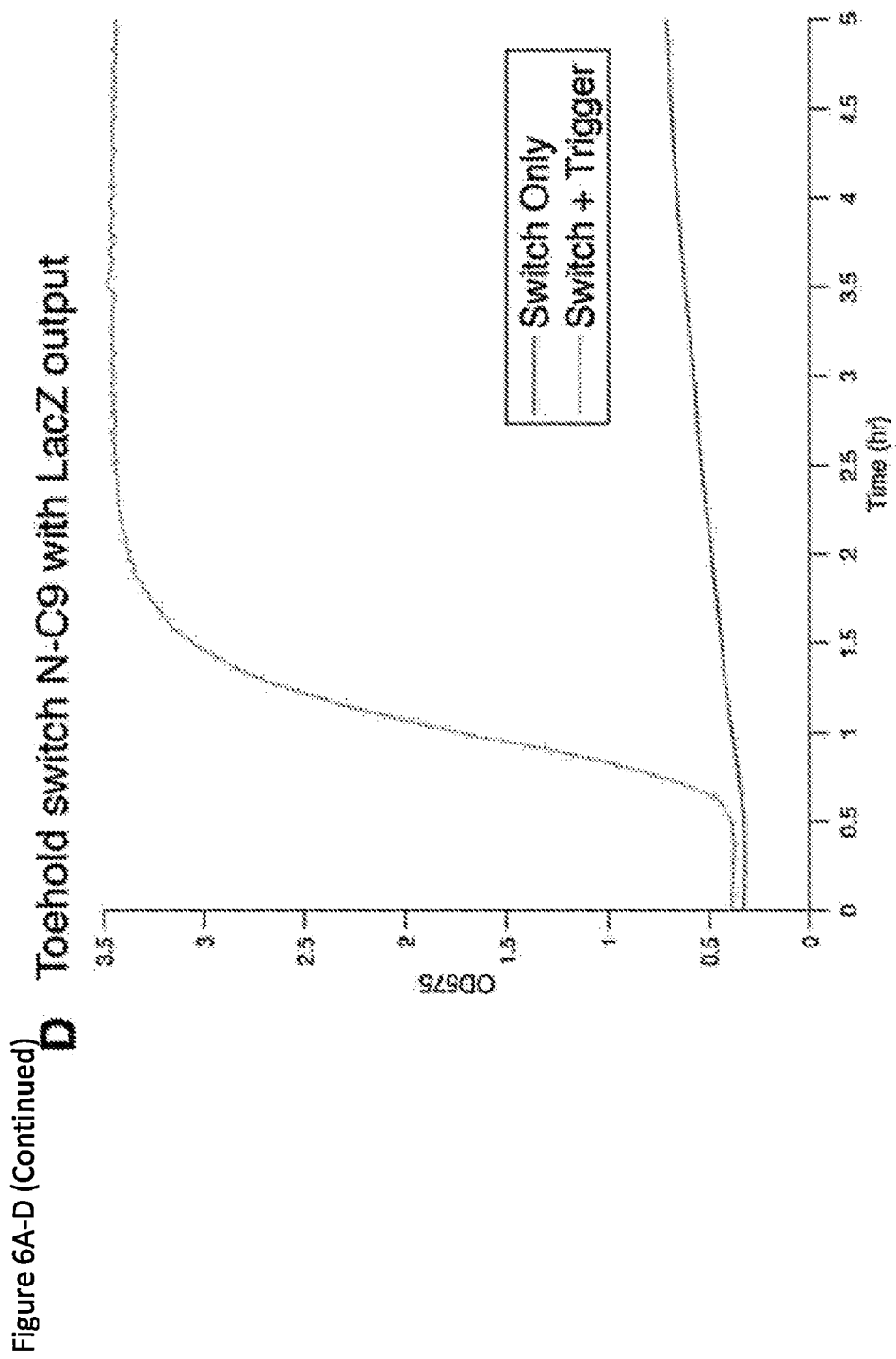
Figure 6A-D (Continued)

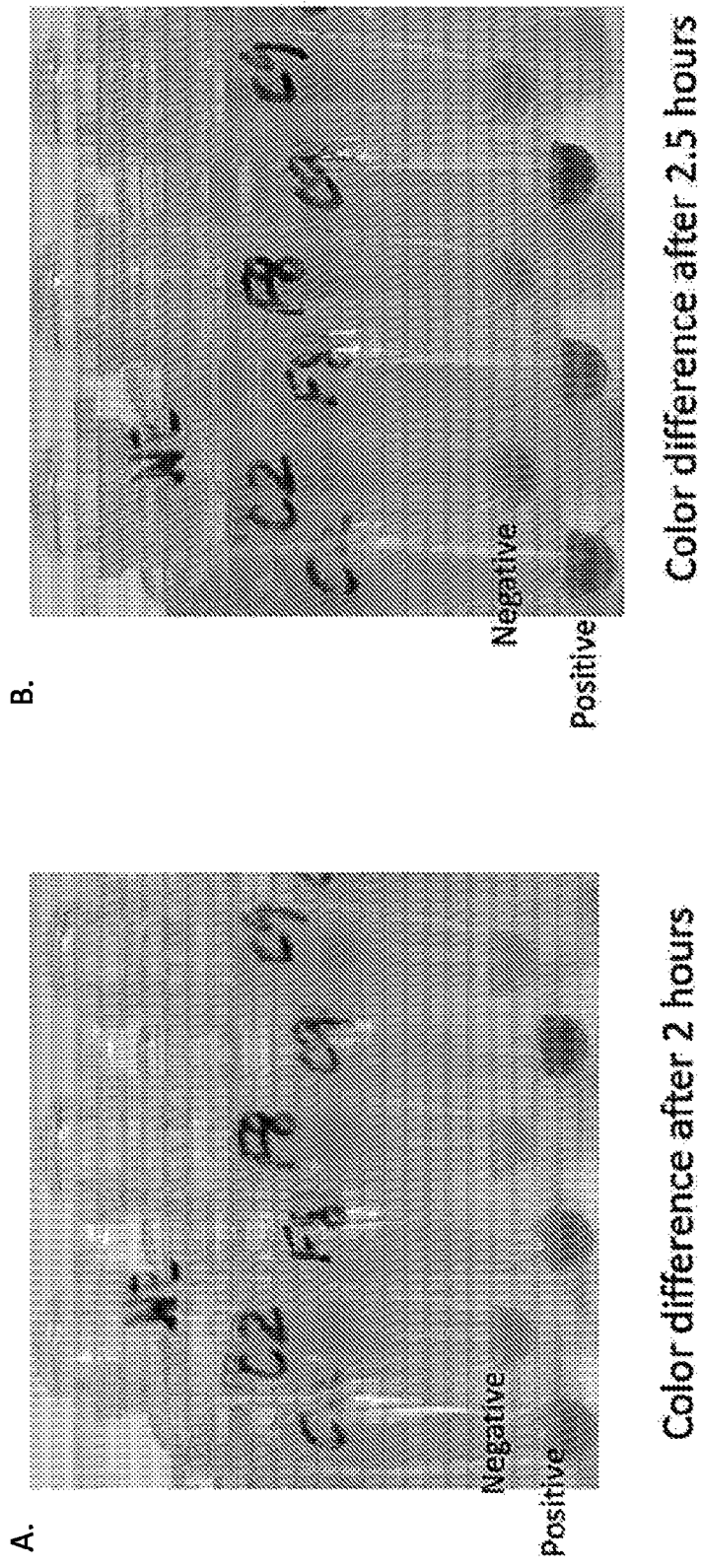
Figure 7A-B

Figure 8A-B
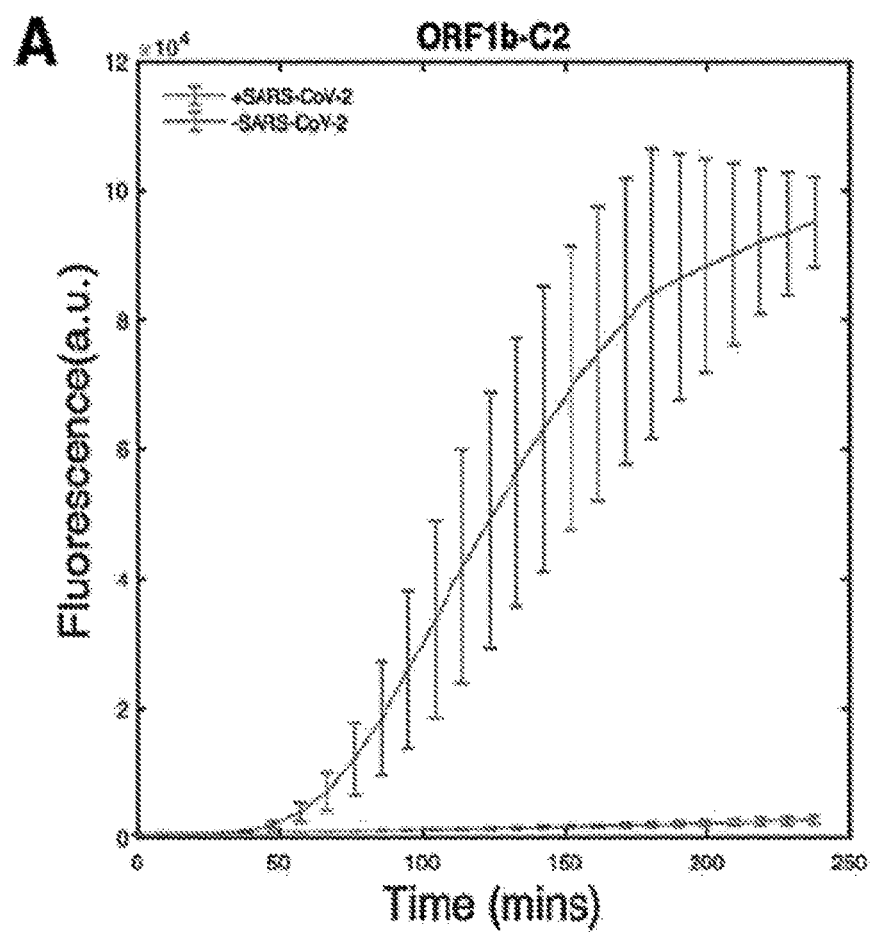

Figure 8A-B (Continued)
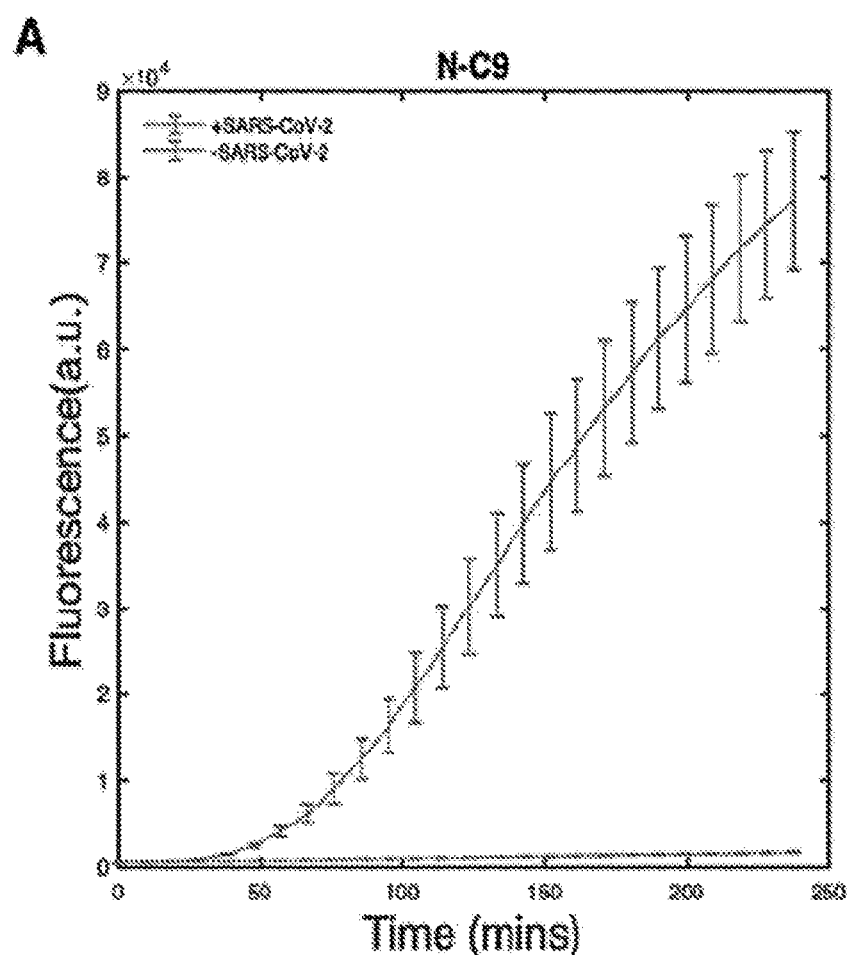

Figure 8A-B (Continued)
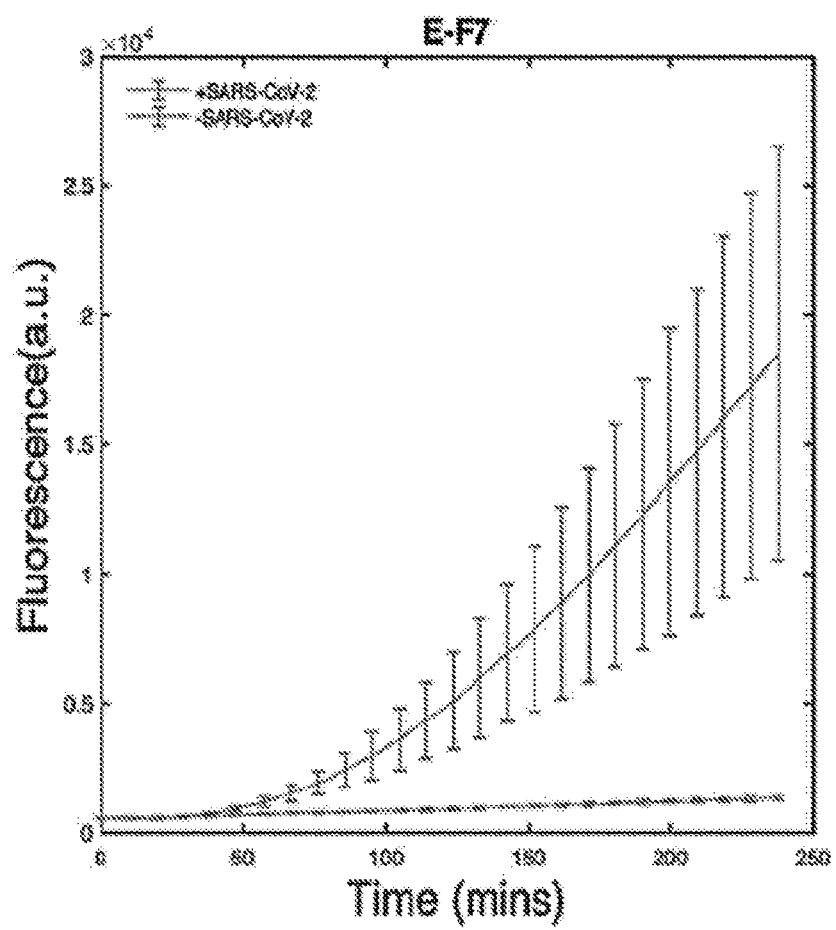

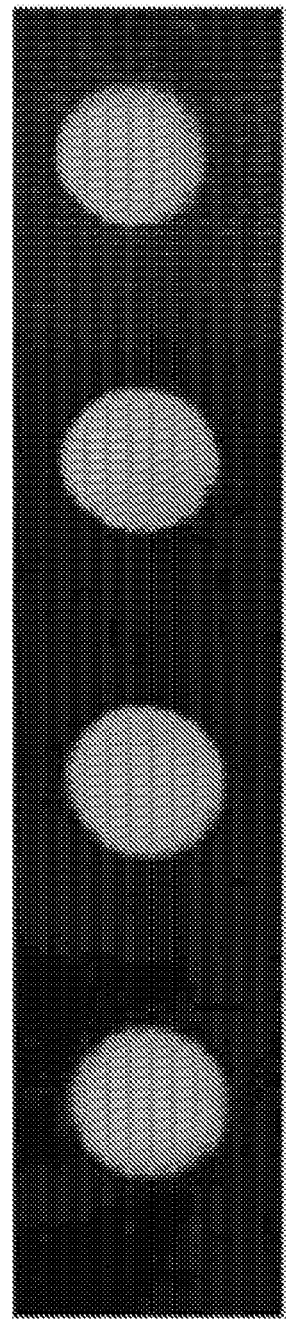
Figure 8A-B (Continued)

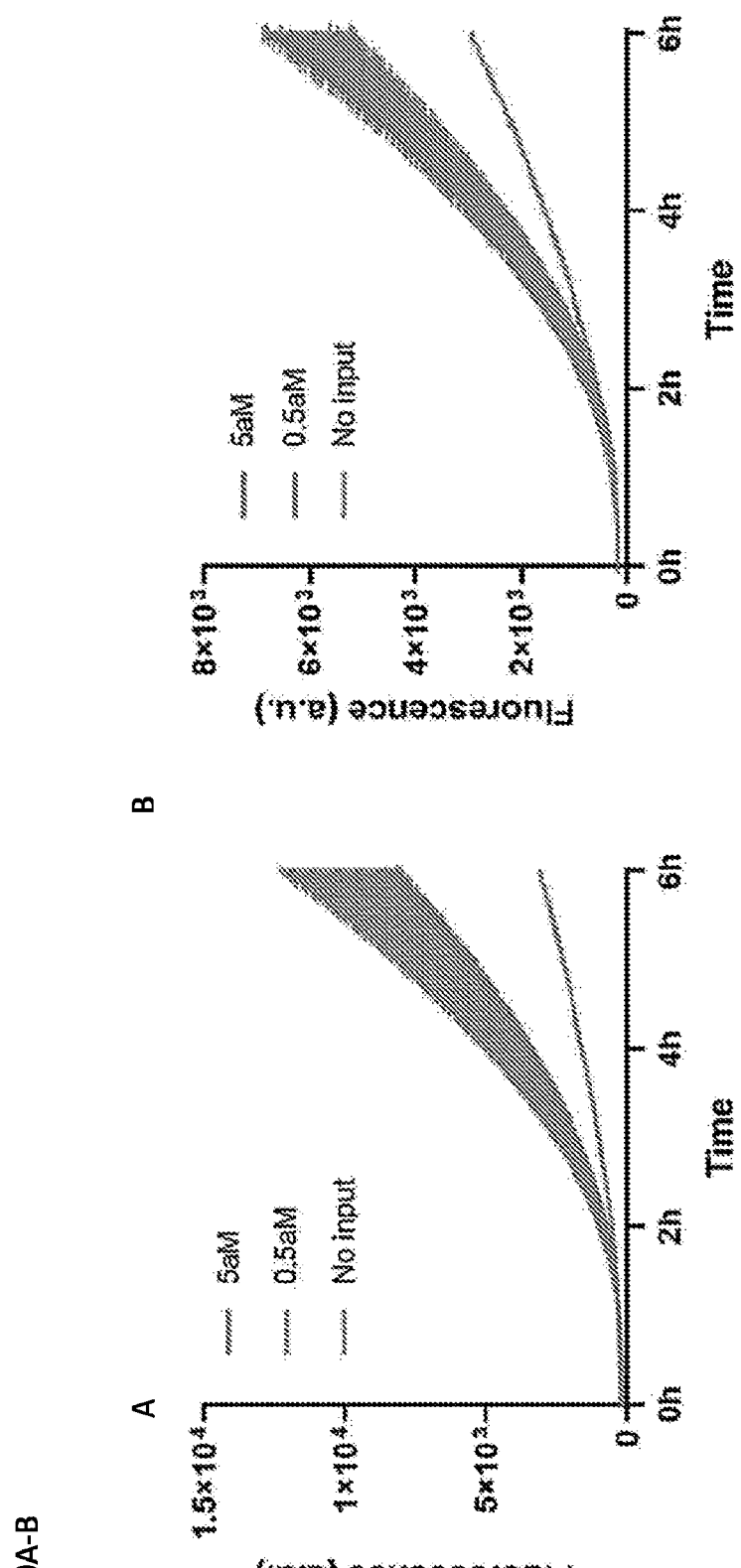
Figure 10A-B

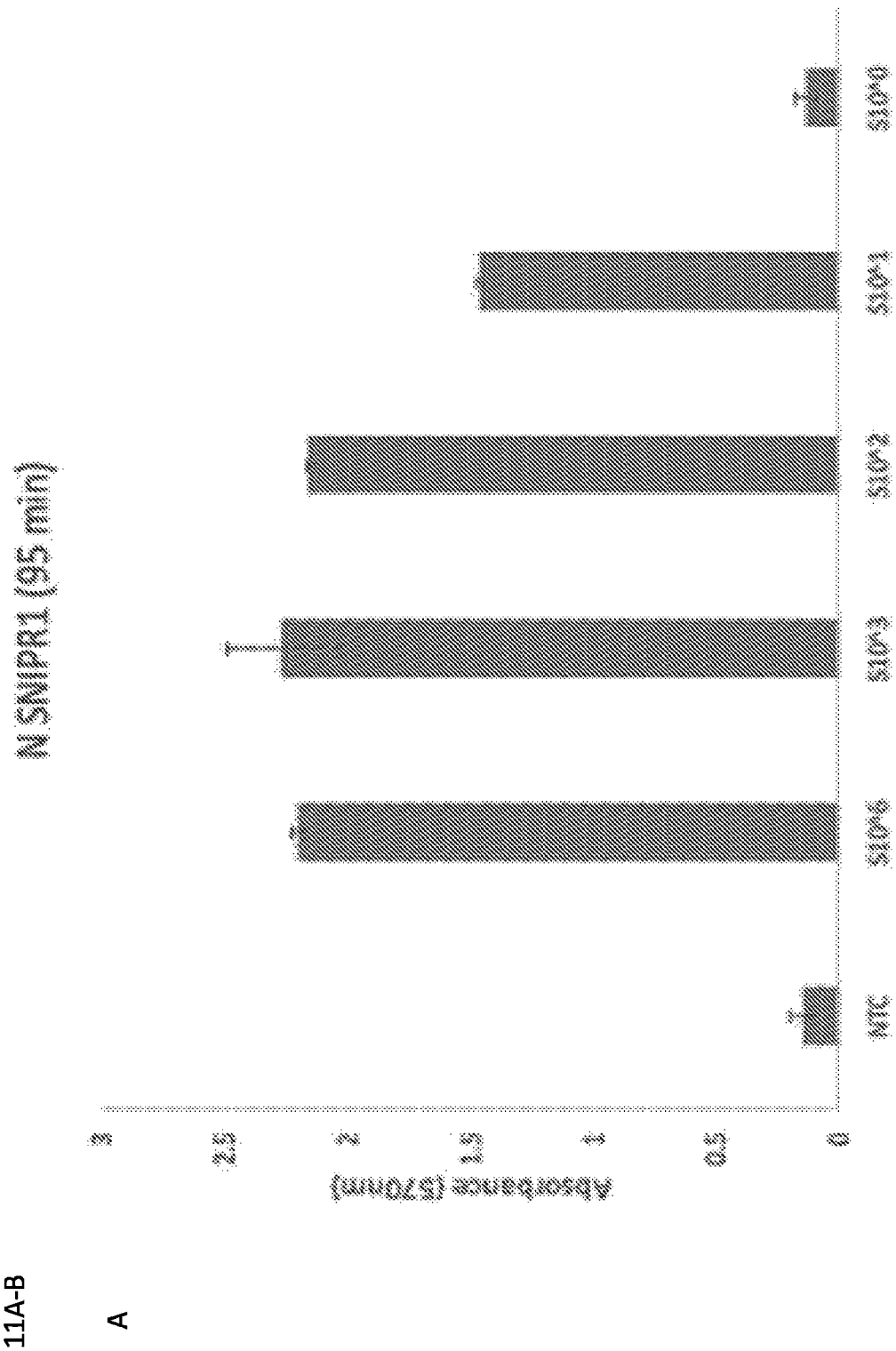
Figure 11A-B

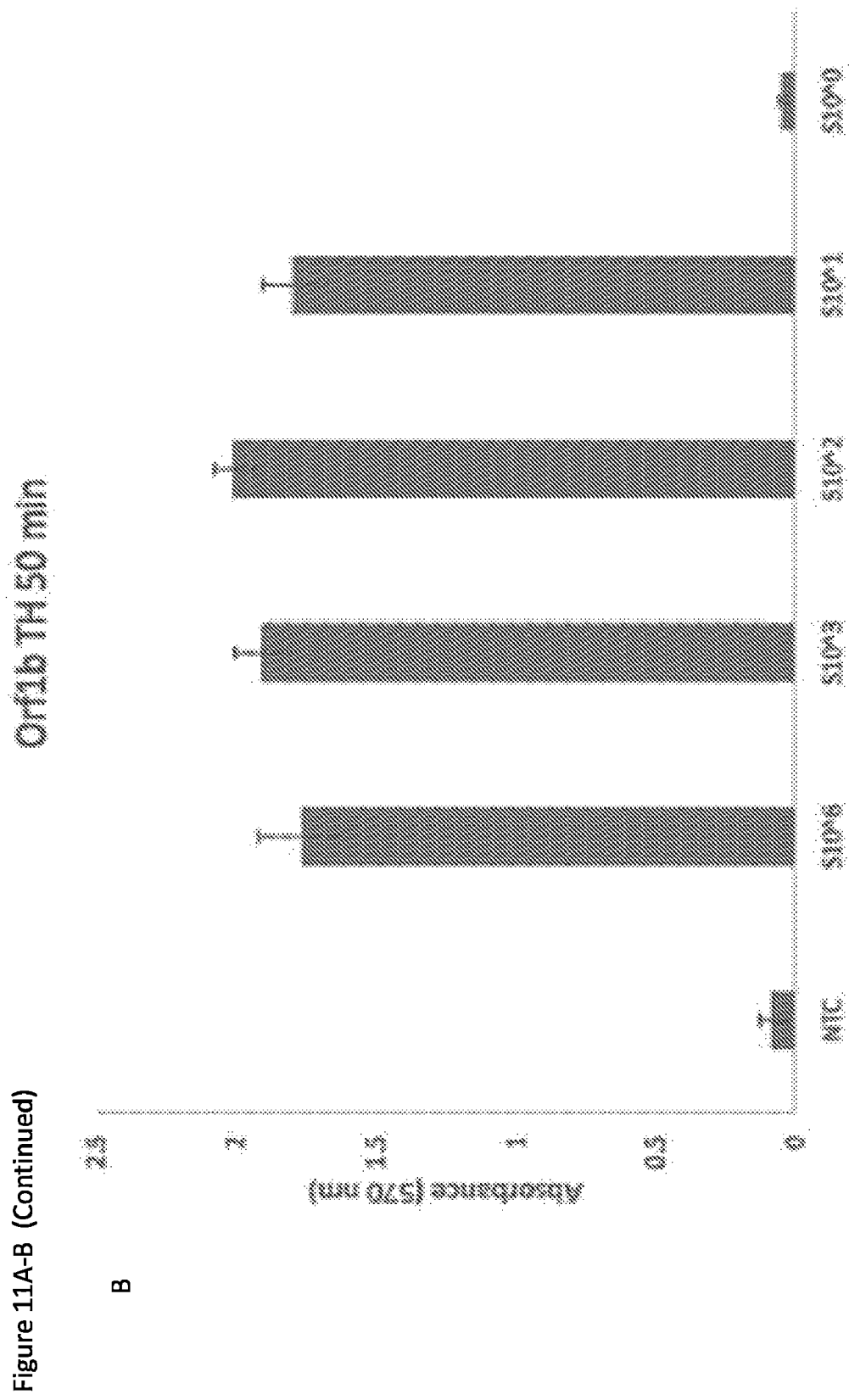
Figure 11A-B (Continued)

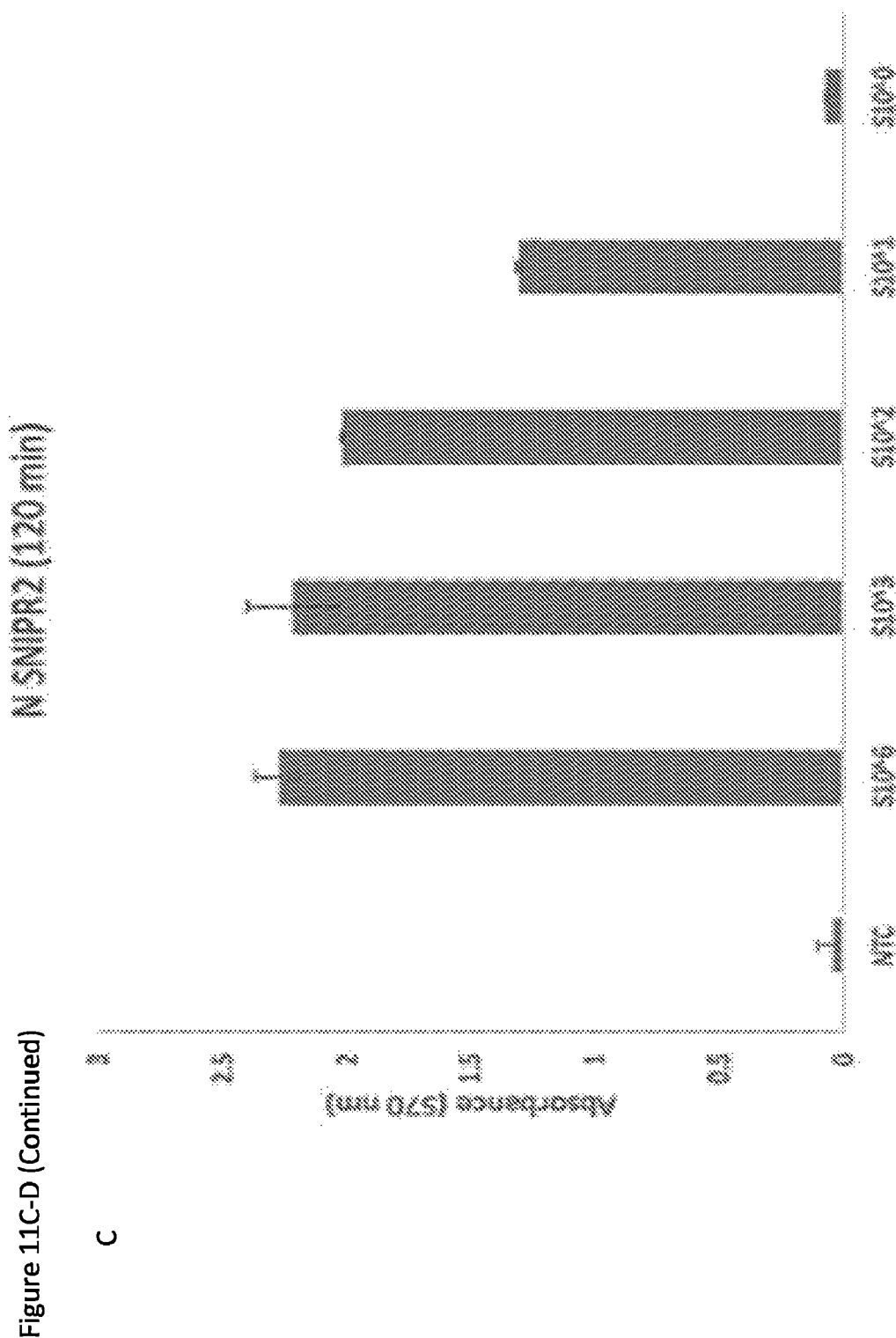
Figure 11C-D (Continued)

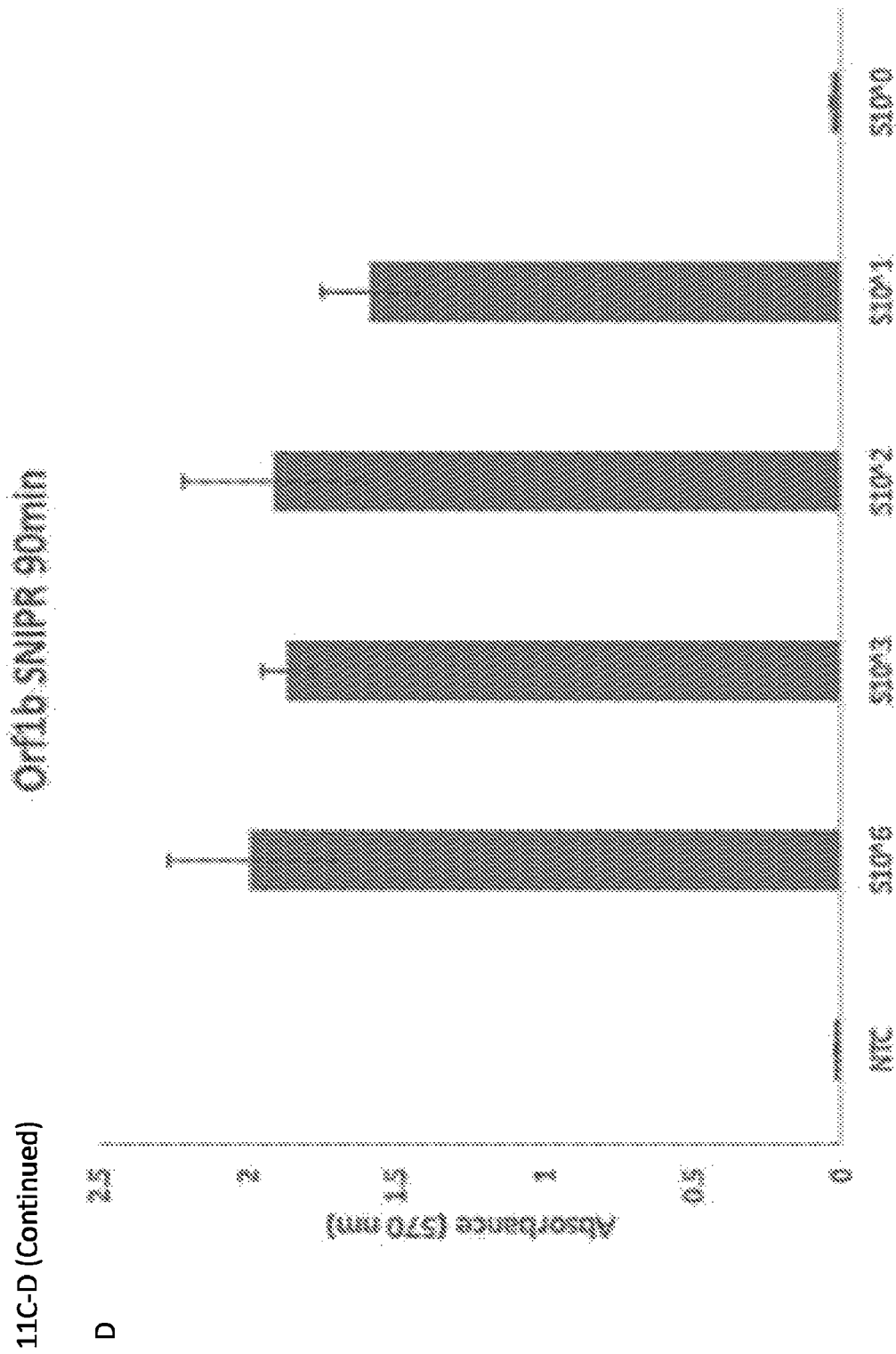
Figure 11C-D (Continued)

Figure 12

TABLE 1: Primer Sequences

| SEQ ID NO: | Primer Name | Sequence |
|---|---|---|
| 1 | TS_SARS2_ORF1b_C2_fwd1 | GCGCTAATACGACTCACTATAGGGCGCGCATTAATCTTCAGTTCATCACCAATTA |
| 2 | TS_SARS2_N_C7_fwd1 | GCGCTAATACGACTCACTATAGGGCGCGTCAATATGCTTATTCAGCAAAATGACTTGA |
| 3 | TS_SARS2_N_C7_fwd3 | GCGCTAATACGACTCACTATAGGGTATGCGTCAATATGCTTATTCAGCAAAATGA |
| 4 | TS_SARS2_N_C7_fwd4 | GCGCTAATACGACTCACTATAGGGATGCGTCAATATGCTTATTCAGCAAAATGA |
| 5 | TS_SARS2_N_C7_fwd5 | GCGCTAATACGACTCACTATAGGGTGCGTCAATATGCTTATTCAGCAAAATGACTTGA |
| 6 | TS_SARS2_N_C9_fwd1 | GCGCTAATACGACTCACTATAGGGTTTGTATGCGTCAATATGCTTATTCAGCA |
| 7 | TS_SARS2_N_C9_fwd5 | GCGCTAATACGACTCACTATAGGGTTTGTATGCGTCAATATGCTTATTCAGCAA |
| 8 | TS_SARS2_ORF1b_C2_rev1 | GTTCAACAATGGGGTTTTACAGGTAACCTACA |
| 9 | TS_SARS2_ORF1b_C2_rev2 | GATGTTCAACAATGGGGTTTTACAGGTAACCTACA |
| 10 | TS_SARS2_ORF1b_C2_rev3 | TGTTCAACAATGGGGTTTTACAGGTAACCTACA |
| 11 | TS_SARS2_ORF1b_C2_rev4 | TGATGTTCAACAATGGGGTTTTACAGGTAACCTACA |
| 12 | TS_SARS2_ORF1b_C2_rev6 | ATGTTCAACAATGGGGTTTTACAGGTAACCTACA |
| 13 | TS_SARS2_ORF1b_C6_rev1 | CAACAATGGGGTTTTACAGGTAACCTACAAAGCA |
| 14 | TS_SARS2_ORF1b_C6_rev2 | AACAATGGGGTTTTACAGGTAACCTACAAAGCA |
| 15 | TS_SARS2_ORF1b_C6_rev5 | TCAACAATGGGGTTTTACAGGTAACCTACAAAGCA |
| 16 | TS_SARS2_N_C7_rev1 | GACAAGGAACTGATTACAAACATTGGCCGCA |
| 17 | TS_SARS2_N_C7_rev2 | CAGACAAGGAACTGATTACAAACATTGGCCGCA |
| 18 | TS_SARS2_N_C7_rev3 | CAAGGAACTGATTACAAACATTGGCCGCAA |
| 19 | TS_SARS2_N_C9_rev1 | GATTACAAACATTGGCCGCAAATTGCACA |
| 20 | TS_SARS2_N_C9_rev2 | GGAACTGATTACAAACATTGGCCGCAAATTGCACA |
| 21 | TS_SARS2_N_C9_rev4 | AGGAACTGATTACAAACATTGGCCGCAAATTGCACA |
| 22 | TS2_SARS2_E_F7_fwd1 | GCGCTAATACGACTCACTATAGGGCAGAAGATCAGGAACTCTAGAAGAATTCAGA |
| 23 | TS2_SARS2_E_F7_fwd2 | GCGCTAATACGACTCACTATAGGGAGAAGATCAGGAACTCTAGAAGAATTCAGA |
| 24 | TS2_SARS2_E_F7_rev1 | GAGACAGGTACGTTAATAGTTAATAGCGTA |
| 25 | TS2_SARS2_E_F7_rev2 | AGAGACAGGTACGTTAATAGTTAATAGCGTA |

Table 2: PRIMER PAIRS

| Primer Pair Name | Forward Primer Name | Reverse Primer Name |
|---|---|---|
| TS_SARS2_ORF1b_C2_primer_pair1 | TS_SARS2_ORF1b_C2_fwd1 | TS_SARS2_ORF1b_C2_rev1 |
| TS_SARS2_ORF1b_C2_primer_pair2 | TS_SARS2_ORF1b_C2_fwd1 | TS_SARS2_ORF1b_C2_rev2 |
| TS_SARS2_ORF1b_C2_primer_pair3 | TS_SARS2_ORF1b_C2_fwd1 | TS_SARS2_ORF1b_C2_rev3 |
| TS_SARS2_ORF1b_C2_primer_pair4 | TS_SARS2_ORF1b_C2_fwd1 | TS_SARS2_ORF1b_C2_rev4 |
| TS_SARS2_ORF1b_C2_primer_pair6 | TS_SARS2_ORF1b_C2_fwd1 | TS_SARS2_ORF1b_C2_rev6 |
| TS_SARS2_ORF1b_C6_primer_pair1 | TS_SARS2_ORF1b_C2_fwd1 | TS_SARS2_ORF1b_C6_rev1 |
| TS_SARS2_ORF1b_C6_primer_pair2 | TS_SARS2_ORF1b_C2_fwd1 | TS_SARS2_ORF1b_C6_rev2 |
| TS_SARS2_ORF1b_C6_primer_pair5 | TS_SARS2_ORF1b_C2_fwd1 | TS_SARS2_ORF1b_C6_rev5 |
| TS_SARS2_N_C7_primer_pair1 | TS_SARS2_N_C7_fwd1 | TS_SARS2_N_C7_rev1 |
| TS_SARS2_N_C7_primer_pair2 | TS_SARS2_N_C7_fwd1 | TS_SARS2_N_C7_rev2 |
| TS_SARS2_N_C7_primer_pair3 | TS_SARS2_N_C7_fwd3 | TS_SARS2_N_C7_rev3 |
| TS_SARS2_N_C7_primer_pair4 | TS_SARS2_N_C7_fwd4 | TS_SARS2_N_C7_rev1 |
| TS_SARS2_N_C7_primer_pair5 | TS_SARS2_N_C7_fwd5 | TS_SARS2_N_C7_rev1 |
| TS_SARS2_N_C7_primer_pair6 | TS_SARS2_N_C7_fwd1 | TS_SARS2_N_C7_rev3 |
| TS_SARS2_N_C9_primer_pair1 | TS_SARS2_N_C9_fwd1 | TS_SARS2_N_C9_rev1 |
| TS_SARS2_N_C9_primer_pair2 | TS_SARS2_N_C7_fwd3 | TS_SARS2_N_C9_rev2 |
| TS_SARS2_N_C9_primer_pair3 | TS_SARS2_N_C9_fwd1 | TS_SARS2_N_C9_rev1 |
| TS_SARS2_N_C9_primer_pair4 | TS_SARS2_N_C7_fwd3 | TS_SARS2_N_C9_rev4 |
| TS_SARS2_N_C9_primer_pair5 | TS_SARS2_N_C9_fwd5 | TS_SARS2_N_C9_rev1 |
| TS_SARS2_N_C9_primer_pair6 | TS_SARS2_N_C7_fwd3 | TS_SARS2_N_C7_rev3 |
| TS2_SARS2_E_F7_primer_pair1 | TS2_SARS2_E_F7_fwd1 | TS2_SARS2_E_F7_rev1 |
| TS2_SARS2_E_F7_primer_pair2 | TS2_SARS2_E_F7_fwd2 | TS2_SARS2_E_F7_rev1 |
| TS2_SARS2_E_F7_primer_pair3 | TS2_SARS2_E_F7_fwd2 | TS2_SARS2_E_F7_rev2 |

TABLE 3: SENSOR SEQUENCES

| SEQ ID NO: | Sensor Name | Sensor Sequence |
|---|---|---|
| 26 | TS_SARS2_ORF1b_C1 | GGGUUGUCAAGUCCAUGGUAAUGCACAUGUAGCUAGUUGGGUUAUAGUUAUGAACAGA |
| 27 | TS_SARS2_ORF1b_C2 | GGAGACAUAACAUGAACCAACUAAACUAAACUUGGGUUAACCUGGCGGCAGCGCAAAAG GGGAGCAACCAUGAUCUGUAUUGUCAAGUCCAUGGUAAUGUUAUAGUUAUGAACAGAG |
| 28 | TS_SARS2_ORF1b_C3 | GGAGACAUAACAUGAACAUGAACAUUACCAACAAUGU Figure 14 (Continued)

| | | |
|---|---|---|
| 40 | TS_SARS2_RdRP_D3 | GGGACUAUAUGGUUAAACCAGGUGGAACCUCAUCAGGAGAGUUAUGAUUAUGAACAGAG GAGACAUAAACAUGAACUCCUAACAGAGUUAACCUGGCCAGGCGCAAAAG |
| 41 | TS_SARS2_RdRP_D4 | GGGUAUGGUUAAACCAGGUGGAACUCUAACAGAGUUAACCGUUAUAGUUAUGAACAGAG GAGACAUAAACAUGAACGGCAUCAACGCCGUUAACCUGGCGCAGCGCAAAAG |
| 42 | TS_SARS2_RdRP_D5 | GGGUUCACUAUAUGGUUAAACCAGGUGGAACCUCACAGGGUUAUAGUUAUGAACAGAG GAGACAUAACAUGAACCUGAUAACAGGGUUAACCUGGCGGCAGCGCAAAAG |
| 43 | TS_SARS2_RdRP_D6 | GGGAUAUGUUAAACCAGGUGGAACCUCACAGGAGAUGGUUAUAGUUAUGAACAGAG GAGACAUAACAUGAACGCAUCUAACGCGUUAACCUGGCGCAGCGCAAAAG |
| 44 | TS_SARS2_E_D7 | GGGUCUUUUCUUCGUCUUCGUGUGGUAUUCUUGCUAGUAGUUAGUUAUGAACAGA GGAGACAUAACAUGAACGUAACAACUACGUUAACCUGGCGGCAGCGCAAAG |
| 45 | TS_SARS2_E_D8 | GGGCUUUCGUGUGGUAUUCUUGCUAGUUAGUUACGCCAUCCGUUAUAGUUAUGAACAGAG GAGACAUAACAUGGAACGGAACUCGUUAACCGUAUCCUGGCGGCAGCGCAAAAG |
| 46 | TS_SARS2_E_D9 | GGGUUUUCUUGCUUUCGUGUGGUAUUCUUGCUAGUAGUUAACACCUGGCGCAGCGCAAAAG GGAGACAUAACAUGAACAGUUAACAACUGUAACCUGGCGGCAGCGCAAAAG |
| 47 | TS_SARS2_E_D10 | GGGUUUCGUGUGGUAUUCUUGCUAGUUAGUUCUGCCAUCCUGUUAUAGUUAUGAACAGAG GAGACAUAACAUGAACAGGAUGAACUGUAACCUGUAAGUUACAGCUGGCGGCAGCGCAAAAG |
| 48 | TS_SARS2_E_D11 | GGGCUUUUCUUGCUUUCGUGGUAUUCUUGCUAGUACACAGUUAGUUAUGAACAGAG GAGACAUAACAUGAACAACACGUCUAGUUACACUGUAACCUGGCGGCAGCGCAAAAG |
| 49 | TS_SARS2_E_D12 | GGGUUGCUUUCGUGUAACAUGACUGUAACCCAGUCUAACUAGCCAGUUAUAGUUAUGAACAGAG GAGACAUAACAUGAACUGCUAACGGCUAACCUGGCGGCAGCGCAAAAG |
| 50 | TS2_SARS2_E_F7 | GGGGCGUGGUAAUCUUGCUAGUUAUGUUACUAGCCAUCCUUACGACCUUUAGAACAGAGGAC AUAAAGAUGUAAGGUAAGGAUGGCAAACCUGGCGCAGCGCAAAAG |
| 51 | TS2_SARS2_E_F8 | GGGUAUGGUAAUCUUGCUAGUUAUGUUACUAGCCAUCCUUACUGGACUUUAGAACAGAGGAG AUAAAGAUGAAUGAGAGUAAGGAUGGCAACCUGGGCGCAGCGCAAAAG |
| 52 | EAR_H22_2019_nCoV_Rd RP_sensF | GGGUCUCCUGAUGAGGAGUUCCACCUGGGUUUAACAUAUAGUGGACUUUAGAACAGAGGA GAUAAAGAUGACUAAUGGUUACAACCUGGCGGCAGCGCAAAAG |

Figure 14 (Continued)

| | | |
|---|---|---|
| 53 | Orf1b SNIPR = SNIPR_2019_nCoV_ORF1b_pos2_N6 | GGGCGUGGACAGCUAGACACCUAGUCAUGAUUGCACUUGUGCUAGCUACAUGUGCAUUACCAUUAGCACUAGAGGAGACCCGAGAUGGCUAAUGGUAAUGCACAUGUACAUUCCAACCAACAACUGCGGAUGACCAUGAUUACGGAUUCACUGG |
| 54 | Orf1b TH = TSgen2_2019_nCoV_ORF1b_sensA | GGGCAUCACAACUAGCUACAUGUGCAUUACCAUGGACUGUUAUAGUUAUGAACAGAGGAGACAUAACAUGAACAGUCCAAACACUGUUAACCUGGCGGCAGCGCAAAAG |
| 55 | N SNIPR1 = SNIPR_2019_nCoV_N_N2 | GGGUGUGACUUCCAUGCCAAUGCGCGACAUUUGCGAAAGAGCUGAAGCGCUGGGGGCAAAUUUGCAUAAAGAGGAGAUUAGAAAUGUGCAAAUUUGCCCCCAGCGCUUCGCAUAACUCAUAUCGGUCCAUGACCAUGAUUACGGAUUCACUGG |
| 56 | N SNIPR 2 = SNIPR_2019_nCoV_N_N6 | GGGUGUGACUUCCAUGCCAAUGCGCGACAUUCUGAUGGGAGCUGAAGCGCUGGGGGCAAAUUUGCAUACAGAGGAGAUCACAGAUGUGCAAAUUUGCCCCCAGCGCUCAAUCUGGCAUGUGUCAUGGCAUGACCAUGAUUACGGAUUCACUGG |

Figure 18A-B
A.
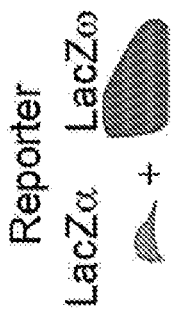
B.
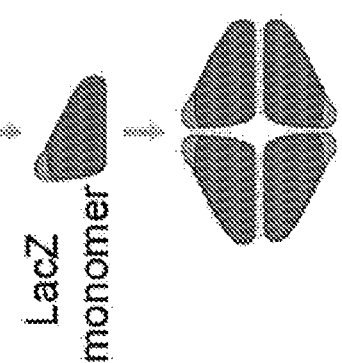

Figure 19A-B
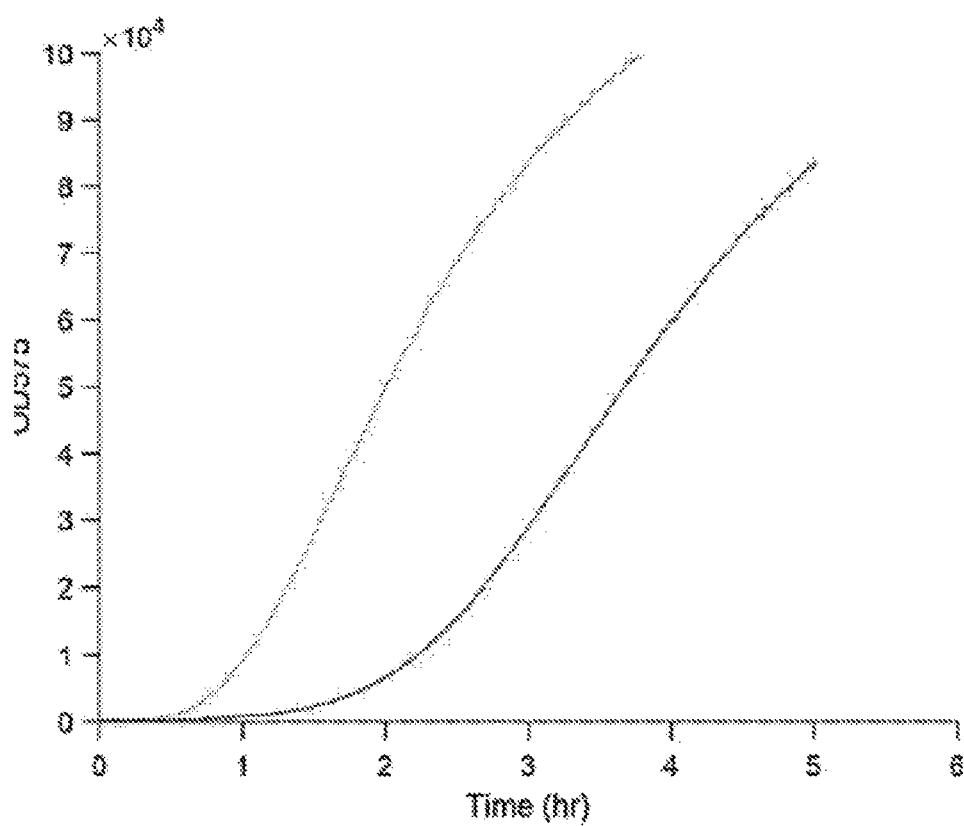

Figure 19A-B (Continued)
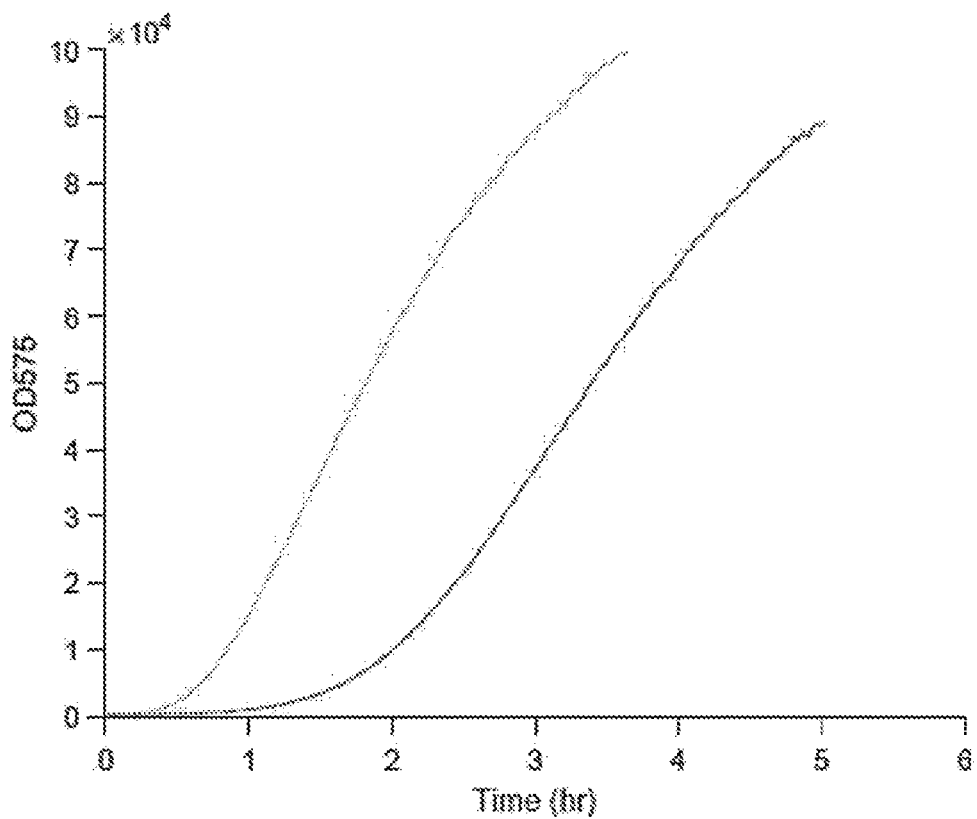

Figure 19C-D
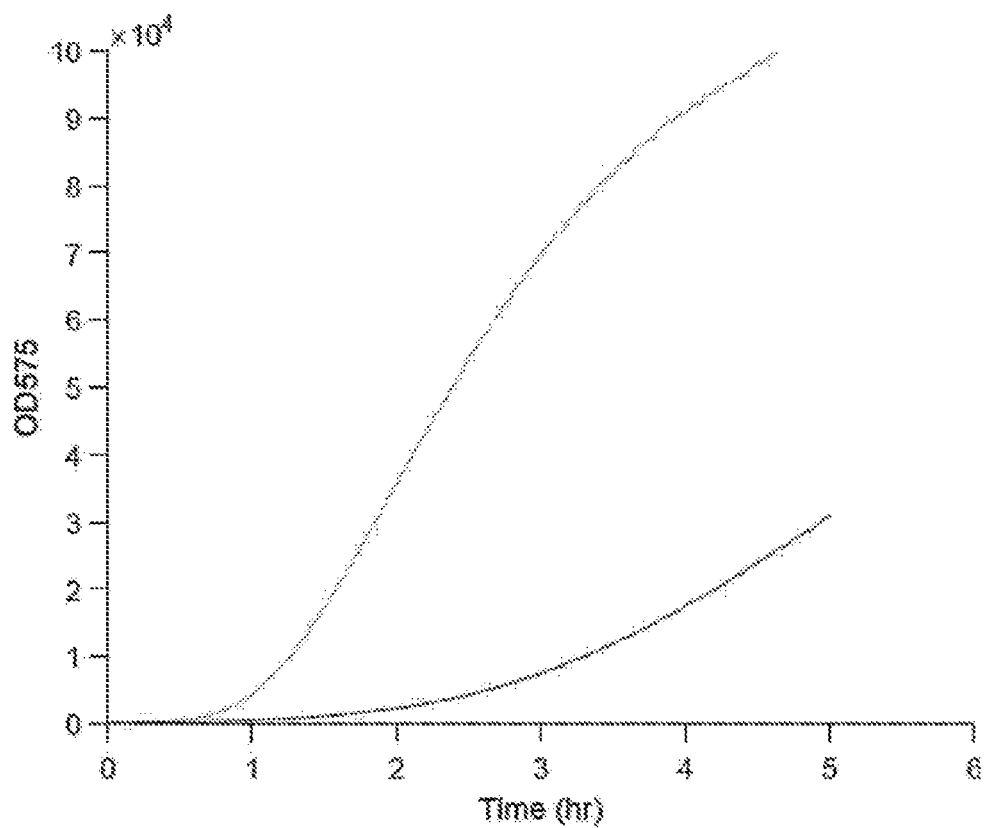

Figure 19C-D (Continued)
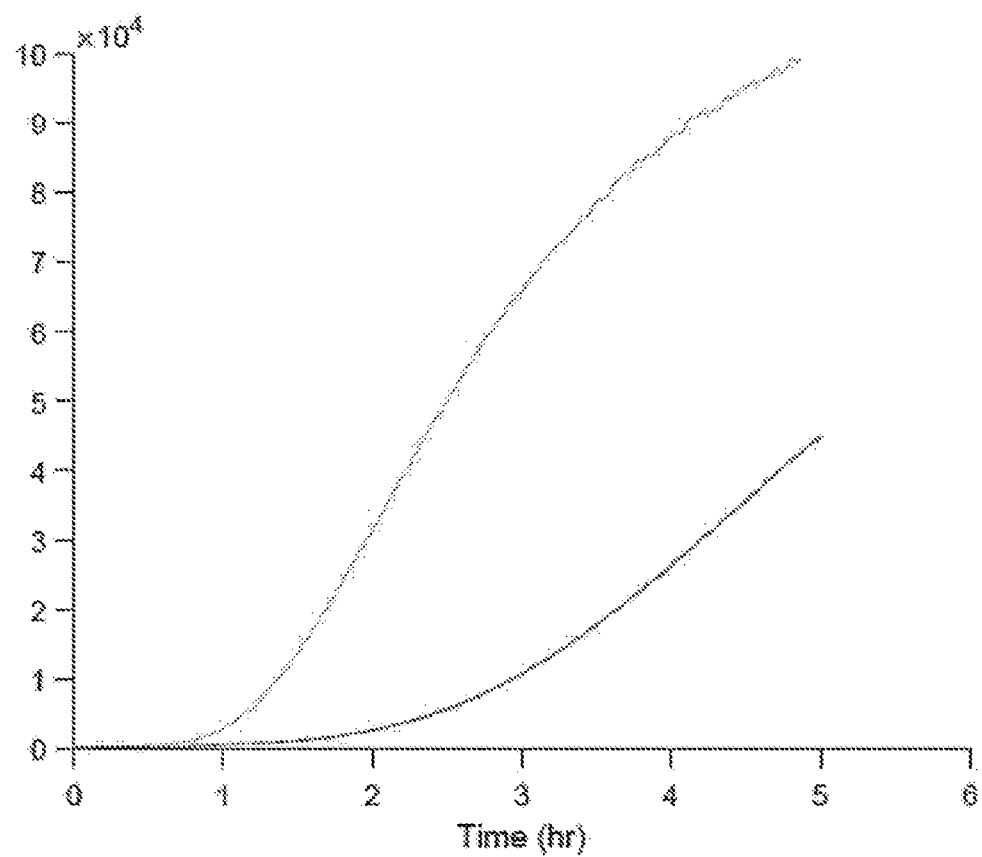

Figure 20

| Name | Volume |
|---|---|
| WarmStart LAMP 2x Master Mix | 15 µl |
| 10X RT-LAMP primer mix | 3 µl |
| Target RNA/dH2O | 12 µl |
| Total | 30 µl |

Straight addition to cell-free →

| Name | Volume |
|---|---|
| PURExpress A | 2 µl |
| PURExpress B | 1.5 µl |
| RNase inhibitor | 0.1 µl |
| FDG(10mg/mL) | 0.1 µl |
| LAMP products | 1 µl |
| lacZ-omega | 0.1 µl |
| LAMP toehold switch | 0.5 µL(3nM) |

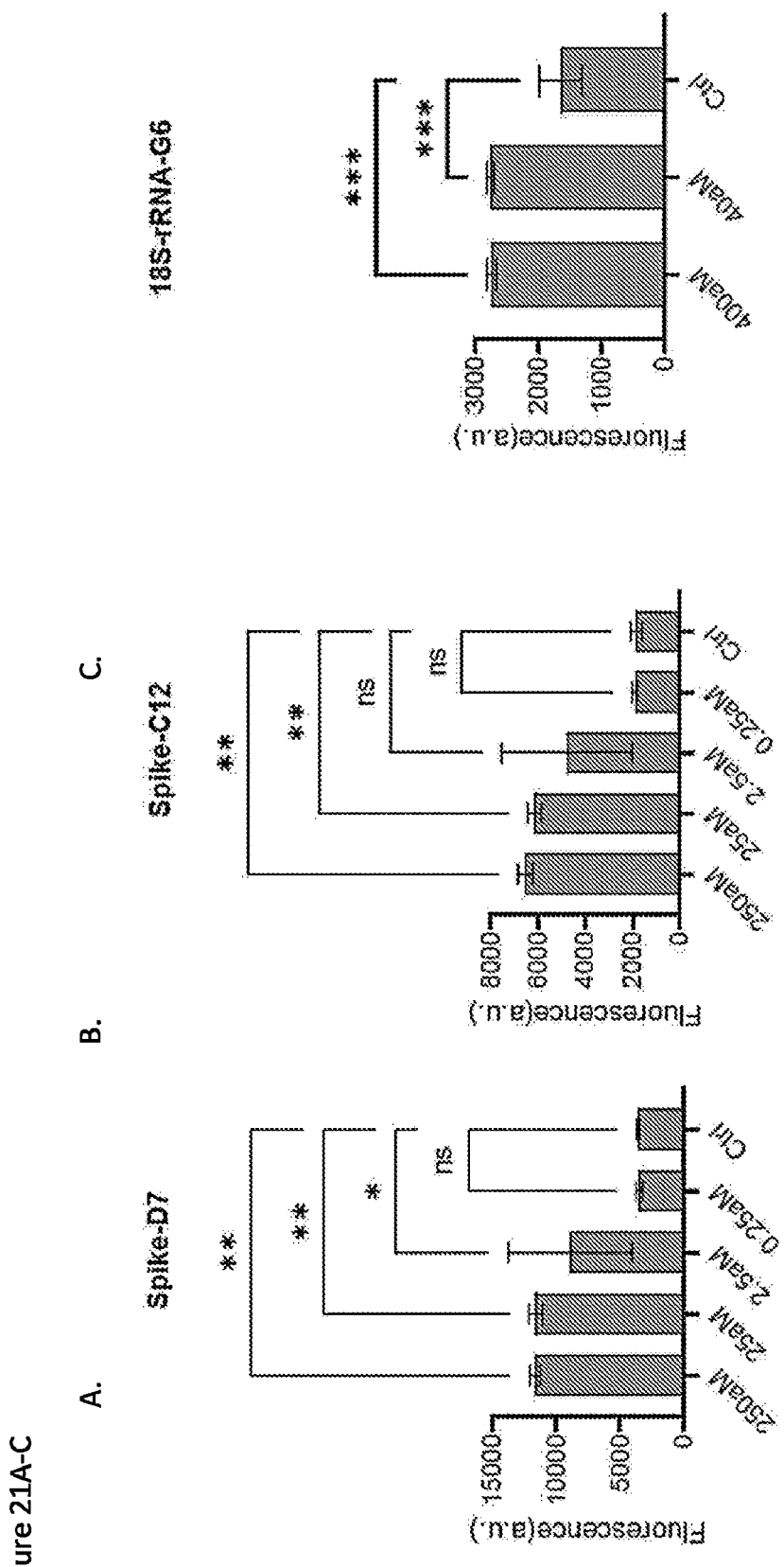
Figure 21A-C

SEQUENCE LISTING

```
<160> NUMBER OF SEQ ID NOS: 78

<210> SEQ ID NO 1
<211> LENGTH: 54
<212> TYPE: DNA
<213> ORGANISM: Artificial Sequence
<220> FEATURE:
<223> OTHER INFORMATION: Synthetic- TS_SARS2_ORF1b_C2_fwd1

<400> SEQUENCE: 1
gcgctaatac gactcactat agggccgcat taatcttcag ttcatcacca atta         54

<210> SEQ ID NO 2
<211> LENGTH: 56
<212> TYPE: DNA
<213> ORGANISM: Artificial Sequence
<220> FEATURE:
<223> OTHER INFORMATION: Synthetic- TS_SARS2_N_C7_fwd1

<400> SEQUENCE: 2
gcgctaatac gactcactat agggcgtcaa tatgcttatt cagcaaaatg acttga       56

<210> SEQ ID NO 3
<211> LENGTH: 55
<212> TYPE: DNA
<213> ORGANISM: Artificial Sequence
<220> FEATURE:
<223> OTHER INFORMATION: Synthetic- TS_SARS2_N_C7_fwd3

<400> SEQUENCE: 3
gcgctaatac gactcactat agggtatgcg tcaatatgct tattcagcaa aatga        55

<210> SEQ ID NO 4
<211> LENGTH: 54
<212> TYPE: DNA
<213> ORGANISM: Artificial Sequence
<220> FEATURE:
<223> OTHER INFORMATION: Synthetic- TS_SARS2_N_C7_fwd4

<400> SEQUENCE: 4
gcgctaatac gactcactat agggatgcgt caatatgctt attcagcaaa atga         54

<210> SEQ ID NO 5
<211> LENGTH: 58
<212> TYPE: DNA
<213> ORGANISM: Artificial Sequence
<220> FEATURE:
<223> OTHER INFORMATION: Synthetic- TS_SARS2_N_C7_fwd5

<400> SEQUENCE: 5
gcgctaatac gactcactat agggtgcgtc aatatgctta ttcagcaaaa tgacttga     58

<210> SEQ ID NO 6
<211> LENGTH: 54
<212> TYPE: DNA
<213> ORGANISM: Artificial Sequence
<220> FEATURE:
```

<223> OTHER INFORMATION: Synthetic- TS_SARS2_N_C9_fwd1

<400> SEQUENCE: 6
gcgctaatac gactcactat agggttttgt atgcgtcaat atgcttattc agca        54

<210> SEQ ID NO 7
<211> LENGTH: 54
<212> TYPE: DNA
<213> ORGANISM: Artificial Sequence
<220> FEATURE:
<223> OTHER INFORMATION: Synthetic- TS_SARS2_N_C9_fwd5

<400> SEQUENCE: 7
gcgctaatac gactcactat agggtttgta tgcgtcaata tgcttattca gcaa        54

<210> SEQ ID NO 8
<211> LENGTH: 32
<212> TYPE: DNA
<213> ORGANISM: Artificial Sequence
<220> FEATURE:
<223> OTHER INFORMATION: Synthetic- TS_SARS2_ORF1b_C2_rev1

<400> SEQUENCE: 8
gttcaacaat ggggttttac aggtaaccta ca                                32

<210> SEQ ID NO 9
<211> LENGTH: 35
<212> TYPE: DNA
<213> ORGANISM: Artificial Sequence
<220> FEATURE:
<223> OTHER INFORMATION: Synthetic- TS_SARS2_ORF1b_C2_rev2

<400> SEQUENCE: 9
gatgttcaac aatggggttt tacaggtaac ctaca                             35

<210> SEQ ID NO 10
<211> LENGTH: 33
<212> TYPE: DNA
<213> ORGANISM: Artificial Sequence
<220> FEATURE:
<223> OTHER INFORMATION: Synthetic- TS_SARS2_ORF1b_C2_rev3

<400> SEQUENCE: 10
tgttcaacaa tggggtttta caggtaacct aca                               33

<210> SEQ ID NO 11
<211> LENGTH: 36
<212> TYPE: DNA
<213> ORGANISM: Artificial Sequence
<220> FEATURE:
<223> OTHER INFORMATION: Synthetic- TS_SARS2_ORF1b_C2_rev4

<400> SEQUENCE: 11
tgatgttcaa caatggggtt ttacaggtaa cctaca                            36

<210> SEQ ID NO 12
<211> LENGTH: 34
<212> TYPE: DNA
<213> ORGANISM: Artificial Sequence
<220> FEATURE:
<223> OTHER INFORMATION: Synthetic- TS_SARS2_ORF1b_C2_rev6

<400> SEQUENCE: 12
atgttcaaca atggggtttt acaggtaacc taca                              34

```
<210> SEQ ID NO 13
<211> LENGTH: 34
<212> TYPE: DNA
<213> ORGANISM: Artificial Sequence
<220> FEATURE:
<223> OTHER INFORMATION: Synthetic- TS_SARS2_ORF1b_C6_rev1

<400> SEQUENCE: 13
caacaatggg gttttacagg taacctacaa agca                                34

<210> SEQ ID NO 14
<211> LENGTH: 33
<212> TYPE: DNA
<213> ORGANISM: Artificial Sequence
<220> FEATURE:
<223> OTHER INFORMATION: Synthetic- TS_SARS2_ORF1b_C6_rev2

<400> SEQUENCE: 14
aacaatgggg ttttacaggt aacctacaaa gca                                 33

<210> SEQ ID NO 15
<211> LENGTH: 35
<212> TYPE: DNA
<213> ORGANISM: Artificial Sequence
<220> FEATURE:
<223> OTHER INFORMATION: Synthetic- TS_SARS2_ORF1b_C6_rev5

<400> SEQUENCE: 15
tcaacaatgg ggttttacag gtaacctaca aagca                               35

<210> SEQ ID NO 16
<211> LENGTH: 31
<212> TYPE: DNA
<213> ORGANISM: Artificial Sequence
<220> FEATURE:
<223> OTHER INFORMATION: Synthetic- TS_SARS2_N_C7_rev1

<400> SEQUENCE: 16
gacaaggaac tgattacaaa cattggccgc a                                   31

<210> SEQ ID NO 17
<211> LENGTH: 33
<212> TYPE: DNA
<213> ORGANISM: Artificial Sequence
<220> FEATURE:
<223> OTHER INFORMATION: Synthetic- TS_SARS2_N_C7_rev2

<400> SEQUENCE: 17
cagacaagga actgattaca aacattggcc gca                                 33

<210> SEQ ID NO 18
<211> LENGTH: 30
<212> TYPE: DNA
<213> ORGANISM: Artificial Sequence
<220> FEATURE:
<223> OTHER INFORMATION: Synthetic- TS_SARS2_N_C7_rev3

<400> SEQUENCE: 18
caaggaactg attacaaaca ttggccgcaa                                     30

<210> SEQ ID NO 19
<211> LENGTH: 30
<212> TYPE: DNA
<213> ORGANISM: Artificial Sequence
<220> FEATURE:
<223> OTHER INFORMATION: Synthetic- TS_SARS2_N_C9_rev1
```

<400> SEQUENCE: 19
gattacaaac attggccgca aattgcacaa                              30

<210> SEQ ID NO 20
<211> LENGTH: 35
<212> TYPE: DNA
<213> ORGANISM: Artificial Sequence
<220> FEATURE:
<223> OTHER INFORMATION: Synthetic- TS_SARS2_N_C9_rev2

<400> SEQUENCE: 20
ggaactgatt acaaacattg gccgcaaatt gcaca                        35

<210> SEQ ID NO 21
<211> LENGTH: 36
<212> TYPE: DNA
<213> ORGANISM: Artificial Sequence
<220> FEATURE:
<223> OTHER INFORMATION: Synthetic- TS_SARS2_N_C9_rev4

<400> SEQUENCE: 21
aggaactgat tacaaacatt ggccgcaaat tgcaca                       36

<210> SEQ ID NO 22
<211> LENGTH: 55
<212> TYPE: DNA
<213> ORGANISM: Artificial Sequence
<220> FEATURE:
<223> OTHER INFORMATION: Synthetic- TS2_SARS2_E_F7_fwd1

<400> SEQUENCE: 22
gcgctaatac gactcactat agggcagaag atcaggaact ctagaagaat tcaga   55

<210> SEQ ID NO 23
<211> LENGTH: 54
<212> TYPE: DNA
<213> ORGANISM: Artificial Sequence
<220> FEATURE:
<223> OTHER INFORMATION: Synthetic- TS2_SARS2_E_F7_fwd2

<400> SEQUENCE: 23
gcgctaatac gactcactat agggagaaga tcaggaactc tagaagaatt caga    54

<210> SEQ ID NO 24
<211> LENGTH: 30
<212> TYPE: DNA
<213> ORGANISM: Artificial Sequence
<220> FEATURE:
<223> OTHER INFORMATION: Synthetic- TS2_SARS2_E_F7_rev1

<400> SEQUENCE: 24
gagacaggta cgttaatagt taatagcgta                              30

<210> SEQ ID NO 25
<211> LENGTH: 31
<212> TYPE: DNA
<213> ORGANISM: Artificial Sequence
<220> FEATURE:
<223> OTHER INFORMATION: Synthetic- TS2_SARS2_E_F7_rev2

<400> SEQUENCE: 25
agagacaggt acgttaatag ttaatagcgt a                            31

<210> SEQ ID NO 26
<211> LENGTH: 110

```
<212> TYPE: RNA
<213> ORGANISM: Artificial Sequence
<220> FEATURE:
<223> OTHER INFORMATION: Synthetic- TS_SARS2_ORF1b_C1

<400> SEQUENCE: 26
ggguugucaa guccauggua augcacaugu agcuaguugg uuauaguuau gaacagagga      60
gacauaacau gaaccaacua aacuugguua accuggcggc agcgcaaaag              110

<210> SEQ ID NO 27
<211> LENGTH: 110
<212> TYPE: RNA
<213> ORGANISM: Artificial Sequence
<220> FEATURE:
<223> OTHER INFORMATION: Synthetic- TS_SARS2_ORF1b_C2

<400> SEQUENCE: 27
gggagcaacc augaucugua uugucaaguc caugguaaug uuauaguuau gaacagagga      60
gacauaacau gaacauuacc aacaauguua accuggcggc agcgcaaaag              110

<210> SEQ ID NO 28
<211> LENGTH: 110
<212> TYPE: RNA
<213> ORGANISM: Artificial Sequence
<220> FEATURE:
<223> OTHER INFORMATION: Synthetic- TS_SARS2_ORF1b_C3

<400> SEQUENCE: 28
gggccaugau cuguauuguc aaguccaugg uaaugcacag uuauaguuau gaacagagga      60
gacauaacau gaacugugca aacacaguua accuggcggc agcgcaaaag              110

<210> SEQ ID NO 29
<211> LENGTH: 109
<212> TYPE: RNA
<213> ORGANISM: Artificial Sequence
<220> FEATURE:
<223> OTHER INFORMATION: Synthetic- TS_SARS2_ORF1b_C4

<400> SEQUENCE: 29
gggucaaguc caugguaaug cacauguagc uaguuggu uauaguuaug aacagaggag      60
acauaacaug aaccacaaca acgugguuaa ccuggcggca gcgcaaaag              109

<210> SEQ ID NO 30
<211> LENGTH: 110
<212> TYPE: RNA
<213> ORGANISM: Artificial Sequence
<220> FEATURE:
<223> OTHER INFORMATION: Synthetic- TS_SARS2_ORF1b_C5

<400> SEQUENCE: 30
gggcaagucc augguaaugc acauguagcu aguugaaug uuauaguuau gaacagagga      60
gacauaacau gaacaucaca aacgauguua accuggcggc agcgcaaaag              110

<210> SEQ ID NO 31
<211> LENGTH: 110
<212> TYPE: RNA
<213> ORGANISM: Artificial Sequence
<220> FEATURE:
<223> OTHER INFORMATION: Synthetic- TS_SARS2_ORF1b_C6

<400> SEQUENCE: 31
ggguccaugg uaaugcacau guagcuaguu gugaugcaag uuauaguuau gaacagagga      60
```
gacauaacau gaacuugcau aaccaaguua accuggcggc agcgcaaaag    110

<210> SEQ ID NO 32
<211> LENGTH: 110
<212> TYPE: RNA
<213> ORGANISM: Artificial Sequence
<220> FEATURE:
<223> OTHER INFORMATION: Synthetic- TS_SARS2_N_C7

<400> SEQUENCE: 32
gggaauuugc ccccagcgcu ucagcguucu ucggaaugug uuauaguuau gaacagagga    60
gacauaacau gaacacauuc aacuguguua accuggcggc agcgcaaaag    110

<210> SEQ ID NO 33
<211> LENGTH: 110
<212> TYPE: RNA
<213> ORGANISM: Artificial Sequence
<220> FEATURE:
<223> OTHER INFORMATION: Synthetic- TS_SARS2_N_C8

<400> SEQUENCE: 33
gggcaauuug cccccagcgc uucagcguuc uucggaaugg uuauaguuau gaacagagga 60
gacauaacau gaaccauucc aacaugguua accuggcggc agcgcaaaag 110

<210> SEQ ID NO 34
<211> LENGTH: 110
<212> TYPE: RNA
<213> ORGANISM: Artificial Sequence
<220> FEATURE:
<223> OTHER INFORMATION: Synthetic- TS_SARS2_N_C9

<400> SEQUENCE: 34
gggccccagc gcuucagcgu ucuucggaau gucgcgcaug uuauaguuau gaacagagga 60
gacauaacau gaacaugcgc aaccauguua accuggcggc agcgcaaaag 110

<210> SEQ ID NO 35
<211> LENGTH: 109
<212> TYPE: RNA
<213> ORGANISM: Artificial Sequence
<220> FEATURE:
<223> OTHER INFORMATION: Synthetic- TS_SARS2_N_C10

<400> SEQUENCE: 35
gggcccccag cgcuucagcg uucuucggaa ugucgcgcgu uauaguuaug aacagaggag 60
acauaacaug aacgcgcgaa accgcguuaa ccuggcggca gcgcaaaag 109

<210> SEQ ID NO 36
<211> LENGTH: 110
<212> TYPE: RNA
<213> ORGANISM: Artificial Sequence
<220> FEATURE:
<223> OTHER INFORMATION: Synthetic- TS_SARS2_N_C11

<400> SEQUENCE: 36
gggcccagcg cuucagcguu cuucggaaug ucgcgcauug uuauaguuau gaacagagga 60
gacauaacau gaacaaugcg aacauuguua accuggcggc agcgcaaaag 110

<210> SEQ ID NO 37
<211> LENGTH: 110
<212> TYPE: RNA
<213> ORGANISM: Artificial Sequence
<220> FEATURE:
<223> OTHER INFORMATION: Synthetic- TS_SARS2_N_C12

<400> SEQUENCE: 37
gggcacaauu ugcccccagc gcuucagcgu ucuucggaag uuauaguuau gaacagagga    60
gacauaacau gaacuuccga aacgaaguua accuggcggc agcgcaaaag             110

<210> SEQ ID NO 38
<211> LENGTH: 110
<212> TYPE: RNA
<213> ORGANISM: Artificial Sequence
<220> FEATURE:
<223> OTHER INFORMATION: Synthetic- TS_SARS2_RdRP_D1

<400> SEQUENCE: 38
ggguauaugu uaaaccaggu ggaaccucau caggagaugg uuauaguuau gaacagagga    60
gacauaacau gaaccaucuc aacaugguua accuggcggc agcgcaaaag             110

<210> SEQ ID NO 39
<211> LENGTH: 110
<212> TYPE: RNA
<213> ORGANISM: Artificial Sequence
<220> FEATURE:
<223> OTHER INFORMATION: Synthetic- TS_SARS2_RdRP_D2

<400> SEQUENCE: 39
gggcuauaug uuaaaccagg uggaaccuca ucaggagaug uuauaguuau gaacagagga    60
gacauaacau gaacaucucc aacgauguua accuggcggc agcgcaaaag             110

<210> SEQ ID NO 40
<211> LENGTH: 110
<212> TYPE: RNA
<213> ORGANISM: Artificial Sequence
<220> FEATURE:
<223> OTHER INFORMATION: Synthetic- TS_SARS2_RdRP_D3

<400> SEQUENCE: 40
gggacuauau guuaaaccag guggaaccuc aucaggagag uuauaguuau gaacagagga    60
gacauaacau gaacucuccu aacagaguua accuggcggc agcgcaaaag             110

<210> SEQ ID NO 41
<211> LENGTH: 110
<212> TYPE: RNA
<213> ORGANISM: Artificial Sequence
<220> FEATURE:
<223> OTHER INFORMATION: Synthetic- TS_SARS2_RdRP_D4

<400> SEQUENCE: 41
ggguauguua aaccaggugg aaccucauca ggagaugccg uuauaguuau gaacagagga    60
gacauaacau gaacggcauc aacgccguua accuggcggc agcgcaaaag             110

<210> SEQ ID NO 42
<211> LENGTH: 110
<212> TYPE: RNA
<213> ORGANISM: Artificial Sequence
<220> FEATURE:
<223> OTHER INFORMATION: Synthetic- TS_SARS2_RdRP_D5

<400> SEQUENCE: 42
ggguucacua uauguuaaac caggugggaac cucaucaggg uuauaguuau gaacagagga    60
gacauaacau gaacccugau aacaggguua accuggcggc agcgcaaaag             110

<210> SEQ ID NO 43

```
<211> LENGTH: 110
<212> TYPE: RNA
<213> ORGANISM: Artificial Sequence
<220> FEATURE:
<223> OTHER INFORMATION: Synthetic- TS_SARS2_RdRP_D6

<400> SEQUENCE: 43
gggauauguu aaaccaggug gaaccucauc aggagaugcg uuauaguuau gaacagagga      60
gacauaacau gaacgcaucu aacugcguua accuggcggc agcgcaaaag               110

<210> SEQ ID NO 44
<211> LENGTH: 110
<212> TYPE: RNA
<213> ORGANISM: Artificial Sequence
<220> FEATURE:
<223> OTHER INFORMATION: Synthetic- TS_SARS2_E_D7

<400> SEQUENCE: 44
gggucuuuuu cuugcuuucg ugguauucuu gcuaguuacg uuauaguuau gaacagagga      60
gacauaacau gaacguaacu aacuacguua accuggcggc agcgcaaaag               110

<210> SEQ ID NO 45
<211> LENGTH: 110
<212> TYPE: RNA
<213> ORGANISM: Artificial Sequence
<220> FEATURE:
<223> OTHER INFORMATION: Synthetic- TS_SARS2_E_D8

<400> SEQUENCE: 45
gggcuuucgu gguauucuug cuaguuacac uagccauccg uuauaguuau gaacagagga      60
gacauaacau gaacggaugg aacuccguua accuggcggc agcgcaaaag               110

<210> SEQ ID NO 46
<211> LENGTH: 110
<212> TYPE: RNA
<213> ORGANISM: Artificial Sequence
<220> FEATURE:
<223> OTHER INFORMATION: Synthetic- TS_SARS2_E_D9

<400> SEQUENCE: 46
ggguuuucuu gcuuucgugg uauucuugcu aguuacacug uuauaguuau gaacagagga      60
gacauaacau gaacagugua aacacuguua accuggcggc agcgcaaaag               110

<210> SEQ ID NO 47
<211> LENGTH: 110
<212> TYPE: RNA
<213> ORGANISM: Artificial Sequence
<220> FEATURE:
<223> OTHER INFORMATION: Synthetic- TS_SARS2_E_D10

<400> SEQUENCE: 47
ggguuucgug guauucuugc uaguuacacu agccauccug uuauaguuau gaacagagga      60
gacauaacau gaacaggaug aacccuguua accuggcggc agcgcaaaag               110

<210> SEQ ID NO 48
<211> LENGTH: 110
<212> TYPE: RNA
<213> ORGANISM: Artificial Sequence
<220> FEATURE:
<223> OTHER INFORMATION: Synthetic- TS_SARS2_E_D11

<400> SEQUENCE: 48
gggcuuuuuc uugcuuucgu gguauucuug cuaguuacag uuauaguuau gaacagagga      60
```

```
gacauaacau gaacuguaac aacacaguua accuggcggc agcgcaaaag            110
```

<210> SEQ ID NO 49
<211> LENGTH: 110
<212> TYPE: RNA
<213> ORGANISM: Artificial Sequence
<220> FEATURE:
<223> OTHER INFORMATION: Synthetic- TS_SARS2_E_D12

<400> SEQUENCE: 49

```
ggguugcuuu

-continued

```
<212> TYPE: RNA
<213> ORGANISM: Artificial Sequence
<220> FEATURE:
<223> OTHER INFORMATION: Synthetic- Orf1b TH =
TSgen2_2019_nCoV_ORF1b_sensA
<400> SEQUENCE: 54
gggcaucaca acuagcuaca ugugcauuac cauggacugu uauaguuaug aacagaggag 60
acauaacaug aacaguccaa acacuguuaa ccuggcggca gcgcaaaag 109

<210> SEQ ID NO 55
<211> LENGTH: 153
<212> TYPE: RNA
<213> ORGANISM: Artificial Sequence
<220> FEATURE:
<223> OTHER INFORMATION: Synthetic- N SNIPR1 = SNIPR_2019_nCoV_N_N2

<400> SEQUENCE: 55
gggugugacu uccaugccaa ugcgcgacau uugcgaaaga gcugaagcgc ugggggcaaa 60
uuugcauaaa gaggagauua gaaaugugca aauuugcccc cagcgcuucg cauaacucau 120
aucgguccau gaccaugauu acggauucac ugg 153

<210> SEQ ID NO 56
<211> LENGTH: 153
<212> TYPE: RNA
<213> ORGANISM: Artificial Sequence
<220> FEATURE:
<223> OTHER INFORMATION: Synthetic- N SNIPR 2 = SNIPR_2019_nCoV_N_N6

<400> SEQUENCE: 56
gggugugacu uccaugccaa ugcgcgacau ucugauggga gcugaagcgc ugggggcaaa 60
uuugcauaca gaggagauca cagaugugca aauuugcccc cagcgcucaa ucuggcaugu 120
gucauggcau gaccaugauu acggauucac ugg 153

<210> SEQ ID NO 57
<211> LENGTH: 100
<212> TYPE: RNA
<213> ORGANISM: Artificial Sequence
<220> FEATURE:
<223> OTHER INFORMATION: Synthetic-
TSgen2_Ref5A_nucleocapsid_targ_Bloop_antisense_lacZ_T37_top_3

<400> SEQUENCE: 57
ggguuccaau uaacaccaau agcaguccag uuauaguuau gaacagagga gacauaacau 60
gaacuggacu aacccaguua accuggcggc agcgcaaaag 100

<210> SEQ ID NO 58
<211> LENGTH: 106
<212> TYPE: RNA
<213> ORGANISM: Artificial Sequence
<220> FEATURE:
<223> OTHER INFORMATION: Synthetic- 2B_N_B_32nt_2

<400> SEQUENCE: 58
ggguccucau cacguagucg caacaguuca agaaaguuau aguuaugaac agaggagaca 60
uaacaugaac uuucuuaaca aaguuaaccu ggcggcagcg caaaag 106

<210> SEQ ID NO 59
<211> LENGTH: 95
<212> TYPE: RNA
<213> ORGANISM: Artificial Sequence
<220> FEATURE:

```
<223> OTHER INFORMATION: Synthetic-
      EAR_22_Ref16A_ctl_18S_rRNA_targ_Bloop_antisense_lacZ_T37_4

<400> SEQUENCE: 59
gggagaggug aaauucuugg accggcgcaa gacgggacuu uagaacagag gagauaaaga    60
ugcgucuugc gccaaaccug gcggcagcgc aaaag                               95

<210> SEQ ID NO 60
<211> LENGTH: 100
<212> TYPE: RNA
<213> ORGANISM: Artificial Sequence
<220> FEATURE:
<223> OTHER INFORMATION: Synthetic-
      TSgen2_Ref16A_ctl_18S_rRNA_targ_Floop_sense_lacZ_T37_top_3

<400> SEQUENCE: 60
ggguccuauu ccauuauucc uagcugcggg uuauaguuau gaacagagga gacauaacau    60
gaacccgcag aaccggguua accuggcggc agcgcaaaag                         100

<210> SEQ ID NO 61
<211> LENGTH: 106
<212> TYPE: RNA
<213> ORGANISM: Artificial Sequence
<220> FEATURE:
<223> OTHER INFORMATION: Synthetic- 2C_Spike_B_32_4 (Fig. 19B; 21B)

<400> SEQUENCE: 61
gggauaaccc uguccuacca uuuaaugaug guguuguuau aguuaugaac agaggagaca    60
uaacaugaac aacaccaacg uuguuaaccu ggcggcagcg caaaag                  106

<210> SEQ ID NO 62
<211> LENGTH: 106
<212> TYPE: RNA
<213> ORGANISM: Artificial Sequence
<220> FEATURE:
<223> OTHER INFORMATION: Synthetic- 2C_spike_F_32_3 (Fig. 19A; 21A)

<400> SEQUENCE: 62
gggagguaag aacaaguccu gaguugaaug uaaaaguuau aguuaugaac agaggagaca    60
uaacaugaac uuuuacaaca aaguuaaccu ggcggcagcg caaaag                  106

<210> SEQ ID NO 63
<211> LENGTH: 95
<212> TYPE: RNA
<213> ORGANISM: Artificial Sequence
<220> FEATURE:
<223> OTHER INFORMATION: Synthetic-
      EAR_22_Ref16A_ctl_18S_rRNA_targ_Bloop_antisense_lacZ_T37_2 (Fig.
      19C; 21C)

<400> SEQUENCE: 63
gggaggugaa auucuuggac cggcgcaaga cggaggacuu uagaacagag gagauaaaga    60
uguccgucuu gcggaaccug gcggcagcgc aaaag                               95

<210> SEQ ID NO 64
<211> LENGTH: 99
<212> TYPE: RNA
<213> ORGANISM: Artificial Sequence
<220> FEATURE:
<223> OTHER INFORMATION: Synthetic-
      TSgen2_Ref17A_ctl_ACTB_mRNA_targ_Floop_sense_lacZ_T37_top_2 (Fig.
      19D)

<400> SEQUENCE: 64
```

```
gggauuuucu ccaugucguc ccaguugggu uauaguuaug aacagaggag acauaacaug    60
aacccaacua acuggguuaa ccuggcggca gcgcaaaag                           99
```

<210> SEQ ID NO 65
<211> LENGTH: 18
<212> TYPE: DNA
<213> ORGANISM: Artificial Sequence
<220> FEATURE:
<223> OTHER INFORMATION: Synthetic- Ref2C_spike_F3

<400> SEQUENCE: 65

```
tctttcacac gtggtgtt                                                  18
```

<210> SEQ ID NO 66
<211> LENGTH: 19
<212> TYPE: DNA
<213> ORGANISM: Artificial Sequence
<220> FEATURE:
<223> OTHER INFORMATION: Synthetic- Ref2C_spike_B3

<400> SEQUENCE: 66

```
gtaccaaaaa tccagcctc                                                 19
```

<210> SEQ ID NO 67
<211> LENGTH: 46
<212> TYPE: DNA
<213> ORGANISM: Artificial Sequence
<220> FEATURE:
<223> OTHER INFORMATION: Synthetic- Ref2C_spike_FIP

<400> SEQUENCE: 67

```
catggaacca agtaacattg gaaaacctga caaagttttc agatcc                   46
```

<210> SEQ ID NO 68
<211> LENGTH: 42
<212> TYPE: DNA
<213> ORGANISM: Artificial Sequence
<220> FEATURE:
<223> OTHER INFORMATION: Synthetic- Ref2C_spike_BIP

<400> SEQUENCE: 68

```
ctctgggacc aatggtacta agaggacttc tcagtggaag ca                       42
```

<210> SEQ ID NO 69
<211> LENGTH: 24
<212> TYPE: DNA
<213> ORGANISM: Artificial Sequence
<220> FEATURE:
<223> OTHER INFORMATION: Synthetic- Ref2C_spike_LF

<400> SEQUENCE: 69

```
gaaaggtaag aacaagtcct gagt                                           24
```

<210> SEQ ID NO 70
<211> LENGTH: 25
<212> TYPE: DNA
<213> ORGANISM: Artificial Sequence
<220> FEATURE:
<223> OTHER INFORMATION: Synthetic- Ref2C_spike_LB

<400> SEQUENCE: 70

```
ctgtcctacc atttaatgat ggtgt                                          25
```

<210> SEQ ID NO 71

```
<211> LENGTH: 18
<212> TYPE: DNA
<213> ORGANISM: Artificial Sequence
<220> FEATURE:
<223> OTHER INFORMATION: Synthetic- Ref16A_ctl_18S_rRNA_F3

<400> SEQUENCE: 71
gttcaaagca ggcccgag                                                  18

<210> SEQ ID NO 72
<211> LENGTH: 20
<212> TYPE: DNA
<213> ORGANISM: Artificial Sequence
<220> FEATURE:
<223> OTHER INFORMATION: Synthetic- Ref16A_ctl_18S_rRNA_B3

<400> SEQUENCE: 72
cctccgactt tcgttcttga                                                20

<210> SEQ ID NO 73
<211> LENGTH: 41
<212> TYPE: DNA
<213> ORGANISM: Artificial Sequence
<220> FEATURE:
<223> OTHER INFORMATION: Synthetic- Ref16A_ctl_18S_rRNA_FIP

<400> SEQUENCE: 73
tggcctcagt tccgaaaacc aacctggata ccgcagctag g                        41

<210> SEQ ID NO 74
<211> LENGTH: 39
<212> TYPE: DNA
<213> ORGANISM: Artificial Sequence
<220> FEATURE:
<223> OTHER INFORMATION: Synthetic- Ref16A_ctl_18S_rRNA_BIP

<400> SEQUENCE: 74
ggcattcgta ttgcgccgct ggcaaatgct ttcgctctg                           39

<210> SEQ ID NO 75
<211> LENGTH: 25
<212> TYPE: DNA
<213> ORGANISM: Artificial Sequence
<220> FEATURE:
<223> OTHER INFORMATION: Synthetic- Ref16A_ctl_18S_rRNA_LF

<400> SEQUENCE: 75
agaaccgcgg tcctattcca ttatt                                          25

<210> SEQ ID NO 76
<211> LENGTH: 20
<212> TYPE: DNA
<213> ORGANISM: Artificial Sequence
<220> FEATURE:
<223> OTHER INFORMATION: Synthetic- Ref16A_ctl_18S_rRNA_LB

<400> SEQUENCE: 76
attccttgga ccggcgcaag                                                20

<210> SEQ ID NO 77
<211> LENGTH: 11
<212> TYPE: DNA
<213> ORGANISM: Artificial Sequence
<220> FEATURE:
<223> OTHER INFORMATION: Shine-Dalgarno sequence fragment

<400> SEQUENCE: 77
```

```
aacagaggag a                                                              11

<210> SEQ ID NO 78
<211> LENGTH: 12
<212> TYPE: DNA
<213> ORGANISM: Artificial Sequence
<220> FEATURE:
<223> OTHER INFORMATION: Shine-Dalgarno sequence fragment

<400> SEQUENCE: 78
gaacagagga ga                                                             12
```

RAPID LOW-COST DETECTION OF SARS-COV-2 USING ISOTHERMAL AMPLIFICATION AND SENSING METHODS

CROSS-REFERENCE TO RELATED APPLICATIONS

This application is a national stage filing under 35 U.S.C. § 371 of International Application No. PCT/US2021/037092, filed Jun. 11, 2021, which claims the benefit of U.S. Provisional Application No. 63/038,609 filed on Jun. 12, 2020, the entire contents of which are incorporated herein by reference in their entireties.

STATEMENT REGARDING FEDERALLY FUNDED RESEARCH OR DEVELOPMENT

This invention was made with government support under R21 AI136571 and GM126892 awarded by the National Institutes of Health. The government has certain rights in the invention.

SEQUENCE LISTING

A Sequence Listing accompanies this application and is submitted as an ASCII text file of the sequence listing named "112624_01252_ST25.txt" which is 20 KB in size and was created on Jul. 26, 2021. The sequence listing is electronically submitted via EFS-Web with the application and is incorporated herein by reference in its entirety.

FIELD

The present technology relates to methods for detection of infectious agents such as SARS-CoV-2, the causative agent of COVID-19.

BACKGROUND

The COVID-19 pandemic demands the development of easy-to-use, rapid, and low-cost diagnostic technologies that can be easily deployed to diagnose infected individuals for disease treatment, containment, and contact tracing. PCR-based assays in widespread use are highly sensitive and specific; however, they require a substantial investment in equipment and trained personnel for running the tests. These infrastructure requirements substantially increase both the cost and time required to return assay results. Accordingly, there remains a need in the art for rapid, inexpensive, and highly sensitive diagnostic tests for the genetic signature of the SARS-CoV-2 coronavirus, the causative agent of COVID-19, that require neither sophisticated laboratory equipment nor biosafety level 3 containment.

BRIEF SUMMARY

This disclosure is related to methods and compositions for the rapid, highly sensitive detection of the causative agents of COVID-19. As described herein, the methods and compositions are useful for early detection of SARS-CoV-2 and, consequently, improved health outcomes.

BRIEF DESCRIPTION OF THE DRAWINGS

FIG. 2A-F shows toehold switches with lacZ output in cell-free reactions targeting sense orientation targets in SARS-CoV-2.

FIG. 3A-D shows discrimination performance of toehold switches and highly sequence-specific SNIPR sensors in the presence of target RNAs from SARS-CoV-2 and SARS-CoV.

FIG. 4A-F shows output from toehold switches with lacZ-alpha peptide output in cell-free reactions targeting the anti-sense orientation of targets in SARS-CoV-2.

FIG. 5A-F shows output from toehold switches with full-length lacZ output in cell-free reactions targeting the anti-sense orientation of targets in SARS-CoV-2.

FIG. 6A-D shows output from toehold switches for the anti-sense orientation of the N gene. (A,B) Sensor N-C7 with lacZ-alpha (A) and lacZ (B) output proteins. (C,D) Sensor N-C9 with lacZ-alpha (C) and lacZ (D) output proteins.

FIG. 7A-B displays photographs of cell-free reactions with toehold switches at room temperature after 2 hours (left image, A) and 2.5 hours (right image, B). Sensors Orf1b-C2, E-F8, and N-C9 are shown and display clear color differences depending on if a SARS-CoV-2 trigger is present in the reaction.

FIG. 8A-B shows fluorescence response of toehold switches with lacZ outputs using the fluorogenic substrate FDG. (A) Plate reader measurements of toehold switches for antisense targets in the Orf1b, N, and E genes. (B) Photograph of the paper-based cell-free reactions with FDG showing the visible change in assay appearance following detection (+).

FIG. 10A-B shows detection down to 0.5 aM (15 copies per reaction) of SARS-CoV-2 genomic RNA using toehold switch N-C9 for the antisense of gene N using RT-RPA primer pair 1 (left graph) and primer pair 2 (right graph). See FIGS. 12 and 13 for Primer Pair identification.

FIG. 11A-D shows detection results for NASBA reactions coupled with SNIPRs detecting the sense orientations of SARS-CoV-2 genes N and Orf1b. These assays can detect down to 10 RNA copies with responses from the paper-based reactions down to 50 minutes.

FIG. 12 presents Table 1, exemplary primer sequences SEQ ID NOs: 1-25 used for isothermal amplification of SARS-CoV-2 RNA gene regions.

FIG. 13 presents Table 2, primer pairs used for isothermal amplification of SARS-CoV-2 RNA gene regions.

FIG. 14 presents Table 3, exemplary sensor sequences of the riboregulators of the present technology. In general, the sensor sequence represents the regulatory/sensing components of the riboregulator (and the GGG leader sequence for transcription) through to the base before the start of the of the reporter gene sequence. For the SNIPR sequences, the sequence given also includes the first 29 nucleotides of the reporter protein at the 3' end of the sequence. For sensors with names beginning with "TS_", "TSgen2": The complementary region to the target is 36 nt and generally runs from base 4 to 39 (36 nt total), the loop region is the 11-nt AACAGAGGAGA (SEQ ID NO: 77) sequence (Shine Dalgarno sequence in bold), the start codon follows the AGGAGA after a 6-nt gap. The conserved linker sequence comprise the last 21 nt of the sequence given. In some cases, the complementary region will be shifted to the 5' end. This occurs when the complementary region begins with a G and can thus overlap with the GGG leader required for T7 RNAP transcription. For sensors with names beginning with "TS2_", "EAR_H22": The complementary region to the target is 36 nt and generally runs from base 4 to 39 (36 nt total), the loop region is the 12-nt GAACAGAGGAGA (SEQ ID NO: 78) sequence (Shine Dalgarno sequence in bold), the start codon follows the AGGAGA after a 5-nt gap. The conserved linker sequence consists of the last 21 nt of the sequence given. In some cases, the complementary region will be shifted to the 5' end. This occurs when the complementary region begins with a G and can thus overlap with the GGG leader required for T7 RNAP transcription. By way of example, two of the riboregulators provided in FIG. 14 are shown below, with some of the functional regions in bold, or italics.

TS_SARS2_E_D12

(SEQ ID NO: 49)
GGGUUGCUUUCGUGGUAUUCUUGCUAGUUACACUAGCCAGUUAUAGU

UAUGAACAGAGGAGACAUAACAUGAACUGGCUAAACCCAGUUAACCGG

GCGGCAGCGCAAAAG

TS2_SARS2_E_F7

(SEQ ID NO: 50)
GGGCGUGGUAUUCUUGCUAGUUACACUAGCCAUCCUUACGGACUUUA

GAACAGAGGAGAUAAAGAUGGUAAGGAUGGCAAACCUGGCGGCAGCGC

AAAAG

Figure 15:
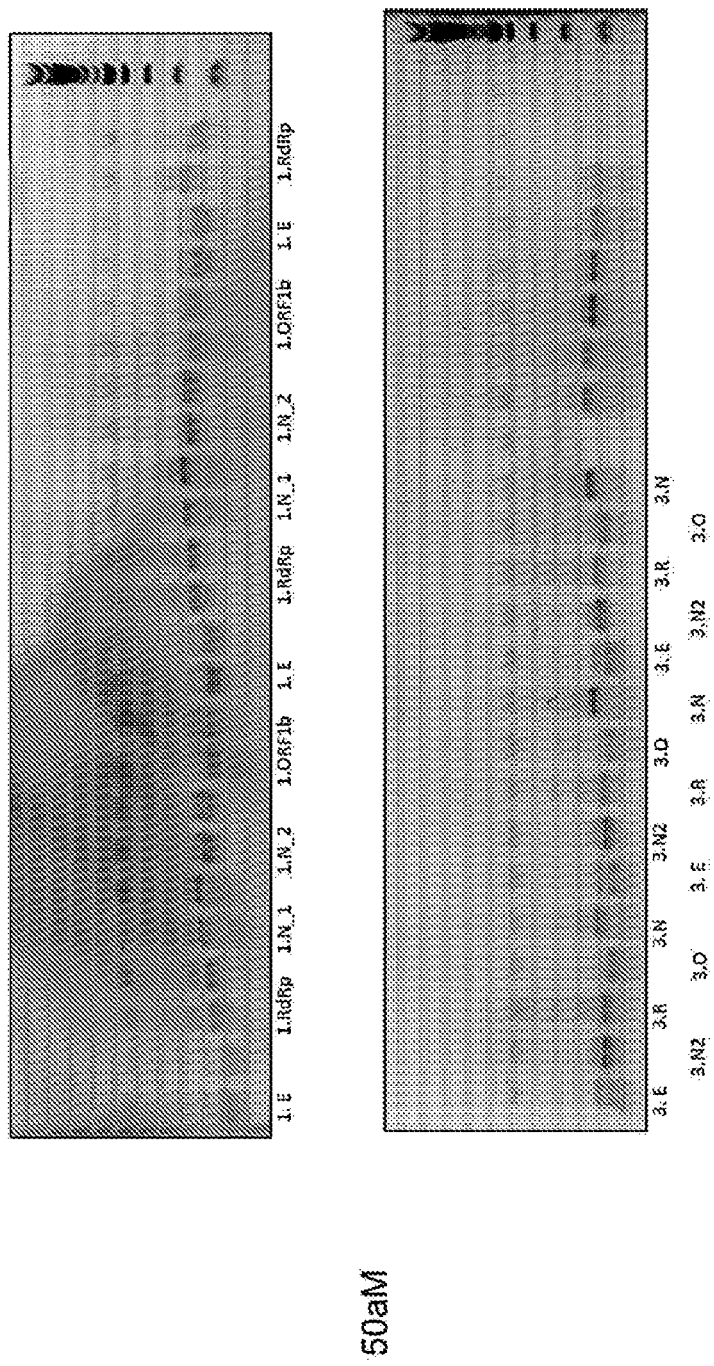

FIG. 15 presents RT-RPA DNA imaging results showing amplification efficiency.

Figure 16:
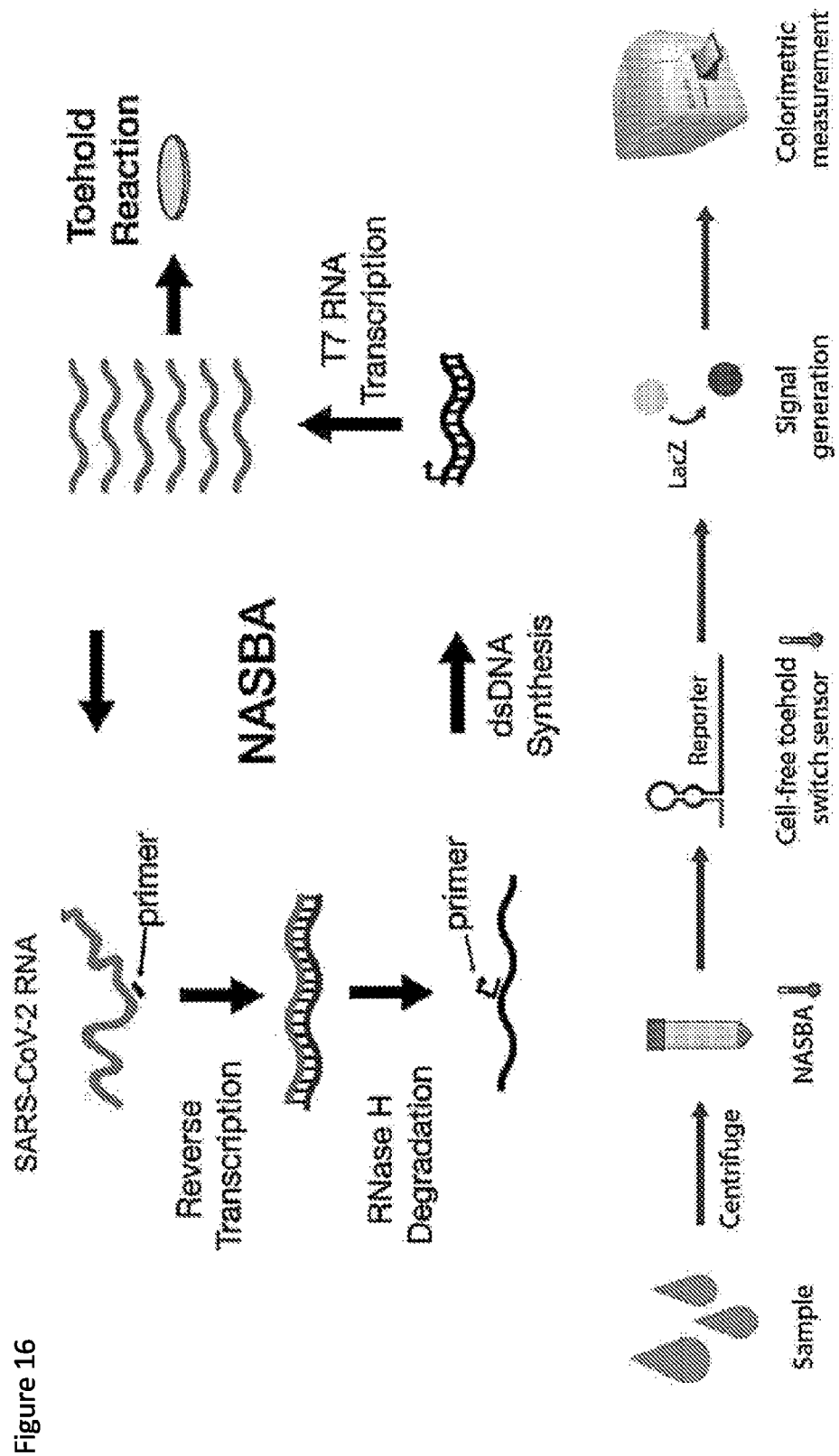

FIG. 16 illustrates an exemplary work flow for detecting SARS-CoV-2.

Figure 17:
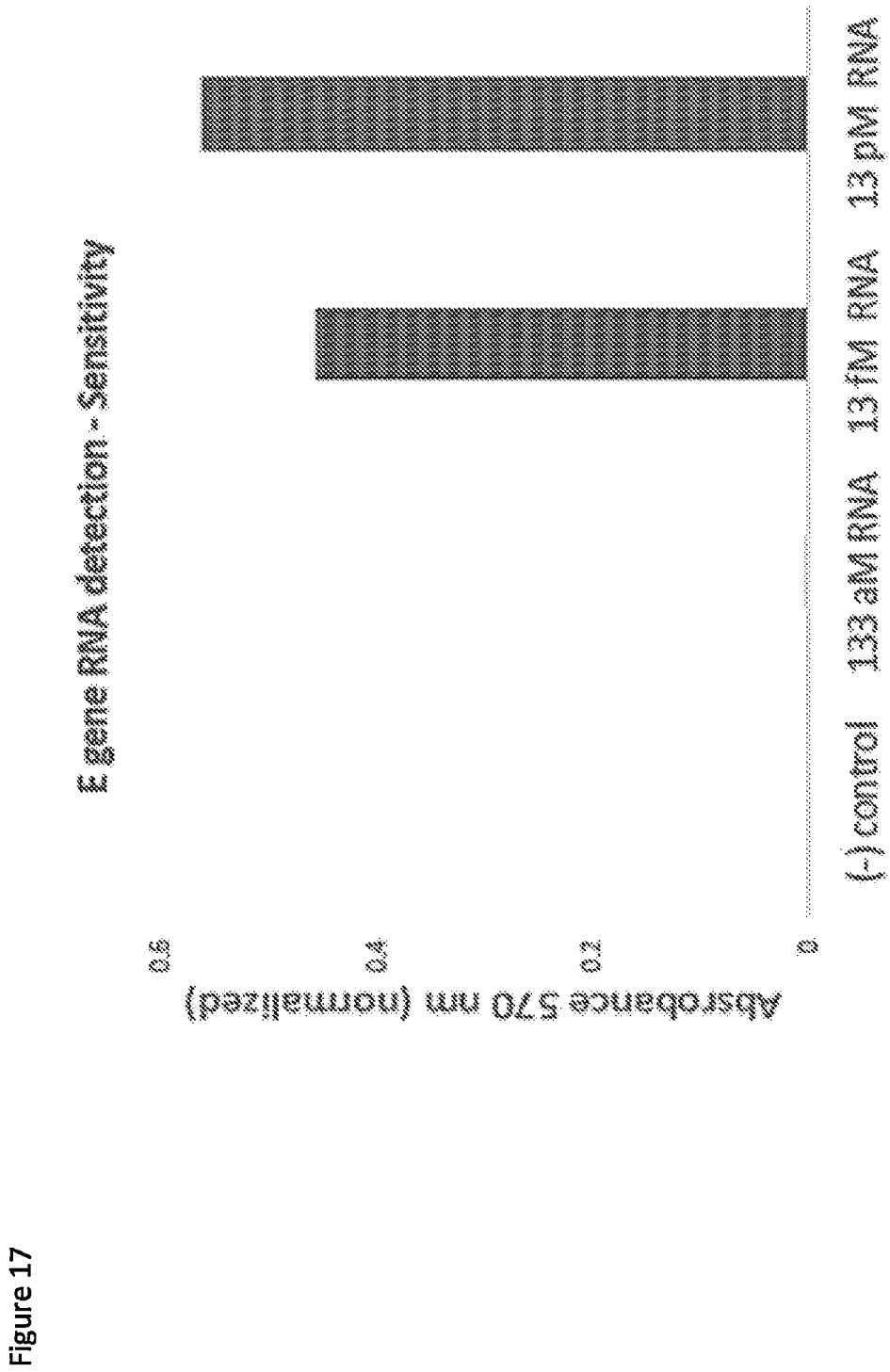
Figure 17:
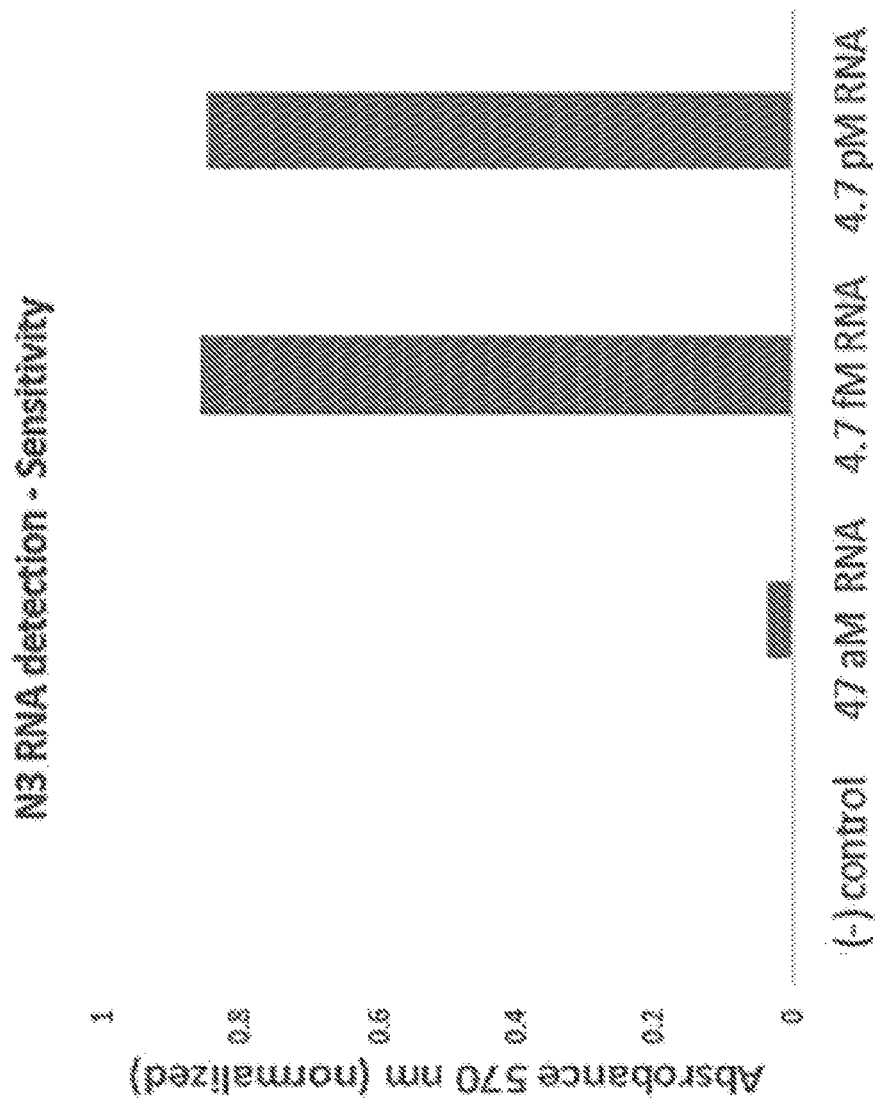

FIG. 17 demonstrates sensitivity of SARS-CoV-2-specific toehold sequences using the workflow as illustrated in FIG. 16.

Figure 18A:
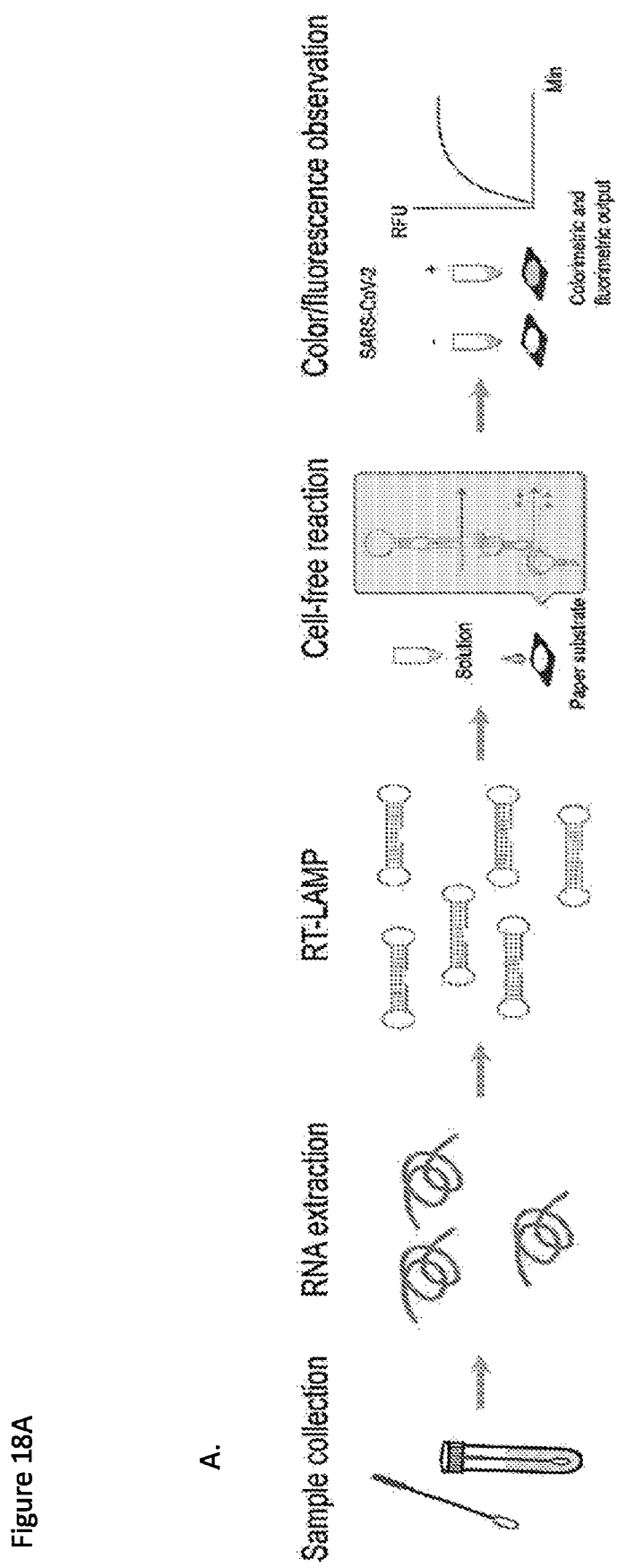

FIG. 18A-B. 18A presents the process used for detecting SARS-CoV-2 using RT-LAMP amplification and toehold switches for sequence verification. 18B presents a schematic of the LacZ tetramer and the screening protocol for LAMP toehold switches.

FIGS. 19A-D present time-course measurements of toehold switches using the lacZ-alpha subunit reporter activating in response to stem-loop DNA targets matching the sequence of RT-LAMP DNA amplicons. Toehold switches activate in response to DNA from the spike gene of SARS-CoV-2 as well as control targets from 18S rRNA and the ACTB mRNA.

FIG. 20 provides experimental information for a RT-LAMP reaction protocol.

FIGS. 21A-C present limit of detection measurements for the RT-LAMP/toehold switch assays targeting the SARS-CoV-2 spike gene (20A and 20B) and 16S rRNA (20C). Data are shown after 2 hour cell-free reactions. Results from two-tailed student's t-test are indicated with *p<0.05, p<0.01, *p<0.001 in figure.

DETAILED DESCRIPTION

All publications, including but not limited to patents and patent applications, cited in this specification are herein incorporated by reference as though set forth in their entirety in the present application.

Definitions

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The terms "nucleic acid" and "oligonucleotide," as used herein, refer to polydeoxyribonucleotides (containing 2-deoxy-DRibose), polyribonucleotides (containing DRibose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present disclosure, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)n sequence, where n is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

Amplification reaction as used herein also encompasses isothermal amplification reactions. By way of example, but not by way of limitation, isothermal amplification reactions include nucleic acid sequence-based amplification (NASBA) and reverse transcription polymerase amplification reaction (RT-RPA), loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RP A), and polymerase spiral reaction (PSR), which is described at nature.com/articles/srep12723 on the World Wide Web. In some cases, recombinase polymerase amplification (RPA) is used with the "one-pot" amplification and detection methods provided herein. In such cases, the methods comprise performing reverse transcription (RT), RPA, and transcription (TX) and/or translation (TL) methods in a single test tube. In the context of an amplification reaction, isothermal refers to an amplification reaction that does not require melting of double-stranded nucleic acids prior to a polymerase step.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases (e.g., Moloney Murine Leukemia Virus (M-MLV) reverse transcriptase) encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "detect" or "detection" as used herein indicates the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: fluorescence, spectra, or images from a target of interest or a probe attached to the target.

Nucleic acids and/or other moieties of the invention may be isolated. As used herein, "isolated" means to separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like. In some embodiments, a "subject" may include fish, birds, or reptiles.

As used herein a "subject sample" or a "biological sample" from the subject refers to a sample taken from the subject, such as, but not limited to a tissue sample (e.g, fat, muscle, skin, neurological, tumor, etc.) or fluid sample (e.g., saliva, blood, serum, plasma, urine, stool, cerebrospinal fluid, nasal swab, sputum, etc.), and or cells or sub-cellular structures such as vesicles and exosomes.

Riboregulators

As used herein the term "riboregulator" refers to a nucleic acid structure that responds to a signal or trigger nucleic acid molecule by Watson-Crick base pairing. Because riboregulator response is based on base-pairing, a riboregulator can be tailored to differentiate and respond to individual genetic sequences. In some embodiments, a riboregulator comprises a toehold switch. In some embodiments, a riboregulator comprises a single-nucleotide-specific programmable Riboregulator (SNIPR).

Riboregulators of the present technology typically form a secondary structure, such as a hairpin loop, that undergoes a conformational change in the presence of a trigger nucleic acid. The riboregulators disclosed herein comprise at least a first region and a second region. The first region comprises a nucleic acid sequence that is complementary to the signal or trigger molecule. The complementary region, also referred to herein as the "sensor sequence" hybridizes to the trigger, causing a conformational change in the riboregulator (e.g., unfolding of the hairpin). The second region of the riboregulators encodes a reporter protein and the regulatory sequences necessary for translation of the reporter.

When the trigger nucleic acid sequence is present, the complementary region hybridizes to the trigger, inducing a conformational change in the riboregulator. This conformational change exposes a translation regulatory sequence (such as a ribosome binding site or other translational initiation sequence such as a start codon), allowing the translational machinery to bind to the regulatory sequences and initiate translation of the reporter protein.

As used herein, the term "toehold switch" generally refers to a class of RNAs with a hairpin loop that can be unfolded upon binding a trigger RNA, thereby exposing a ribosome binding site (RBS) or other translational regulatory sequences (e.g., a start codon), and permitting translation of a reporter protein.

As used herein the term single-nucleotide specific programmable riboregulator (SNIPR) refers to a toehold switch with single-nucleotide-specific RNA detection capabilities. As a toehold switch, SNIPRs contain (1) a core hairpin secondary structure, (2) a complementary region, (3) encode a reporter protein, and (4) include the translational initiation signals (e.g., RBS) to allow for translation of the reporter. In addition, to achieve ultra-specific recognition capabilities, SNIPRs also include an energy-balancing region. See, e.g., Hong et al., Cell 180(5):1018-1032 (2020), incorporated herein by reference in its entirety.

The energy-balancing region within the hairpin is the most critical component for establishing ultra-specific recognition capabilities. It contains a pair of short forward and reverse toehold domains (generally 3 to 6 nt long) separated by a double-stranded branch migration region. In the OFF state, the RBS and start codon are sequestered within a 17-nt hairpin loop and base paired with the reverse toehold, respectively, preventing recognition by the ribosome. Upon activation of the SNIPR, the single-stranded forward toehold domain binds to the target RNA and promotes a branch migration reaction to unwind most of the hairpin structure. The reverse toehold domain is not complementary to the target and is left undisturbed following the branch migration. However, it is sufficiently short to open spontaneously and expose both the RBS and start codon to activate translation of the downstream output gene. The net effect of the activation process is to form new base pairs with the forward toehold domain while disrupting the base pairs in the reverse toehold domain. Consequently, the overall free energy driving the transition between OFF and ON states can be programmed through the length and sequences of the forward and reverse toeholds, enabling the system to operate near chemical equilibrium. Furthermore, in the event of false activation with a mutated target RNA, a competitive reverse branch migration process can take place via the reverse toehold to re-establish the repressing hairpin structure. Because the short toehold domains of the SNIPR energy-balancing region do not provide sufficient binding energy to reliably initiate hybridization with the target RNA, a complementary region is included. The complementary region hybridizes to the trigger (target), and drives the conformational change necessary to expose the translation regulatory sequences.

Toehold switches form a hairpin structure comprising a stem domain and a loop domain through complementary base pairing. The hairpin structure blocks access to the mRNA transcript by the ribosome, thereby preventing translation. In some embodiments, the stem domain of the hairpin structure sequesters the ribosome binding site (RBS). In some embodiments, including, for example, embodiments involving eukaryotic cells, the stem domain of the hairpin structure is positioned upstream of the start (or initiation) codon. As described herein, in some embodiments the toehold switches are configured for lower leakage relative to previously described riboregulators. In some embodiments, binding of a cognate target RNA to the updated toehold switch unwinds the lower half of the switch RNA hairpin and leaves the conserved upper stem-loop intact. This upper stem-loop is sufficiently weak to expose the RBS to enable translation to occur. Unlike earlier toehold switch mRNA sensors, the updated systems do not employ an RNA refolding domain downstream of the start codon, which could hamper translation of the output gene.

In some embodiments, toehold switches are synthetic (engineered) molecules. In other embodiments, toehold switches comprise endogenous, naturally occurring RNAs or regions thereof. See, for example, U.S. 2015/0275203. The stem domain can be as small as 12 bps, but in some cases will be longer than 12 bps, including 13, 14, 15, 16, 17, 18, 19, 20, or more base pairs in length. In other cases, the loop domain is complementary to a non-naturally occurring RNA. The toehold domain can be 5, 6, 7, 8, 9, 10, 11, 12, 13, 14, 15, 16, 17, 18, 19, 20, or more nucleotides in length.

The toehold switch further comprises a fully or partially double-stranded stem domain and a loop domain. In some embodiments, the stem comprises an initiation codon, and the loop domain comprises at least a portion of the RBS, and/or at least a portion of a reporter protein coding domain. The unpaired region upstream of the RBS in a toehold switch can be shortened or lengthened to modulate protein output and, in turn, device dynamic range. In some cases, the toehold and stem domains are complementary in sequence to a naturally occurring RNA. In other cases, the sequence detected can also be the complement of the naturally occurring RNA. For example, after isothermal amplification, it is possible to transcribe the anti-sense of the RNA rather than the sense.

The toehold switch can further comprise a thermodynamically stable double-stranded stem domain, a loop domain comprising a ribosome binding site, and a coding domain. In some embodiments, the loop domain is 11 nucleotides or 12 nucleotides in length. In some embodiments, the length of loop domains can be increased or decreased, for example, to alter reaction thermodynamics. In some embodiments, the gap between the end of the Shine-Dalgarno sequence and the start codon range from about 2 to about 20, from about 3 to about 15, or from about 4 to about 10 nucleotides. By way of example, the sequences shown in FIG. 14 including the 5' endo of the mRNA through to the start of the output gene.

In some embodiments, the toehold switch is configured to detect a portion of a pathogen genome that is conserved among two or more species or strains of the pathogen. In some embodiments, the toehold switch is configured to distinguish among two or more species or strain of the pathogen. For example, the Examples that follow describe identifying conserved sequence regions of SARS-CoV-2-specific nucleic acids suitable for isothermal amplification and toehold-switch-based detection. In some cases, toehold switches useful for the methods provided herein include, without limitation, synthetic SARS-CoV-2-specific toehold switches that comprise a fully or partially double-stranded stem domain, a loop domain, a toehold domain, and at least a portion of a coding sequence of a reporter gene, wherein the toehold domain and at least a portion of the stem domain are complementary to a target SARS-CoV-2 RNA sequence.

In some embodiments, the riboregulator stem forms intramolecularly, and has melting temperature of about 70° C.-100° C., about 80° C., about 85° C., about 90° C., 91° C., 92° C., 93° C., 94° C., 95° C., 96° C., 97° C., 98° C., or 99° C., based on free energy predictions. In some embodiments, the complementary region that binds to the target is at least about 8, 9, 10, 11, 12, 13, 14, 15, nucleotides in length. In some embodiments, the complementary region at least 11 nucleotides in length. In some embodiments, the complementary region is about 15, 20, 25, 30, 40, 50, 60, 70, 80 90, 100 or more nucleotides in length (see e.g., Green et al., 2014, Cell 159, 925-939, and Pardee et al, 2016, Cell 165, 1255-1266, incorporated herein by reference in their entireties).

Exemplary riboregulators (sensors) of the present technology are presented in FIG. 14.

As used herein "cell-free transcription-translation system" refers to an extract, lysate, or combination of components and buffers that allow for both transcription and translation of a target mRNA. A cell-free transcription-translation system can be eukaryotic, prokaryotic, or plant-based, as long as it is compatible with the transcriptional and translational regulatory sequences of the target nucleic acid sequences (e.g., promoters, ribosome binding sites), and the codons provided therein for translation of the reporter protein. By way of example, a transcription-translation system would include RNA polymerase, ribonucleotides, ribosomes, amino acids, tRNAs and any co-factors or other proteins required for transcription and translation of a target mRNA sequence. Cell-free transcription-translation systems are commercially available, and include but are not limited to rabbit reticulocyte lysate systems, insect cell lysate systems, wheat germ extracts, and *E. coli* extracts.

As used herein "cell-free protein expression system" refers to an extract, lysate, or combination of components and buffers that allow for translation of a target mRNA. A cell-free protein expression system can be eukaryotic, prokaryotic, or plant-based, as long as it is compatible with the translational regulatory sequences of the target nucleic acid sequences (e.g., riboregulator translational control sequences), and the codons provided therein for translation of the reporter protein. By way of example, a protein expression system would include ribosomes, amino acids, tRNAs and any co-factors or other proteins required for translation of a target mRNA sequence. Cell-free protein expression systems are commercially available, and include but are not limited to rabbit reticulocyte lysate systems, insect cell lysate systems, wheat germ extracts, and *E. coli* extracts.

Methods

The present technology relates to methods for detection of infectious agents such as SARS-CoV-2, the causative agent of COVID-19. While SARS-CoV-2 has been used herein as a model system for proof-of-concept, the present invention is not intended to be limited by detection of a single pathogen, and the disclosed methods and systems can be applied to detect other infective agents including, without limitation, virus, bacteria, and fungi.

The methods and compositions provided herein are based at least in part on the inventors' development of a rapid, highly sensitive assay for detection of SARS-CoV-2 that employs reagents outside of the standard PCR reagent pipeline. The assay can be adapted to colorimetric or fluorometric readout. It employs isothermal reactions that in principle can be run in highly parallel fashion, avoiding thermal cyclers, to enable large increases in the number of samples that can be measured simultaneously compared to conventional approaches. In addition, the reagents for the assay can be as low as $3 per cell-free readout and can be stabilized at room temperature to enable wide distribution and wide use. Moreover, the ability to run reactions at room temperature suggests that these assays can be used at home to enable convenient COVID-19 testing and to reduce the burden on healthcare practitioners during the pandemic. Consequently, the assays need not take place at centralized labs and can provide same-day, at-home results for patients who are in desperate need of care. Finally, the assays are nucleic acid based so they can provide improved specificity and sensitivity over antibody-based tests and can be rapidly repurposed for other pathogens, for instance if a new, more virulent SARS-Co V-2 strain emerges.

Accordingly, in a first aspect, provided herein are synthetic nucleic acid sequences and diagnostic platforms for detecting a SARS-CoV-2-specific nucleic acids in a sample. In some embodiments, synthetic nucleic acids of this disclosure comprise toehold switches, designed to target different genes in the SARS-CoV-2 genome. The SARS-CoV-2 genome encodes non-structural protein (nsp) (ORFlab), a RNA-dependent RNA polymerase (RdRp), an envelope protein (E), nucleoprotein (N), Spike protein (S), and membrane glycoprotein (M). The sequences of these gene are well known in the art and are easily accessible to the skilled artisan.

The assays provided herein employ nucleic acids obtained from patient samples (e.g., serum samples, saliva, nasal swabs, sputum) that are amplified using an isothermal amplification reaction.

In some embodiments, the method comprises or consists essentially of the following steps. A biological sample obtained from a subject is heated to release viral RNAs from viral particles present in the sample. In some embodiments, samples (e.g., saliva, nasopharyngeal swabs, etc.) are vortexed, and may be treated to inactivate virus (e.g., by heating to 650 for at least 30 minutes). In some embodiments, a buffer may be added to the sample (e.g., to a nasopharyngeal swab). Following the heating step, the released viral RNAs are amplified using an isothermal reaction. The resulting amplified products are then added to cell-free reactions, either in liquid phase or embedded on paper substrates, for sequence verification. In these cell-free reactions, sequence-specific riboregulators such as toehold switches and Single-Nucleotide-specific Programmable Riboregulators (SNIPRs) (see, e.g., Hong et al., Cell 180(5):1018-1032 (2020)) are used to bind to the amplified viral RNA and produce a desired output protein that can be interpreted by simple, readily available instrumentation.

In some embodiments, the method comprises (a) releasing viral RNAs from viral particles in a biological samples obtained from a subject; (b) amplifying the released viral RNA obtained from a biological sample of a subject, wherein amplifying comprises isothermal amplification; (c) contacting the amplified nucleic acid to a riboregulator, such as a toehold switch, wherein the toehold switch encodes at least a portion of a reporter protein and comprises one or more single-stranded toehold sequence domains that are complementary to a target SARS-Co V-2 nucleic acid or the reverse complement thereof, wherein the contacting occurs under conditions that allow translation of the coding domain in the presence of the target SARS-CoV-2 nucleic acid but not in the absence of the target nucleic acid; and (d) detecting the reporter protein as an indicator that the target SARS-Co V-2 nucleic acid is present in the amplified nucleic acids.

In some embodiments, the heating step is performed for different times and temperature combinations, including, without limitation, about 2 minutes at 98° C., about 10 minutes at 65° C., or about 10 minutes at 60° C.

In some embodiments, the isothermal reaction is nucleic acid sequence based amplification (NASBA) or reverse transcriptase recombinase polymerase amplification (RT-RP A), but other isothermal reactions can be employed. Other isothermal amplification methods include: loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RP A), and polymerase spiral reaction (PSR), which is described at nature.com/articles/srepl2723 on the World Wide Web. In some cases, recombinase polymerase amplification (RPA) is used with the "one-pot" amplification and detection methods provided herein. In such cases, the methods comprise performing reverse transcription (RT), RPA, and transcription (TX) methods in a single test tube. In other cases, LAMP (loop-mediated isothermal amplification) is performed. As described in the Examples that follow, the unimolecular aptamer-based sensors described herein can bind directly to DNA LAMP amplification products. Alternatively, the amplification protocol is configured to add promoter sites to DNA LAMP amplification products such that each LAMP DNA can generate multiple RNA copies for improved assay effectiveness.

In some embodiments, the riboregulators disclosed herein, such as a toehold switches comprise translational start sequences, such as RBS and start codons operably linked to a reporter element (e.g., at least a portion of an *E. coli* lacZ reporter element encoding 0-galactosidase), wherein the reporter element is 3' to the hairpin structure. As used herein, the term "operably linked" refers to a relationship between two nucleic acid sequences wherein the production or expression of one of the nucleic acid sequences is controlled by, regulated by, modulated by, etc., the other nucleic acid sequence. In some cases, the reporter protein is an enzyme such as beta-galactosidase. The enzyme can then cleave a suitable substrate to produce a detectable signal. Chlorophenol Red-β-D-galactopyranoside (CPRG), which changes from a yellow to a purple color upon cleavage by beta-galactosidase, can be used for a colorimetric output, while fluorescein di(β-D-galactopyranoside) produces bright green fluorescence upon cleavage by the enzyme for fluorometric detection. In other cases, the reporter protein can be a fluorescent protein for fluorescence detection, a chromoprotein for colorimetric protein detection, or an antigen-binding protein to enable capture and visualization of the riboregulator product. Other reporter proteins appropriate for the methods provided herein include, without limitation, enzymatic reporters (e.g., alkaline phosphatase, DHFR, CAT), fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc.

In some embodiments, the method employs programmable riboregulators known as toehold switches.

The term "colorimetric" is defined as an analysis where the reagent or reagents constituting the riboregulators system produce a color change in the presence or absence of an analyte. The degree the color changes in response to the analyte (e.g., target nucleic acid) may be quantified by colorimetric quantification methods known to those of ordinary skill in the art in. In some cases, standards containing known amounts of the selected analyte may be analyzed in addition to the sample to increase the accuracy of the comparison.

In some embodiments, it may be advantageous to adapt the methods described herein for high-throughput, reproducible, and rapid detection, for example in a clinical setting or in the field. When riboregulator output is coupled to a reporter element, such as fluorescence emission or a color change through enzymatic activity, the riboregulators act as genetically encodable sensors for virus RNAs in a sample. For example, such riboregulators can be provided in a device configured for rapid, reproducible detection in a clinical setting. In some embodiments, the device comprises a preserved paper test article, upon which any step(s) of the method provided herein can be performed. In preferred embodiments, the paper test article is preserved by freeze-drying. In such cases, riboregulator and methods provided herein can be performed at a cost of less than $3 per assay. In other embodiments, nucleic acids encoding the riboregulators can be freeze-dried in test tubes to render them stable at room temperature. These freeze-dried components can be reactivated upon addition of a sample and water, and can report on the presence of an endogenous nucleic acid of interest in the sample.

Any appropriate sample can be used according to the methods provided herein. In some embodiments, the sample is a biological sample obtained from an individual (e.g., a human subject, a nonhuman mammal). The sample is, in some embodiments, a diagnostic sample. The sample type will vary depending on the target pathogen. For example, SARS-CoV-2 can be detected in serum or blood samples or in nasopharyngeal or saliva samples. Accordingly, a diagnostic sample for detecting SARS-CoV-2 can be a serum sample or a blood sample or a nasopharyngeal or saliva sample. Samples appropriate for use according to the methods provided herein can also include, without limitation, food samples, drinking water, wastewater samples, environmental samples, and agricultural products. In some embodiments, samples appropriate for use according to the methods provided herein are "non-biological" in whole or in part. Non-biological samples include, without limitation, plastic and packaging materials, paper, clothing fibers, and metal surfaces. In some embodiments, the methods provided herein are used in food safety and food biosecurity applications, such as screening food products and materials used in food processing or packaging for the presence of pathogens in biological and/or non-biological samples. Other applications for which the methods provided herein include, without limitation, profiling species in an environment (e.g., water); profiling species in an human or animal microbiome; food safety applications (e.g., detecting the presence of a pathogenic species, determining or confirming food source/origin such as type of animal or crop plant); obtaining patient expression profiles (e.g., detecting expression of a gene or panel of genes (e.g., biomarkers) to monitor the patient's response to a therapeutic regimen, to select a therapeutic regimen suitable for the patient, or to detect exposure of the patient to a toxin or environmental agent that affects expression of the gene or a panel of genes.

In some embodiments, provided herein is a device for identifying a pathogen-associated nucleic acid, comprising a preserved paper test article, wherein the methods described herein are performed using the preserved paper test article. In some cases, the paper test article is preserved by freeze-drying.

In some embodiments, the device or methods may be used in combination with a portable electronic reader. In this manner, the electronic reader serves as companion technology that provides robust and quantitative measurements of method or device outputs. In some embodiments, the electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of toehold switch signal output, an acrylic chip that holds the freeze-dried, paper-based reactions is placed into the reader between a light source (e.g., to read optical density at excitation and emission wavelengths of light appropriate for and characteristic of a particular detectable reporter) and electronic sensors. In some cases, the light source is a light emitting diode (LED) light source. Samples can be read using onboard electronics. In this manner, a portable electronic reader can provide low-noise measurements of changes associated with the reporter element including changes in light transmission due to, for example, Lacz-mediated color change.

Articles of Manufacture

In another aspect, the present technology provides articles of manufacture useful for detecting a pathogen in a sample according to the methods provided herein. In certain embodiments, the article of manufacture is a kit for detecting SARS-CoV-2, where the kit comprises a SARS-CoV-2-specific riboregulator as a detecting agent, a plurality of preserved paper test articles as described herein, and an electronic optical reader. Optionally, a kit can further include instructions for performing the SARS-CoV-2 detection methods provided herein.

In some embodiments, provided herein is a kit for detecting a SARS-CoV-2-specific nucleic acid, where the kit comprises a plurality of preserved paper test articles, a SARS-CoV-2-specific detection agent, a plurality of toehold switches that encode at least a portion of a reporter protein and comprise one or more single-stranded toehold sequence domains that are complementary to a target SARS-CoV-2-specific nucleic acid or the reverse complement thereof, and an electronic optical reader. In some cases, the kit also comprises instructions for performing the SARS-CoV-2-specific detection methods provided herein.

In some embodiments, provided herein is a kit for detecting a SARS-CoV-2-specific nucleic acid, where the kit comprises a plurality of preserved test tube test articles, a SARS-Co V-2-specific detection agent, a plurality of toehold switches that encode at least a portion of a reporter protein and comprise one or more single-stranded toehold sequence domains that are complementary to a SARS-Co V-2-specific nucleic acid or the reverse complement thereof, and an electronic optical reader. In some cases, the kit also comprises instructions for performing the SARS-Co V-2-specific detection methods provided herein.

In some embodiments, provided herein is a kit for detecting a SARS-CoV-2-specific nucleic acid, where the kit comprises a plurality of preserved paper test articles, a SARS-CoV-2-specific detection agent, a plurality of SNIPRs that encode at least a portion of a reporter protein and comprise one or more single-stranded toehold sequence domains that are complementary to a target SARS-CoV-2-specific nucleic acid or the reverse complement thereof, and an electronic optical reader. In some cases, the kit also comprises instructions for performing the SARS-CoV-2-specific detection methods provided herein.

In another aspect, the present technology provides articles of manufacture useful for detecting a pathogen in a sample according to the methods provided herein. In some embodiments, the article of manufacture is a kit for detecting SARS-CoV-2, where the kit comprises a SARS-Co V-2-specific riboregulator as a detecting agent, a plurality of preserved test articles in a reaction tube as described herein, and an electronic optical reader. Optionally, a kit can further include instructions for performing the SARS-CoV-2 detection methods provided herein.

In some embodiments, provided herein is a kit for detecting a SARS-CoV-2-specific nucleic acid, where the kit comprises at least one primer pair, and at least one riboregulator, wherein if primer pair SEQ ID NO: 1 and SEQ ID NO: 8 is provided, then a riboregulator comprising SEQ ID NO: 27 and/or SEQ ID NO: 31 is provided; if primer pair SEQ ID NO: 6 and SEQ ID NO: 19 is provided, then a riboregulator comprising SEQ ID NO: 32 and/or SEQ ID NO: 34 is provided; (c) if primer pair SEQ ID NO: 3 and SEQ ID NO: 20 is provided, then a riboregulator comprising SEQ ID NO: 32 and/or SEQ ID NO: 34 is provided; and (d) if primer pair SEQ ID NO: 22 and SEQ ID NO: 24 is provided, then a riboregulator comprising SEQ ID NO: 50 and/or SEQ ID NO: 51 is provided.

ILLUSTRATIVE EMBODIMENTS

Embodiment 1. In a first embodiment, a method of detecting a target SARS-Co V-2 nucleic acid in a sample is provided, the method comprising the steps of: (a) heating biological sample obtained from a subject, whereby viral RNAs are released from viral particles present in the sample; (b) amplifying the released viral RN As, wherein amplifying comprises isothermal amplification; and (c) contacting the amplified nucleic acids to a toehold switch-based sensor, wherein the toehold switch-based sensor encodes at least a portion of a reporter protein and comprises one or more single-stranded toehold sequence domains that are complementary to a target SARS-CoV-2 nucleic acid or the reverse complement thereof, wherein the contacting occurs under conditions that allow translation of the coding domain in the presence of the target SARS-CoV-2 nucleic acid but not in the absence of the target nucleic acid; and (d) detecting the reporter protein as an indicator that the target SARS-CoV-2 nucleic acid is present in the amplified nucleic acids.

Embodiment 2. The method of embodiment 1, wherein the target SARS-CoV-2 nucleic acid is detectable at a concentration as low as 0.5 attoMolar (aM).

Embodiment 3. The method of embodiment 1, wherein the reporter protein, if present, is detectable in less than about 4 hours.

Embodiment 4. The method of embodiment 1, wherein the reporter protein, if present, is detectable in less than about 2.5 hours.

Embodiment 5. The method of embodiment 1, wherein the isothermal amplification is a method selected from NASBA and RT-RPA.

Embodiment 6. The method of embodiment 1, wherein the toehold switch-based or SNIPR sensor has a sequence selected from those set forth in FIG. 12.

Embodiment 7. A synthetic SARS-CoV-2-specific toehold switch sensor comprising a fully or partially double-stranded stem domain, a loop domain, a toehold domain, and at least a portion of a coding sequence of a reporter gene, wherein the toehold domain and at least a portion of the stem domain are complementary to a target SARS-CoV-2 RNA sequence.

Embodiment 8. The toehold switch sensor of embodiment 7, comprising a sequence selected from those set forth in FIG. 12.

Embodiment 9. A synthetic SARS-CoV-2-specific SNIPR sensor comprising a fully or partially double-stranded stem domain, a loop domain, a toehold domain, a spacer domain, a docking site (complementary region), and at least a portion of a coding sequence of a reporter gene, wherein the toehold domain, the docking site, and at least a portion of the stem domain are complementary to a target SARS-CoV-2 RNA sequence.

Embodiment 10. The SNIPR sensor of embodiment 9, comprising a sequence selected from those set forth in FIG. 12.

Embodiment 11. The method of embodiment 5, wherein the forward and reverse amplification primers comprise sequence selected from those set forth in FIG. 13 and FIG. 14.

Embodiment 12. The method of embodiment 1, wherein the reporter substrate is cleaved by an enzyme to generate a fluorescent signal.

Embodiment 13. The method of embodiment 12, wherein the reporter substrate is fluorescein di(s-D-galactopyranoside).

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The present embodiments have been described in terms of one or more preferred embodiments, and it should be appreciated that many equivalents, alternatives, variations, and modifications, aside from those expressly stated, are possible and within the scope of the embodiments.

EXAMPLES

This section demonstrates rapid, low-cost, sensitive platforms for detection of SARS-Co V-2. As illustrated in FIG. 2, the platforms use viral RN As released and amplified in samples obtained from subjects.

Example 1

To implement the SARS-CoV-2 assay, a library of toehold switches and SNIPRs was designed to detect conserved target sequence in five different regions of the viral genome: open reading frame 1b (Orf1b), the RNA-dependent RNA polymerase gene (RdRP), the envelope protein gene (E), and the nucleocapsid protein gene (N). All four of these sequence regions have been targeted in approved qRT-PCR assays for SARS-CoV-2 detection. A fifth region in the spike gene (S) has also been used and riboregulators for detection within this region are under development. It is important to note that SARS-Co V-2 is one of seven different coronaviruses that are known to infect humans and thus has sequence homology with these viruses that first circulated before 2019. In particular, SARS-CoV-2 has very high sequence homology with the SARS-CoV virus, the causative agent of severe acute respiratory syndrome (SARS) that led to outbreaks with high mortality beginning in 2002. RNA sensors with the capacity to distinguish between SARSCo V-2 and SARS-Co V are important for conclusive detection of COVID-19 cases.

Riboregulator computation design software (see e.g., Green et al., 2014, Pardee et al., 2016, and Ma et al., Synth Biol 3(1) 2018, incorporated herein by reference in its entirety) was used to generate at least a dozen toehold switches optimized for detection of each of the four SARS-CoV-2 target regions in the sense orientation. Targets were synthetic RNAs of about 200 nucleotides in length. A parallel set of SNIPRs for SARS-CoV-2 targets was also generated using open source automated SNIPR design software (see https://at github.com/Albert09111/SNIPR). DNA encoding the riboregulators was synthesized and inserted upstream of the lacZ gene to enable production of a beta-galactosidase output protein. The resulting toehold switch and SNIPR sensors with lacZ outputs were tested in cell-free transcription-translation reactions (purchased from NEB) using synthetic trigger RNA sequences from SARS-CoV-2. In general, screening experiments were done as describe in Pardee et al., 2016. Sample reads started immediately after the reactions were mixed and placed in the plate reader. Reactions were performed at 37° C. These screening experiments revealed multiple riboregulators that activated specifically in the presence of the viral RNA sequences and produced visible purple color upon CPRG cleavage. Optimal toehold switches for detection of the sense orientation targets RdRp and E, along with two different subregions of the N gene (NI and N3) are shown in FIG. 2. SNIPRs for detection of the same target regions were also identified. To determine the sequence specificity of the riboregulators, we also challenged the top-performing toehold switches and SNIPRs with SARS-CoV-2 RNAs along with RNAs from homologous regions in SARS-CoV. In some of these targets, the sequences of the SARS-CoV-2 and SAR-CoV differ by as little as a single base (e.g. the E gene). As shown in FIG. 3, the highly specific SNIPR sensors successfully distinguished between SARS-CoV-2 and SARS-CoV in all four target regions, while the toehold switches showed some crosstalk for the RdRp and E genes and good specificity within Orf1b.

Detection of the anti-sense viral sequences can be advantageous in some cases following isothermal amplification. Accordingly, a library of toehold switches that recognize the four target regions of SARS-CoV-2 in the anti-sense orientation was also tested. A library of SNIPRs for these targets is also under development. Reaction conditions were generally as described above. For initial screening, DNA encoding the toehold switches was inserted upstream of the lacZ-alpha peptide to provide a fast readout from the cell-free reactions. The lacZ-alpha peptide, a short peptide fragment from lacZ, complements with the much larger lacZ-omega peptide to form the active enzyme, and reduces reaction times as a result of its shorter length than full-length lacZ, which lowers protein synthesis and folding times. FIG. 4 shows the top toehold switches for the anti-sense Orf1b (SEQ ID NO: 27 and 31), RdRp (SEQ ID NO: 41 and 52), and E (SEQ ID NO: 50 and 51) genes identified during the screening process. To achieve lower signal production in the absence of the trigger RNA, cassettes expressing the sensor coupled to full-length lacZ were then constructed. FIG. 5 shows the output from these reactions demonstrating activation of the toehold switches by the SARS-CoV-2 trigger RNA and low output in the absence of the trigger. Toehold switches for detection of the anti-sense N gene were also constructed with both lacZ-alpha peptide and full-length lacZ outputs. FIG. 6 shows the performance of these sensors (see FIG. 14 for sensor sequences). The lacZ-alpha peptide systems activate faster than the full-length lacZ systems; however, the lacZ systems provide much lower background signal, which should reduce the likelihood of false-positive test results in the final SARS-CoV-2 assay.

To investigate the possibility of implementing the cell-free reaction in in-home or instrument-free contexts, the response of the toehold switches in room-temperature reactions was also evaluated. These experiments demonstrated that liquid-phase cell-free reactions could produce visible color changes within 2 to 2.5 hours (FIG. 7). In particular, toehold switch C9 for the N gene antisense sequence produced a dark red color using the full-length lacZ within two hours in the presence of the target RNA. A comparison reaction lacking the trigger retained the starting yellow color after two hours. These results demonstrate that the toehold switches can in principle be used at home without additional temperature control.

While colorimetric assays enable convenient detection by eye or with a smartphone camera, fluorimetric assays can be implemented using existing instrumentation in a conventional laboratory or using inexpensive combinations of lights sources and optical filters. Accordingly, the use of a fluorogenic substrate in the cell-free riboregulator assays with lacZ was also investigated. After screening multiple potential substrates, fluorescein di(s-D-galactopyranoside) (FDG) was identified as providing a strong green fluorescence upon cleavage by lacZ. FIG. 8 shows experimental results obtained using toehold switches for the antisense targets Orf1 b, N, and E. All three sensors (SEQ ID NOs: 27, 34, and 50) show strong green fluorescence in these plate reader measurements and show low background fluorescence in the absence of the trigger (FIG. 8A). Unexpectedly, the FDG substrate fluorescence can also be observed by eye as shown by a photograph of the paper-based reactions with (+) and with (−) the trigger RNA (FIG. 8B).

Having developed an array of functional riboregulators for SARS-CoV-2 targets, isothermal amplification reactions were implemented based on the comparatively low concentrations of the virus present in clinical samples. Custom primer design software was implemented to generate amplification primers optimal for use in NASBA and RT-RP A reactions. The software analyzes potential primers according to their melting temperatures, secondary structures, dimerization probability, and homology with other respiratory viruses to identify those most likely to perform well in NASBA or RT-RPA reactions. In addition, the resulting RNA amplicons from the reactions are assessed to favor those with low secondary structures to encourage efficient binding by downstream riboregulator reactions.

Figure 1:
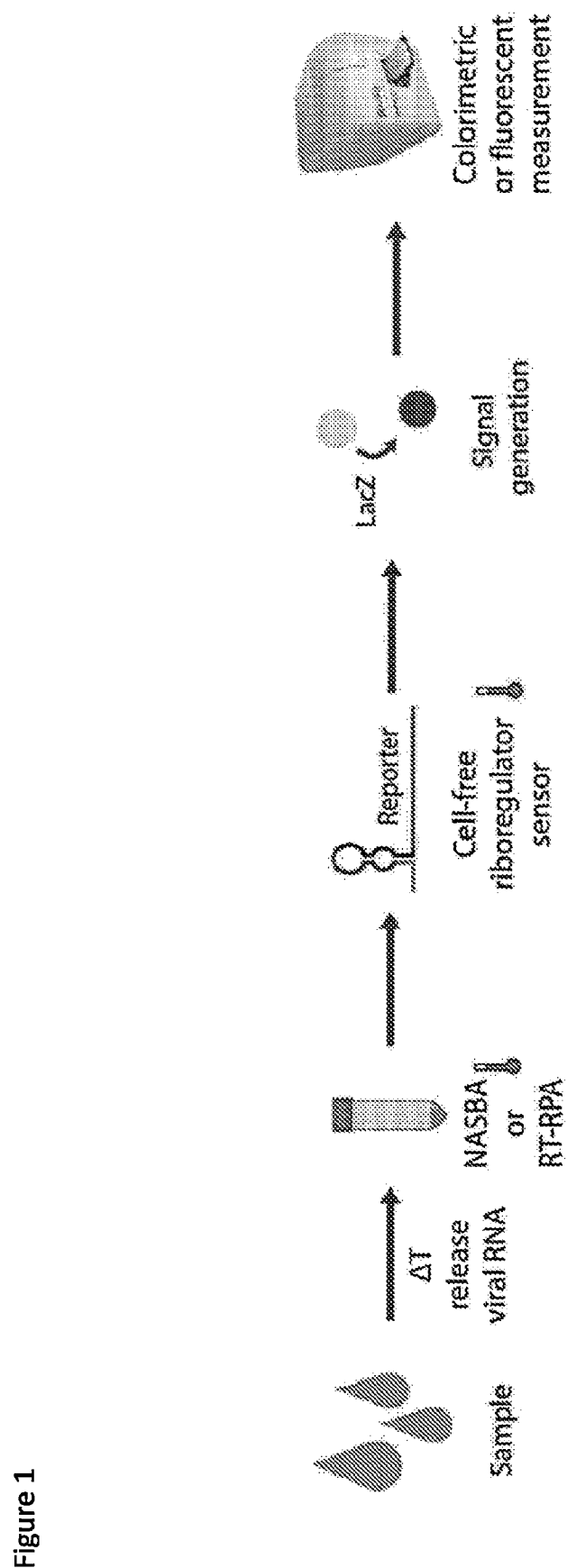
FIG. 1 shows an overview of an exemplary assay procedure. Heat is used to rapidly release RNA from viral particles. The released RNA is added to an isothermal amplification reaction and applied to a cell-free system containing a riboregulator for viral sequence identification. The lacZ produced in the reaction is then used to cleave a reporter substrate to provide a colorimetric or fluorometric signal that can be read by eye, smartphone camera, or plate reader.
Figure 9:
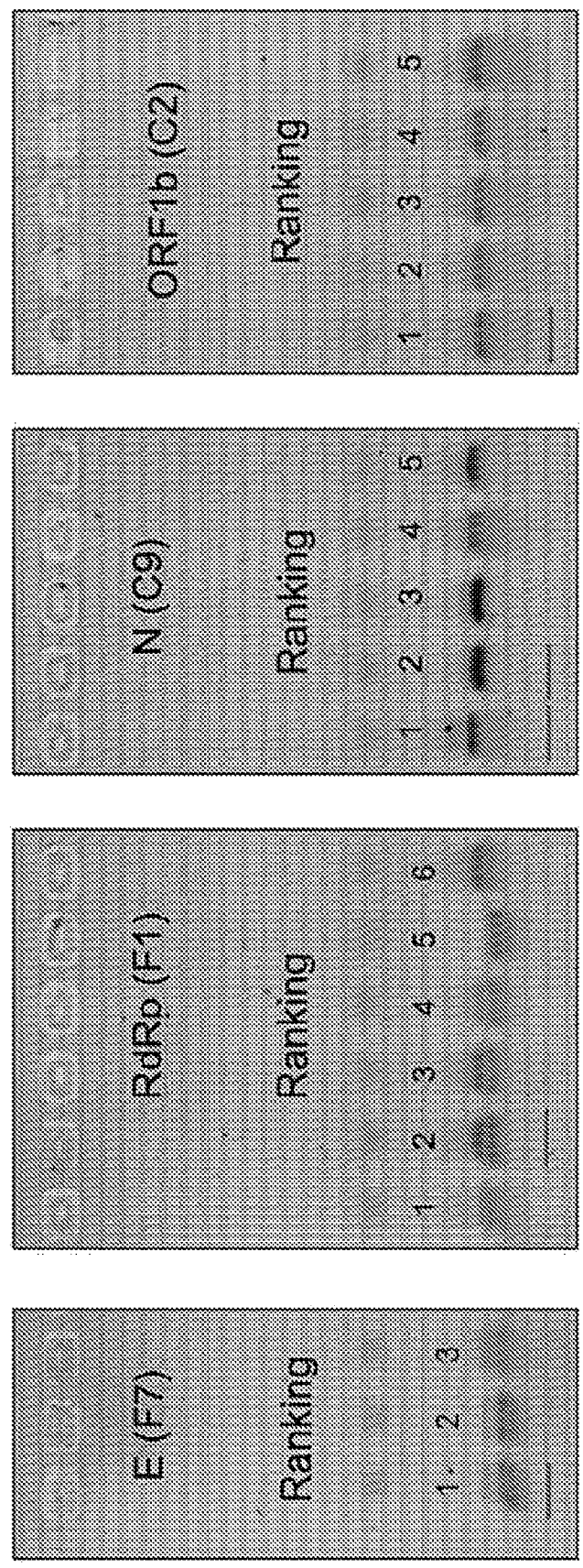
FIG. 9 shows gel electrophoresis analysis of RT-RPA products from 20-min 37° C. amplification reactions. All computer-designed primers produce clear DNA product bands from SARS-CoV-2 RNA concentrations supplied to the reactions at 125 copies/µL (~200 aM).

Reverse transcriptase, recombinase polymerase amplification reaction (RT-RPA reactions) were implemented by adding the M-MuL V reverse transcriptase (NEB, Inc.) to a standard RPA reaction mix (TwistDX, Inc.). RNA from heat-inactivated SARS-CoV-2 particles was then added to the reverse transcriptase, recombinase polymerase amplification reaction (RT-RPA) to a concentration of 125 copies/µL (−200 aM) in the reaction along with 480 nM concentration of the computer-designed RPA primers. The resulting reactions were then incubated at 37° C. and the products imaged used gel electrophoresis. FIG. 9 shows the RT-RPA products for different combinations of amplification primers for four different SARS-CoV-2 targets. We observed amplification from all combinations tested and selected one or two pairs of primers displaying clean banding patterns for further study. The selected primers (underlined in FIG. 9, and provided in FIGS. 12 and 13) were then tested using concentrations of 0.5 aM to 50 aM of SARS-CoV-2 genomic RNA in 40-minute RT-RPA reactions. Results are provided in FIG. 15. These assays demonstrated that RNA could be amplified from concentrations down to at least 0.5 aM, which corresponds to about 15 RNA copies in each 50 µL amplification reaction. Similar screening experiments were performed using combinations of primers in NASBA reactions.

The two optimal primer pairs for RT-RPA of the N gene (see FIG. 13, bold, and corresponding sequences in FIG. 12, bold) were then coupled with the antisense N gene sensor C9 (SEQ ID NO: 34) [Inventors, please confirm] for detection limit testing. This combined assay demonstrated that the toehold switches could successfully detect SARS-CoV-2 RNA down to a concentration of 0.5 aM or 15 copies (FIG. 10). In these reactions, FDG was used to generate a fluorescence signal and 0.7 µL of the RT-RPA product was added directly to a 5 µL total volume cell-free reaction for measurement. Based on these results, it should be possible to implement a completely room-temperature assay for SARS-CoV-2 detection since antisense N gene sensor C9 operates at room temperature and RT-RPA is compatible with these low temperatures as well.

Finally, NASBA reactions run for about 1 hour at 41° C. were also coupled with validated SNIPR sensors in paper-based cell-free reactions. As shown in FIG. 11, the SNIPRs successfully detected SARS-CoV-2 RNA down to concentrations of 10 copies within 50 minutes of the 37° C. cell-free reaction. Since the NASBA reactions are 5 µL, this corresponds to a concentration of ~3 aM. Sensors used in this experiment were SEQ ID NOs. 53-56 from FIG. 14.

Example 2: Detection of SARS-CoV-2 Using RT-LAMP and Toehold Switches

Toehold switch detection methods can also be combined with RT-LAMP reactions for detection of SARS-CoV and control mRNAs. RT-LAMP (reverse transcriptase loop-mediated isothermal amplification) is an isothermal amplification method that can take place at a constant reaction temperature of 60° C. to 65° C. After formation of cDNA by a reverse transcriptase enzyme, a combination of 4 to 6 primers is used to generate concatemer DNA products that feature exposed, single-stranded DNA loops that can be used for binding of toehold switches. The general assay protocol is shown in FIG. 18A-B. A clinical sample (e.g. nasopharyngeal swab, saliva sample) is subject to RNA extraction using either a brief heating step or a commercial column extraction method. The resulting RNA is then applied to an RT-LAMP reaction containing six different amplification primers at 61° C. for 20 to 60 minutes. The resulting DNA amplicons are then applied to a cell-free reaction on either paper or in a test tube. In the cell-free reaction, toehold switch sensors are transcribed and bind to the exposed single-stranded loops of the RT-LAMP amplicons. Activation of the toehold switches can then be read out through a reporter protein or reporter enzyme/substrate reaction. The reporter protein can be a fluorescent protein (e.g. GFP, RFP, YFP, etc., or a portion of a fluorescent protein) or a reporter enzyme (e.g. lacZ, or a portion of lacZ with lacZ-alpha subunit). The reaction can then be read out via fluorescence or a change in color.

To implement the assay, toehold switches were designed to target RT-LAMP amplicons produced from primer combinations previously described in the research literature (sequences of the RT-LAMP primers and toehold switches are provided at FIG. 14 and in the table named "Sequences," below). Toehold switch designs were modified by shortening the toehold domains between 4 to 5 nt to accommodate the loop domains of the RT-LAMP amplicons, which are shorter than the typical target regions provided by other amplification methods. This adjustment led to a target binding region of 31 to 32 nt for the toehold switches. Toehold switches were then constructed and tested against synthetic stem-loop DNA targets designed to replicate the expected RT-LAMP amplicon structure. FIG. 19A-D shows time-course curves of the most active of these toehold switches responding to the synthetic stem-loop DNA targets. The systems all activate strongly in the presence of the target strands. Signal in the absence of the target is observed as well, but the output is significantly lower than that observed with the target.

Top-performing toehold switches were then tested against RT-LAMP products. RT-LAMP was first performed using primers previously reported in the literature on samples spiked with inactivated SARS-CoV-2 virions. Following RT-LAMP reactions at 61° C. for 60 minutes, reaction products were added to cell-free systems containing toehold switch DNA templates (see FIG. 20). During the cell-free reactions, the toehold switches are transcribed and bind to the RT-LAMP loop regions and generate the fluorescence signals indicated in FIG. 21A-C after two hours. The resulting assays enable detection of SARS-CoV-2 RNA down to concentrations of 25 aM, which is sufficient for detection of the virus from clinical samples. The RT-LAMP/toehold switch assay was also performed against control 18S rRNA, which is a commonly used sample preparation control. These reactions also enabled detection of the control rRNA down to starting concentrations of 40 aM, which is sufficiently sensitive for application against clinical samples.

Sequences of Exemplary Functional LAMP Switches:

| Name | Sequence |
| --- | --- |
| TSgen2_Ref5A_nucleocapsid_targ_Bloop_antisense_lacZ_T37_top_3 | GGGUUCCAAUUAACACCAAUAGCAGUCCAGUUAUAGUUA UGAACAGAGGAGACAUAACAUGAACUGGACUAACCCAGU UAACCUGGCGGCAGCGCAAAAG (SEQ ID NO: 57) |
| 2B_N_B_32 nt_2 | GGGUCCUCAUCACGUAGUCGCAACAGUUCAAGAAAGUUA UAGUUAUGAACAGAGGAGACAUAACAUGAACUUUCUUAA CAAAGUUAACCUGGCGGCAGCGCAAAAG (SEQ ID NO: 58) |

| Name | Sequence |
|---|---|
| EAR_22_Ref16A_ctl_18S_rRNA_targ_Bloop_antisense_lacZ_T37_4 | GGGAGAGGUGAAAUUCUUGGACCGGCGCAAGACGGGACUUUAGAACAGAGGAGAUAAAGAUGCGUCUUGCGCCAAACCUGGCGGCAGCGCAAAAG (SEQ ID NO: 59) |
| TSgen2_Ref16A_ctl_18S_rRNA_targ_Floop_sense_lacZ_T37_top_3 | GGGUCCUAUUCCAUUAUUCCUAGCUGCGGGUUAUAGUUAUGAACAGAGGAGACAUAACAUGAACCCGCAGAACCGGGUUAACCUGGCGGCAGCGCAAAAG (SEQ ID NO: 60) |
| 2C_Spike_B_32_4 (FIG. 19B; 21B) | GGGAUAACCCUGUCCUACCAUUUAAUGAUGGUGUUGUUAUAGUUAUGAACAGAGGAGACAUAACAUGAACAACACCAACGUUGUUAACCUGGCGGCAGCGCAAAAG (SEQ ID NO: 61) |
| 2C_spike_F_32_3 (FIG. 19A; 21A) | GGGAGGUAAGAACAAGUCCUGAGUUGAAUGUAAAAGUUAUAGUUAUGAACAGAGGAGACAUAACAUGAACUUUUACAACAAAGUUAACCUGGCGGCAGCGCAAAAG (SEQ ID NO: 62) |
| EAR_22_Ref16A_ctl_18S_rRNA_targ_Bloop_antisense_lacZ_T37_2 (FIG. 19C; 21C) | GGGAGGUGAAAUUCUUGGACCGGCGCAAGACGGAGGACUUUAGAACAGAGGAGAUAAAGAUGUCCGUCUUGCGGAACCUGGCGGCAGCGCAAAAG (SEQ ID NO: 63) |
| TSgen2_Ref17A_ctl_ACTB_mRNA_targ_Floop_sense_lacZ_T37_top_2 (FIG. 19D) | GGGAUUUUCUCCAUGUCGUCCCAGUUGGGUUAUAGUUAUGAACAGAGGAGACAUAACAUGAACCCAACUAACUGGGUUAACCUGGCGGCAGCGCAAAAG (SEQ ID NO: 64) |

LAMP Primer Sequences (FIG. 21):

| Name | Sequence |
|---|---|
| Ref2C_spike_F3 | TCTTTCACACGTGGTGTT (SEQ ID NO: 65) |
| Ref2C_spike_B3 | GTACCAAAAATCCAGCCTC (SEQ ID NO: 66) |
| Ref2C_spike_FIP | CATGGAACCAAGTAACATTGGAAAACCTGACAAAGTTTTCAGATCC (SEQ ID NO: 67) |
| Ref2C_spike_BIP | CTCTGGGACCAATGGTACTAAGAGGACTTCTCAGTGGAAGCA (SEQ ID NO: 68) |
| Ref2C_spike_LF | GAAAGGTAAGAACAAGTCCTGAGT (SEQ ID NO: 69) |
| Ref2C_spike_LB | CTGTCCTACCATTTAATGATGGTGT (SEQ ID NO: 70) |
| Ref16A_ctl_18S_rRNA_F3 | GTTCAAAGCAGGCCCGAG (SEQ ID NO: 71) |
| Ref16A_ctl_18S_rRNA_B3 | CCTCCGACTTTCGTTCTTGA (SEQ ID NO: 72) |
| Ref16A_ctl_18S_rRNA_FIP | TGGCCTCAGTTCCGAAAACCAACCTGGATACCGCAGCTAGG (SEQ ID NO: 73) |
| Ref16A_ctl_18S_rRNA_BIP | GGCATTCGTATTGCGCCGCTGGCAAATGCTTTCGCTCTG (SEQ ID NO: 74) |
| Ref16A_ctl_18S_rRNA_LF | AGAACCGCGGTCCTATTCCATTATT (SEQ ID NO: 75) |
| Ref16A_ctl_18S_rRNA_LB | ATTCCTTGGACCGGCGCAAG (SEQ ID NO: 76) |

In summary, this disclosure demonstrates the design and implementation of a convenient assay for detection of SARS-Co V-2 that employs reagents outside of the standard PCR reagent pipeline. The assay can be adapted to colorimetric or fluorometric readout. It employs isothermal reactions that in principle can be run in highly parallel fashion, avoiding thermal cyclers, to enable large increases in the number of samples that can be measured simultaneously compared to conventional approaches. In addition, the reagents for the assay can be as low as $3 per cell-free readout and can be stabilized at room temperature to enable wide distribution and wide use. In addition, the ability to run reactions at room temperature suggests that these assays can be used at home to enable convenient COVID-19 testing and to reduce the burden on healthcare practitioners during the pandemic.

We claim:

1. A method of detecting a viral SARS-CoV-2 RNA in a sample from a subject, the method comprising the steps of:
   (a) heating the sample, whereby viral RNAs are released from viral particles present in the sample;
   (b) amplifying the released viral RNAs, wherein amplifying comprises isothermal amplification and produces a target nucleic acid; and
   (c) contacting the amplified target nucleic acid to one or more riboregulators, wherein each riboregulator comprises:
      (i) a first region that is complementary to at least a portion of the target nucleic acid or a reverse complement thereof;
      (ii) a second region that encodes a reporter protein and translation regulatory sequences;
   wherein the contacting occurs under conditions that allow translation of the reporter protein in the presence of the target nucleic acid or reverse complement thereof, but not in the absence of the target nucleic acid or reverse complement thereof; and
   (d) detecting the reporter protein as an indicator that the viral SARS-CoV-2 RNA is present in the subject sample;
   wherein each riboregulator first region comprises, independently, one of SEQ ID NOs: 26-51.

2. The method of claim 1, wherein the sample is selected from blood, serum, nasal swab, saliva, sputum.

3. The method of claim 1, wherein the riboregulator comprises a toehold switch.

4. The method of claim 1, wherein the riboregulator comprises a single-nucleotide-specific-programmable riboregulator (SNIPR).

5. The method of claim 1, wherein the isothermal amplification comprises nucleic acid sequence-based amplification (NASBA) or reverse transcriptase recombinase polymerase amplification (RT-RPA).

6. The method of claim 1, wherein step (c) comprises a cell-free transcription-translation system.

7. The method of claim 6, wherein the cell free transcription-translation system comprises a eukaryotic lysate.

8. The method of claim 6, wherein the cell free transcription-translation system comprises a prokaryotic lysate.

9. The method of claim 8, wherein the cell-free transcription-translation system comprises an *Escherichia coli* lysate.

10. The method of claim 6, wherein the cell free transcription-translation system comprises a plant-based lysate.

11. The method of claim 10, wherein the plant-based lysate comprises wheat germ lysate.

12. The method of claim 1, wherein the riboregulator second region encodes reporter protein selected from a fluorescent protein, a chromoprotein, an antigen-binding protein, and an enzyme.

13. The method of claim 12, wherein the reporter protein comprises a β-galactosidase gene or a functional subunit thereof.

14. The method of claim 13, wherein detection comprises enzymatic cleavage of substrate molecule by β-galactosidase.

15. The method of claim 14, wherein the substrate molecule is one or more of chlorophenol Red-β-D-galactopyranoside (CPRG) and fluorescein di((β-D-galactopyranoside).

16. The method of claim 1, wherein the reporter protein, if present, is detectable in less than about 4 hours.

17. The method of claim 1, wherein the reporter protein, if present, is detectable in less than about 2.5 hours.

18. The method of claim 1, wherein the subject is human.

19. The method of claim 18, wherein the isothermal amplification comprises NASBA or RT-RPA, and one or more primer pairs selected from:
   (a) SEQ ID NO: 1 and SEQ ID NO: 8;
   (b) SEQ ID NO: 6 and SEQ ID NO: 19;
   (c) SEQ ID NO: 3 and SEQ ID NO: 20; and
   (d) SEQ ID NO: 22 and SEQ ID NO: 24.

* * * * *